(12) United States Patent
Kobayashi et al.

(10) Patent No.: US 8,541,394 B2
(45) Date of Patent: Sep. 24, 2013

(54) AMINOGLYCOSIDE ANTIBIOTICS

(75) Inventors: Yoshihiko Kobayashi, Yokohama (JP); Yoshihisa Akiyama, Tokyo-To (JP); Takeshi Murakami, Minami-Ashigara (JP); Nobuto Minowa, Yokohama (JP); Masaki Tsushima, Kawasaki (JP); Yukiko Hiraiwa, Kyoto (JP); Shoichi Murakami, Yokohama (JP); Mitsuhiro Abe, Yonago (JP); Kazushige Sasaki, Kawasaki (JP); Shigeru Hoshiko, Atami (JP); Toshiaki Miyake, Yokohama (JP); Yoshiaki Takahashi, Tokyo-To (JP); Daishiro Ikeda, Tokyo-To (JP)

(73) Assignees: Meiji Seika Pharma Co., Ltd., Tokyo-To (JP); Microbial Chemistry Research Foundation, Tokyo-To (JP)

( * ) Notice: Subject to any disclaimer, the term of this patent is extended or adjusted under 35 U.S.C. 154(b) by 0 days.

(21) Appl. No.: 13/413,979

(22) Filed: Mar. 7, 2012

(65) Prior Publication Data
US 2012/0165283 A1 Jun. 28, 2012

Related U.S. Application Data

(62) Division of application No. 12/227,861, filed as application No. PCT/JP2007/061209 on Jun. 1, 2007, now Pat. No. 8,148,504.

(30) Foreign Application Priority Data

Jun. 2, 2006 (JP) ................. 2006-155062

(51) Int. Cl.
*A61K 31/702* (2006.01)
*A61P 31/04* (2006.01)

(52) U.S. Cl.
USPC .......................................... 514/61

(58) Field of Classification Search
None
See application file for complete search history.

(56) References Cited

U.S. PATENT DOCUMENTS

| | | | |
|---|---|---|---|
| 3,982,996 | A | 9/1976 | Daum et al. |
| 4,001,208 | A | 1/1977 | Umezawa et al. |
| 4,147,861 | A | 4/1979 | Umezawa et al. |
| 4,410,516 | A | 10/1983 | Umezawa et al. |
| 2007/0161581 | A1 | 7/2007 | Minowa et al. |

FOREIGN PATENT DOCUMENTS

| | | |
|---|---|---|
| JP | 49-62442 | 6/1974 |
| JP | 51-48634 | 4/1976 |
| JP | 51-108041 | 9/1976 |
| JP | 55-151597 | 11/1980 |
| JP | 57-53496 | 3/1982 |
| WO | 2005/070945 | 8/2005 |

OTHER PUBLICATIONS

Cohen, M. L., Nature, "Changing patterns of infectious disease", 2000, vol. 406, pp. 762-767.*
WordNet Search—3.0, "prevent"; also available at http://wordnetweb.princeton.edu/perl/webwn; last viewed Oct. 29, 2012.*
International Search Report mailed Jul. 3, 2007, in corresponding International Application No. PCT/JP2007/061209.
W. Shier et al., "Preparation of two New Aminoglycoside Antiobiotics", Journal of Antibiotics, vol. 23, No. 1, pp. 51-53, 1970.
Morissette, S. L. et al., Advanced Drug Delivery Reviews, "High-throughput crystallization: polymorphs, salts, co-crystals and solvates of pharmaceutical solids", vol. 56, pp. 275-300 (2004) (cited by Examiner in parent application U.S. Appl. No. 12/227,861).
Vippagunta, S. R. et al., Advanced Drug Delivery Reviews, "Crystalline solids", vol. 48, pp. 3-26 (2001) (cited by Examiner in parent application U.S. Appl. No. 12/227,861).
International Preliminary Report on Patentability mailed Jan. 22, 2009, in corresponding International Application No. PCT/JP2007/061209.
Japanese Office Action (with English translation) issued Aug. 28, 2012 in corresponding Japanese Patent Application No. 2008-520543.

* cited by examiner

*Primary Examiner* — Shaojia Anna Jiang
*Assistant Examiner* — Bahar Craigo
(74) *Attorney, Agent, or Firm* — Wenderoth, Lind & Ponack, L.L.P.

(57) ABSTRACT

This invention relates to novel aminoglycoside antibiotics, which have potent antimicrobial activity against bacteria, which induce infectious diseases, particularly MRSA, and has no significant nephrotoxicity, and process for producing them. More particularly, the present invention relates to compounds represented by formula (Ia) or their pharmacologically acceptable salts or solvates, or their diastereomer mixtures, antimicrobial agents comprising them, and a process for producing them.

[Chemical formula 1]

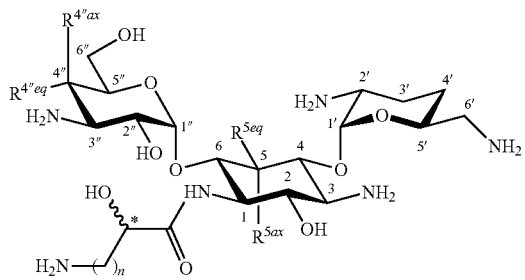

5 Claims, No Drawings

AMINOGLYCOSIDE ANTIBIOTICS

This application is a Divisional of U.S. application Ser. No. 12/227,861, filed Dec. 1, 2008 now U.S. Pat. No. 8,148,504, which is a national stage application of International Application No. PCT/JP2007/061209 filed Jun. 1, 2007

RELATED APPLICATION

The present application claims priority to Japanese Patent Application No. 155062/2006 filed on Jun. 2, 2006, the entire disclosure which is incorporated herein by reference.

BACKGROUND OF THE INVENTION

1. Field of the Invention

The present invention relates to novel aminoglycoside antibiotics characterized in that they are effective against bacteria which induce clinically severe infectious diseases, particularly against methicillin-resistant *Staphylococcus aureus* (MRSA), and have a low level of nephrotoxicity. The present invention also relates to novel intermediates useful for the production of the aminoglycoside antibiotics.

2. Background Art

In recent years, drug resistant bacteria resistant to antimicrobial agents used for the treatment of infectious diseases have appeared, and the treatment of infectious diseases induced by the resistant bacteria has become a major problem in clinical practice. In particular, MRSA is known as one of major drug resistant bacteria, which rapidly propagate through hospital infection and induce clinically severe infectious diseases, and the development of therapeutic agents for the infectious diseases has been energetically made.

Aminoglycoside antibiotics have a broad antimicrobial spectrum from gram-positive bacteria to gram-negative bacteria and have potent sterilizing power. Accordingly, the aminoglycoside antibiotics are expected to function as promising medicaments which can overcome various resistant bacteria including MRSA, and studies on the derivatives have been continuously carried out.

For example, Journal of Antibiotics, Vol. 24, 1971, p. 485 discloses that various derivatives of kanamycin, which is an aminoglycoside antibiotic, could be synthesized and 3',4'-deoxykanamycin B (dibekacin) could be discovered from the kanamycin derivatives. Dibekacin is widely used as a chemotherapeutic agent effective for resistant bacteria since 1975.

Journal of Antibiotics, Vol. 26, 1973, p. 412 discloses (S)-1-N-(4-amino-2-hydroxybutyryl)dibekacin (arbekacin) obtained by acylating the amino group at 1-position of dibekacin with an aminohydroxybutyric acid. Further, Japanese Patent Publication No. 10719/1988 discloses a production process of arbekacin.

Arbekacin has been used as a therapeutic agent for MRSA infectious diseases from the end of 1990. Arbekacin is known to have a broad antimicrobial spectrum from gram-positive bacteria including MRSA to gram-negative bacteria including *Pseudomonas aeruginosa*. Ten years or more have passed since arbekacin has become used as a therapeutic agent for MRSA infectious diseases. Despite this fact, there is no report about a severely enhanced resistance. On the other hand, JAPANESE SOCIETY OF CHEMOTHERAPY, Vol. 50, 2002, p. 494 reports that some clinically isolated MRSAs have lowered sensitivity to arbekacin.

Studies on various arbekacin analogues have been continuously carried out. For example, WO 2005/070945 discloses that a group of compounds, characterized in that the steric configuration of the site corresponding to the 5-position of arbekacin has been inverted and various substituents have been introduced, have antimicrobial activity against MRSA.

On the other hand, nephrotoxicity is known, from long ago, as a side effect of aminoglycoside antibiotics. There is also a report about clinical influence of arbekacin (Japanese Patent Laid-Open No. 164696/1980) on the kidney (JAPANESE SOCIETY OF CHEMOTHERAPY, Vol. 51, 2003, p. 717).

In subject No. F-716 in the 44th Interscience Conference on Antimicrobial Agents and Chemotherapy (2004), the present inventors describe, regarding an arbekacin analogue (compound No. TS2037: 5,4"-diepiarbekacin) described in WO 2005/070945, the results of the evaluation of nephrotoxicity using proximal uriniferous tubule epithelial cells of the kidney of pigs and using β-N-acetyl-D-glucosaminidase (hereinafter referred to as "NAG") as an index. The results show that the nephrotoxicity of the arbekacin analogue is higher than that of arbekacin.

Studies on various methods for reducing the nephrotoxicity of aminoglycoside antibiotics have hitherto been made. The combined use of an aminoglycoside antibiotic and a compound for reducing the nephrotoxicity is reported as one of such methods. For example, fosfomycin is known to reduce the nephrotoxicity of some aminoglycoside antibiotics. Further, in a test using rats, there is a report that the combined use of fosfomycin and arbekacin reduces the nephrotoxicity (The Japanese Journal of Antibiotics, Vol. 47, 1994, p. 664).

A method using the so-called TDM (therapeutic drug monitoring), in which a high level of therapeutic effect is realized while suppressing the side effect by making a medicine administration plan based on Pharmacokinetics and Pharmacodynamics, has recently been studied. For example, there is a report that TDM is also utilized for anti-MRSA treatment with arbekacin (JAPANESE SOCIETY OF CHEMOTHERAPY, Vol. 51, 2003, p. 717).

When conventional aminoglycoside antibiotics, which are used clinically, are used solely, however, it is still required to reduce the nephrotoxicity while maintaining a broad antimicrobial spectrum and potent antimicrobial activity against bacteria, which induce severe infectious diseases, including MRSA. Accordingly, in aminoglycoside antibiotics, the development of a novel compound having a broad antimicrobial spectrum and potent sterilizing power and, at the same time, having a low level of nephrotoxicity has been desired. Further, for the conventional aminoglycoside antibiotics, the appearance of drug resistant bacteria has become a problem, and compounds, which have excellent antimicrobial activity also against the drug resistant bacteria, have been still required. Furthermore, when the production of excellent antibiotics is taken into consideration, studies on stable production of the antibiotics are also a critical issue.

SUMMARY OF THE INVENTION

The present inventors have now succeeded in producing novel compounds represented by formula (Ia) which has a broad antimicrobial spectrum and excellent antimicrobial activity as well as a low level of nephrotoxicity. The present inventors have further found that the novel compound has a high level of antimicrobial activity against strains found in clinically isolated MRSAs, which possess a low level of sensitivity against arbekacin.

The present inventors have further found a production process useful for stable production of the novel compounds, and an intermediate important for the production of the novel compounds.

The present invention has been made based on such finding.

Accordingly, an object of the present invention is to provide novel compounds having a broad antimicrobial spectrum and excellent antimicrobial activity as well as a low level of nephrotoxicity, and synthetic intermediates for the compounds.

According to the present invention, there is provided a compound represented by formula (Ia) or its diastereomer mixture with respect to the carbon atom attached with *, or their pharmacologically acceptable salts or solvates.

[Chemical formula 1]

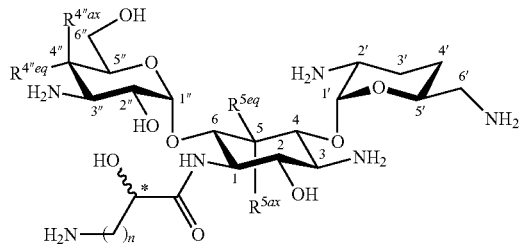

(Ia)

wherein $R^{5ax}$ and $R^{5eq}$, which may be the same or different, represent a hydrogen atom or hydroxyl, $R^{4''ax}$ and $R^{4''eq}$, which may be the same or different, represent a hydrogen atom or hydroxyl, n is an integer of 1 to 4, and the configuration of carbon atom attached with * represents R or S.

Further, according to the present invention, there is provided an intermediate useful for the synthesis of the compound represented by formula (Ia).

The compound represented by formula (Ia) according to the present invention exhibits a broad antimicrobial spectrum and excellent antimicrobial activity and can realize the avoidance of severe nephrotoxicity. Further, the compound represented by formula (Ia) can also exhibit excellent antimicrobial activity against MRSAs having a low level of sensitivity against arbekacin. The fact that the nephrotoxicity of the compound represented by formula (Ia) is lower than that of arbekacin, is advantageous in the application of the compound, for example, to patients suffering from infectious diseases. Accordingly, the compound represented by formula (Ia) according to the present invention can be advantageously utilized in the treatment of infectious diseases including MRSAs. Further, the compound represented by formula (Ia) can be stably supplied through compounds represented by formula (Xa), (Xb), or (XXV) which will be described later, and can be advantageously utilized as a therapeutic agent for infectious diseases.

DETAILED DESCRIPTION OF THE INVENTION

The term "alkyl" as used herein as a group or a part of a group means straight chain, branched chain or cyclic alkyl unless otherwise specified. The term "aryl" means phenyl or naphthyl unless otherwise specified. The term "arylalkyl" means alkyl in which one or more hydrogen atoms are substituted by aryl.

Compounds Represented by Formula (Ia)

It is a feature of the compounds represented by formula (Ia) to have a hydroxyl group at its 2-position.

[Chemical formula 2]

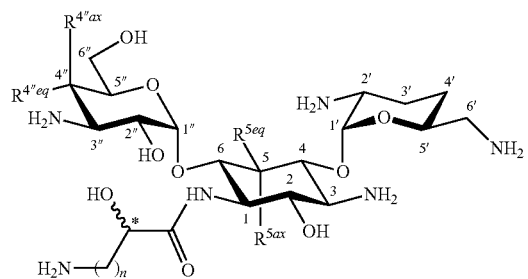

(Ia)

The compound having the above structure possesses a low level of nephrotoxicity and, at the same time, possesses a broad antimicrobial spectrum of gram-positive bacteria including MRSAs to gram-negative bacteria including *Pseudomonas aeruginosa* and excellent antimicrobial activity.

In the compounds represented by formula (Ia) in a preferred embodiment of the present invention, $R^{5ax}$ and $R^{5eq}$ are different from each other and represent a hydrogen atom or hydroxyl, and $R^{4''ax}$ and $R^{4''eq}$ are different from each other and represent a hydrogen atom or hydroxyl.

In the compounds represented by formula (Ia), n is preferably 1 to 3, more preferably 1 to 2.

Further, in the compounds represented by formula (Ia) in a preferred embodiment of the present invention, the steric configuration of the hydroxyl group at 5-position is equatorial. Accordingly, in the compounds represented by formula (Ia) in the above embodiment, $R^{5ax}$ represents a hydrogen atom, and $R^{5eq}$ represents hydroxyl. In the compounds represented by formula (Ia) in a more preferred embodiment of the present invention, $R^{4''ax}$ and $R^{4''eq}$ are different from each other, and represent a hydrogen atom or hydroxyl.

In a more preferred embodiment of the present invention, there are provided compounds represented by formula (I) or their pharmacologically acceptable salts or solvates.

[Chemical formula 3]

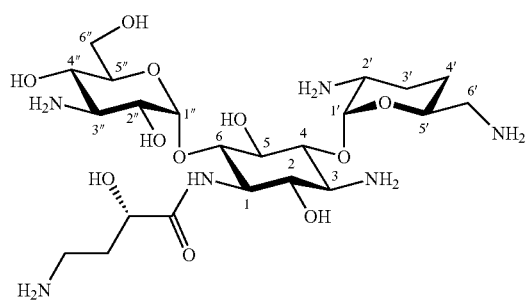

(I)

Further, in the compounds represented by formula (Ia) in another embodiment of the present invention, the steric configuration of the hydroxyl group at the 5-position is axial. Accordingly, in the compounds represented by formula (Ia) in the above embodiment, $R^{5ax}$ represents hydroxyl, and $R^{5eq}$ represents a hydrogen atom. In the compounds represented by formula (Ia) in a more preferred embodiment of the present invention, $R^{4''ax}$ and $R^{4''eq}$ are different from each other, and represent a hydrogen atom or hydroxyl.

The compounds represented by formula (Ia) may exist as a salt. Examples of such salts include pharmaceutically acceptable nontoxic salts. Specific examples thereof include hydrohalides such as hydrofluorides, hydrochlorides, hydrobromides, and hydroiodides, inorganic acid salts such as sulfates, nitrates, phosphates, perchlorates, and carbonates, salts of carboxylic acids such as acetic acid, trichloroacetic acid, trifluoroacetic acid, hydroxyacetic acid, lactic acid, citric acid, tartaric acid, oxalic acid, benzoic acid, mandelic acid, butyric acid, maleic acid, propionic acid, formic acid, and malic acid, salts of amino acids such as alginic acid, aspartic acid, and glutamic acid, and salts of sulfonic acid such as methanesulfonic acid and p-toluenesulfonic acid. Preferred are inorganic acid salts such as sulfates.

The compounds represented by formula (Ia) or their pharmacologically acceptable salts may exist as their solvates. Preferred solvates include hydrates or ethanolates.

As described above, the compounds represented by formula (Ia) may be the form of a diastereomer mixture with respect to the carbon atom attached with *, and the present invention includes this embodiment as well.

Synthetic Intermediates

The compounds represented by formula (Ia) may be produced by the following two processes. According to these processes, the compounds represented by formula (Ia) can be advantageously produced through synthetic intermediates which will be described later.

Synthetic Intermediates in First Production Process

In the first production process according to the present invention, compounds represented by formula (Xa) and formula (Xb) are used as synthetic intermediates.

Accordingly, in one embodiment of the present invention, compounds represented by formula (Xa) are provided.

[Chemical formula 4]

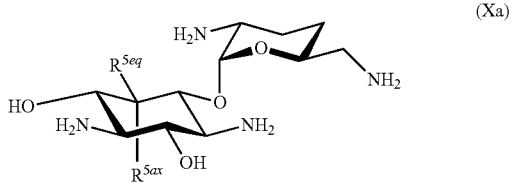

(Xa)

wherein $R^{5ax}$ and $R^{5eq}$ are different from each other and represent a hydrogen atom or hydroxyl.

In another embodiment of the present invention, there are provided compounds represented by formula (Xb).

[Chemical formula 5]

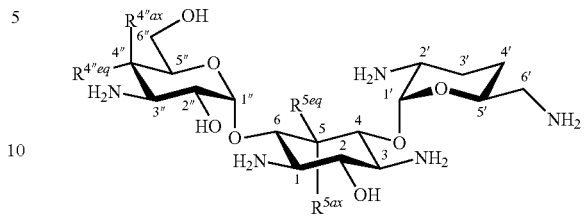

(Xb)

wherein $R^{5ax}$ and $R^{5eq}$ are different from each other and represent a hydrogen atom or hydroxyl, and
$R^{4''ax}$ and $R^{4''eq}$ are different from each other and represent a hydrogen atom or hydroxyl.

In a preferred embodiment of the present invention, the compounds represented by formula (Xb) are compounds represented by formula (XIV).

[Chemical formula 6]

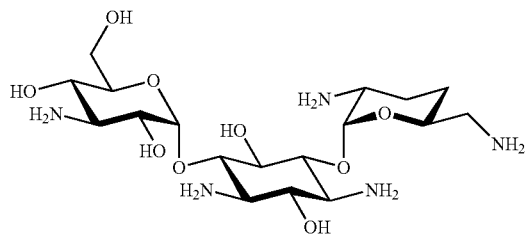

(XIV)

Synthetic Intermediates in Second Production Process According to Present Invention In the second production process according to the present invention, compounds represented by formula (XXV) or their diastereomer mixtures with respect to the carbon atom attached with * are used as synthetic intermediates. In the compounds represented by formula (XXV) in this production process, the steric configuration of the hydroxyl group at 5-position is equatorial. Accordingly, the second production process is suitable for the production of compounds which are represented by formula (Ia) and of which the steric configuration of the hydroxyl group at 5-position is equatorial.

[Chemical formula 7]

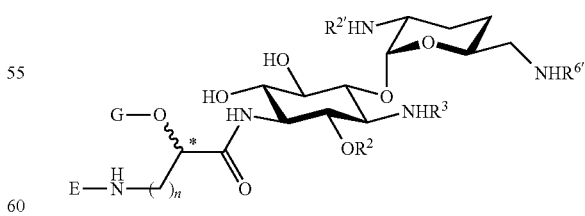

(XXV)

wherein $R^2$ and G represent a protective group for hydroxyl group; $R^3$, $R^{2'}$, $R^{6'}$ and E represent a protective group for amino group; n is an integer of 1 to 4; and the steric configuration of carbon atom attached with * represents R or S.

In the compounds represented by formula (XXV) in a more preferred embodiment of the present invention, $R^2$ represents optionally substituted aryl C1-3 alkyl, $R^3$, $R^{2'}$ and $R^{6'}$, which may be the same or different, represent optionally substituted C1-6 alkylsulfonyl, optionally substituted arylsulfonyl, or optionally substituted C1-6 alkyloxycarbonyl, E represents optionally substituted C1-6 alkyloxycarbonyl, and G represents a hydrogen atom, optionally substituted C1-6 alkylcarbonyl, or optionally substituted arylcarbonyl.

In the compounds represented by formula (XXV), aryl C1-3 alkyl group represented by $R^2$ is preferably aryl C1-2 alkyl, more preferably benzyl.

One or more hydrogen atoms in the aryl C1-3 alkyl group represented by $R^2$ are optionally substituted, for example, by methoxy or nitro. Specific examples of substituted aryl C1-3 alkyl include methoxybenzyl or nitrobenzyl.

In the compounds represented by formula (XXV), C1-6 alkylsulfonyl group represented by $R^3$, $R^{2'}$ or $R^{6'}$ is preferably C1-3 alkylsulfonyl, more preferably methanesulfonyl.

One or more hydrogen atoms in the C1-6 alkylsulfonyl group represented by $R^3$, $R^{2'}$ or $R^{6'}$ are optionally substituted, for example, by optionally substituted phenyl (phenyl or tolyl). Examples of substituted C1-6 alkylsulfonyl groups include benzylsulfonyl or toluenesulfonyl.

One or more hydrogen atoms in the arylsulfonyl group represented by $R^3$, $R^{2'}$ or $R^{6'}$ are optionally substituted, for example, by methyl. Specific examples of optionally substituted arylsulfonyl groups include benzylsulfonyl or toluenesulfonyl.

In the compounds represented by formula (XXV), preferably, the C1-6 alkyloxycarbonyl group represented by $R^3$, $R^{2'}$ or $R^{6'}$ is C1-4 alkyloxycarbonyl, more preferably methoxycarbonyl or tert-butoxycarbonyl.

One or more hydrogen atoms in the C1-6 alkyloxycarbonyl group represented by $R^3$, $R^{2'}$ or $R^{6'}$ are optionally substituted, for example, by optionally substituted phenyl (for example, phenyl, methoxyphenyl, or nitrophenyl). Specific examples of the substituted C1-6 alkyloxycarbonyl groups include benzyloxycarbonyl, tert-butoxycarbonyl, p-methoxybenzyloxycarbonyl or p-nitrobenzyloxycarbonyl.

In the compounds represented by formula (XXV), the C1-6 alkyloxycarbonyl groups represented by E is preferably C1-3 alkyloxycarbonyl, more preferably methoxycarbonyl or ethoxycarbonyl, still more preferably methoxycarbonyl.

One or more hydrogen atoms in the C1-6 alkyloxycarbonyl group represented by E are optionally substituted, for example, by optionally substituted phenyl (for example, phenyl, methoxyphenyl, or nitrophenyl). Accordingly, specific examples of the C1-6 alkyloxycarbonyl group substituted by optionally substituted phenyl include benzyloxycarbonyl, p-methoxybenzyloxycarbonyl, and p-nitrobenzyloxycarbonyl.

In the compounds represented by formula (XXV), the C1-6 alkylcarbonyl group represented by G is preferably C1-3 alkylcarbonyl, more preferably acetyl.

One or more hydrogen atoms in the C1-3 alkylcarbonyl group represented by G are optionally substituted, for example, by a halogen atom such as chlorine, bromine or fluorine, and specific examples of the substituted C1-3 alkylcarbonyl group include trichloroacetyl and trifluoroacetyl.

In the compounds represented by formula (XXV), the arylcarbonyl group represented by G is preferably benzoyl.

One or more hydrogen atoms in the arylcarbonyl group represented by G are optionally substituted, for example, by phenyl, a halogen atom such as chlorine, bromine or fluorine, nitro or methoxy. Specific examples of the substituted arylcarbonyl group include p-phenylbenzoyl, p-bromobenzoyl, p-nitrobenzoyl, and p-methoxybenzoyl.

In the compounds represented by formula (XXV), the aryl C1-3 alkyl group represented by G is preferably aryl C1-2 alkyl, more preferably benzyl or triphenylmethyl.

Further, one or more hydrogen atoms in the aryl C1-3 alkyl group represented by G are optionally substituted, for example, by methoxy. Specific examples of the substituted C1-3 alkylsulfonyl group include p-methoxybenzyl.

In the compounds represented by formula (XXV), n is 1 to 4, preferably 1 to 3, more preferably 1 or 2.

In the compounds represented by formula (XXV) in a more preferred embodiment of the present invention, $R^2$ represents aryl C1-3 alkyl optionally substituted by methoxy or nitro, $R^3$, $R^{2'}$ and $R^{6'}$, which may be the same or different, represent C1-6 alkylsulfonyl optionally substituted by optionally substituted phenyl, arylsulfonyl optionally substituted by methyl, or C1-6 alkyloxycarbonyl optionally substituted by optionally substituted phenyl, E represents C1-6 alkyloxycarbonyl optionally substituted by optionally substituted phenyl, and G represents a hydrogen atom, C1-6 alkylcarbonyl, arylcarbonyl, or aryl C1-3 alkyl optionally substituted by methoxy.

In the compounds represented by formula (XXV) in a further preferred embodiment of the present invention, $R^2$ represents aryl C1-2 alkyl optionally substituted by methoxy or nitro, $R^3$, $R^{2'}$ and $R^{6'}$, which may be the same or different, represent C1-3 alkylsulfonyl optionally substituted by optionally substituted phenyl, arylsulfonyl optionally substituted by methyl, or C1-4 alkyloxycarbonyl optionally substituted by optionally substituted phenyl, E represents C1-4 alkyloxycarbonyl optionally substituted by optionally substituted phenyl, and G represents a hydrogen atom, C1-3 alkylcarbonyl, arylcarbonyl, or aryl C1-2 alkyl optionally substituted by methoxy.

In the compounds represented by formula (XXV) in a further preferred embodiment of the present invention, $R^2$ represents optionally substituted aryl C1-3 alkyl, all of $R^3$, $R^{2'}$, $R^{6'}$ and E represent optionally substituted C1-6 alkyloxycarbonyl, and G represents optionally substituted aryl C1-3 alkyl.

In the compounds represented by formula (XXV) in a further preferred embodiment of the present invention, $R^2$ represents optionally substituted aryl C1-2 alkyl, all of $R^3$, $R^{2'}$, $R^{6'}$ and E represent optionally substituted C1-4 alkyloxycarbonyl, and G represents optionally substituted aryl C1-2 alkyl.

In the compounds represented by formula (XXV) in a further preferred embodiment of the present invention, $R^2$ represents aryl C1-2 alkyl optionally substituted by methoxy or nitro, all of $R^3$, $R^{2'}$, $R^{6'}$ and E represent C1-4 alkyloxycarbonyl optionally substituted by phenyl optionally substituted by methoxy or nitro, and G represents aryl C1-2 alkyl optionally substituted by methoxy.

In the compounds represented by formula (XXV) in another embodiment of the present invention, R² represents benzyl, methoxybenzyl or nitrobenzyl, R³, R²' and R⁶', which may be the same or different, represent methanesulfonyl, benzylsulfonyl, p-toluenesulfonyl, benzyloxycarbonyl, tert-butoxycarbonyl, p-methoxybenzyloxycarbonyl, or p-nitrobenzyloxycarbonyl, E represents benzyloxycarbonyl, and G represents a hydrogen atom, acetyl, benzoyl, benzyl, p-methoxybenzyl, or triphenylmethyl.

In the compounds represented by formula (XXV) in a more preferred embodiment of the present invention, R² represents benzyl, methoxybenzyl or nitrobenzyl, all of R³, R²', R⁶' and E represent benzyloxycarbonyl, and G represents benzyl.

Production Process

In the present invention, for example, the following two production processes may be mentioned as production processes for compounds represented by formula (Ia).

First Production Process

In the first production process according to the present invention, compounds represented by formula (Xa) and formula (Xb) are used as synthetic intermediates.

According to one aspect of the present invention, there is provided a process for producing a compound represented by formula (Ia):

[Chemical formula 8]

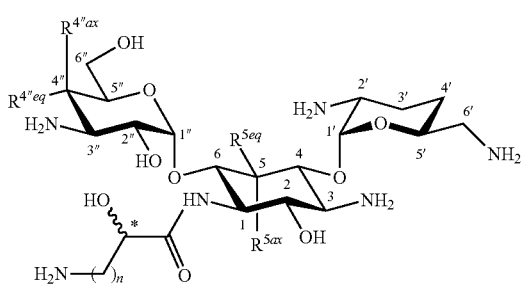

(Ia)

wherein $R^{5ax}$ and $R^{5eq}$, which may be the same or different, represent a hydrogen atom or hydroxyl, $R^{4''ax}$ and $R^{4''eq}$, which may be the same or different, represent a hydrogen atom or hydroxyl, and n is an integer of 1 to 4, the configuration of carbon attached with * represents R or S, the process comprising the steps of introducing protective groups into amino groups in a compound represented by formula (Xa):

[Chemical formula 9]

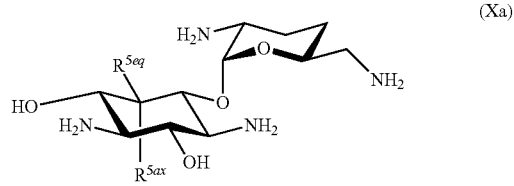

(Xa)

wherein $R^{5ax}$ and $R^{5eq}$ are as defined in formula (Ia), reacting the compound represented by formula (Xa) with a compound represented by formula (Xc):

[Chemical formula 10]

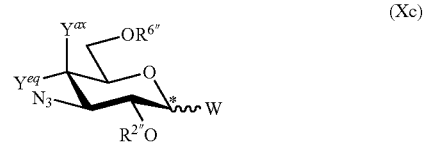

(Xc)

wherein W represents a leaving group; $Y^{ax}$ and $Y^{eq}$, which may be the same or different, represent group —$OR^{4''}$ or a hydrogen atom; $R^{2''}$, $R^{4''}$ and $R^{6''}$ represent a protective group for hydroxyl group, and the configuration of carbon atom attached with * represents R or S, removing the protective groups from the resultant compound and converting an azide group in the compound to an amino group to give a compound represented by formula (Xb):

[Chemical formula 11]

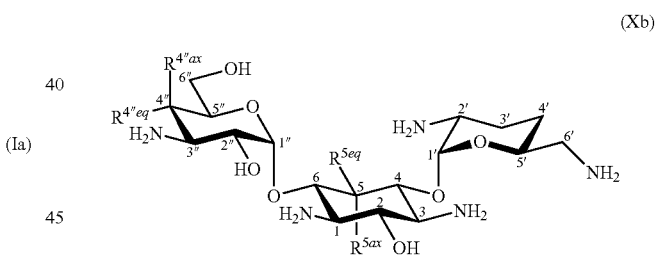

(Xb)

wherein $R^{5ax}$, $R^{5eq}$, $R^{4''ax}$ and $R^{4''eq}$ are as defined in formula (Ia), optionally introducing protective groups into functional groups other than the amino group at 1-position of the compound represented by formula (Xb), reacting the resultant compound with a compound represented by formula (XVII):

[Chemical formula 12]

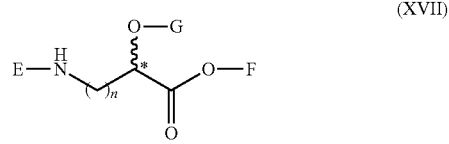

(XVII)

wherein E represents a protective group for amino group; G represents a protective group for hydroxyl group; F represents a hydrogen atom or a carboxylic acid activating group; n is an integer of 1 to 4; and the steric configuration of carbon atom attached with * represents R or S, and removing the protective groups of the resultant compound to give the compound represented by formula (Ia).

In the first production process according to the present invention, the compound represented by formula (XVII) may be an enantiomer mixture with respect to the carbon atom attached with *. Accordingly, according to the first production process of the present invention, a diastereomer mixture with respect to the carbon atom attached with * in the compound represented by formula (Ia) can be produced. The present invention includes this embodiment as well.

In the first production process of the present invention, preferably, hydroxyl exists at 5- and 4"-positions in the compound represented by formula (Ia). Accordingly, in the first production process of the present invention in a preferred embodiment of the present invention, $R^{5ax}$ and $R^{5eq}$, which are different from each other, represent a hydrogen atom or hydroxyl; $R^{4''ax}$ and $R^{4''eq}$, which are different from each other, represent a hydrogen atom or hydroxyl.

According to the first production process of the present invention, in the compound represented by formula (Ia), when hydroxyl exists at 5-position, the steric configuration of the hydroxyl group may be equatorial. Accordingly, in the first production process of the present invention in another preferred embodiment of the present invention, $R^{5ax}$ represents a hydrogen atom, and $R^{5eq}$ represents hydroxyl.

According to the first production process of the present invention, in the compound represented by formula (Ia), when hydroxyl exists at 5-position, the steric configuration of the hydroxyl group may be axial. Accordingly, in the first production process of the present invention in another preferred embodiment of the present invention, $R^{5ax}$ represents hydroxyl, and $R^{5eq}$ represents a hydrogen atom.

In the first production process according to the present invention, preferably, the protective group introduced into the amino group of the compound represented by formula (Xa) is introduced into 1-, 3-, 2'-, and 6'-position of the compound represented by formula (Xa). Such protective groups include, for example, protective groups represented by $R^3$, $R^{2'}$, and $R^{6'}$ in the compound represented by formula (XXV), or protective groups represented by $R^1$, $R^3$, $R^{2'}$, and $R^{6'}$ in scheme 2 which will be described later. More specifically, protective groups introduced into the amino group at 1-, 3-, 2'-, and 6'-positions of the compound represented by formula (Xa) are preferably protective groups commonly used in synthetic organic chemistry, for example, optionally substituted alkylsulfonyl, optionally substituted arylsulfonyl, or optionally substituted alkyloxycarbonyl, more preferably optionally substituted C1-6 alkylsulfonyl, optionally substituted arylsulfonyl, or optionally substituted C1-6 alkyloxycarbonyl, still more preferably C1-6 alkylsulfonyl optionally substituted by optionally substituted phenyl, arylsulfonyl optionally substituted by methyl, or C1-6 alkyloxycarbonyl optionally substituted by optionally substituted phenyl, further preferably C1-3 alkylsulfonyl optionally substituted by optionally substituted phenyl, arylsulfonyl optionally substituted by methyl, or C1-4 alkyloxycarbonyl optionally substituted by optionally substituted phenyl, still further preferably methanesulfonyl, benzylsulfonyl, p-toluenesulfonyl, benzyloxycarbonyl, tert-butoxycarbonyl, p-methoxybenzyloxycarbonyl or p-nitrobenzyloxycarbonyl. More preferred is p-toluenesulfonyl or benzyloxycarbonyl.

The protective group introduced into a functional group other than the amino group at 1-position of the compound represented by formula (Xb) is preferably introduced into the amino group at 2'-, 6'-, and 3"-positions of the compound represented by formula (Xb). The protective group introduced into the 2'- and 6'-positions is the same as the protective group introduced into the 2'- and 6'-positions of the compound represented by formula (Xa). The protective group introduced into the amino group at 3"-position is the same as $R^{3''}$ shown in scheme 3 which will be described later. Such protective groups may be the same as those commonly used in synthetic organic chemistry, preferably optionally substituted alkylcarbonyl, more preferably C1-3 alkylcarbonyl optionally substituted by a halogen atom, still more preferably trifluoroacetyl.

In the compounds represented by formula (Xc), the leaving group represented by W is a halogen atom such as chlorine, bromine or iodine, alkylthio or arylthio, more preferably a halogen atom, C1-3 alkylthio or arylthio, still more preferably bromine or phenylthio.

The protective group for hydroxyl represented by $R^{2''}$ is preferably optionally substituted arylalkyl, more preferably aryl C1-2 alkyl optionally substituted, for example, by nitro, still more preferably benzyl, p-methoxybenzyl, or p-nitrobenzyl, further preferably benzyl.

The protective groups for hydroxyl represented by $R^{4''}$ and $R^{6''}$ may be the same or different, and examples thereof include ester-type protective groups or ether-type protective groups, preferably alkylcarbonyl, arylalkylcarbonyl, or optionally substituted arylalkyl, more preferably C1-6 alkylcarbonyl, aryl C1-3 alkylcarbonyl, or aryl C1-3 alkyl optionally substituted by methoxy, more preferably acetyl, benzoyl, benzyl, p-methoxybenzyl, or triphenylmethyl.

The protective group for hydroxyl group represented by $R^{4''\ and\ R6''}$ together may form a cyclic protective group. The cyclic protective group is preferably C3-8. Specific examples thereof include cyclic protective groups such as acetals or ketals, for example, cyclohexylidene acetal, isopropylidene acetal, or benzylidene acetal.

In the compounds represented by formula (XVII), for example, protective groups presented by formula (XXV) may be mentioned as the protective group for amino group represented by E. More specifically, the protective group for amino represented by E is preferably optionally substituted arylalkyloxycarbonyl, more preferably optionally substituted aryl C1-6 alkyloxycarbonyl, still more preferably aryl C1-6 alkyloxycarbonyl optionally substituted by optionally substituted phenyl, further preferably benzyloxycarbonyl.

The carboxylic acid activation group represented by F is one used for a reaction for forming a peptide bond by activating carboxyl (an active esterification method), preferably a succinimide group, p-nitrophenyl, pentafluorophenyl or 1-hydroxybenzotriazole, more preferably a succinimide group.

Further, the protective group for hydroxyl group represented by G may be, for example, an ester-type protective group or an ether-type protective group, and examples thereof include protective groups represented by formula (XXV). More specifically, the protective group for hydroxyl group represented by G is preferably optionally substituted alkylcarbonyl, optionally substituted arylalkylcarbonyl, or optionally substituted arylalkyl, more preferably optionally substituted C1-6 alkylcarbonyl, optionally substituted arylalkylcarbonyl, or optionally substituted aryl C1-3 alkyl, still more preferably C1-6 alkylcarbonyl; arylcarbonyl; or aryl C1-3 alkyl optionally substituted, for example, by methoxy, further preferably, for example, acetyl, benzoyl, benzyl, p-methoxybenzyl, or triphenylmethyl.

Reaction conditions for each step in the first production process according to the present invention will be described in more detail in (1), (4), and (5) which will be described later.

Second Production Process

In the second production process according to the present invention, in addition to the compounds represented by formula (Xa), the compounds represented by formula (XXV) may be used as the synthetic intermediate. This process is suitable for the production of compounds, of which the steric configuration of the hydroxyl group at 5-position is equatorial, among the compounds represented by formula (Ia).

According to another aspect of the present invention, there is provided a process for producing a compound represented by formula (Ia):

[Chemical formula 13]

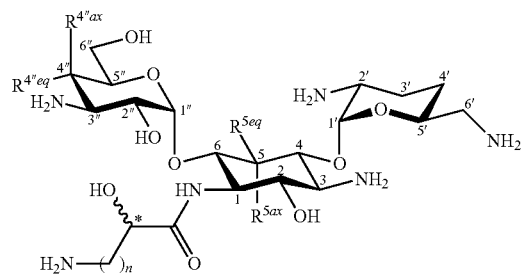

(Ia)

wherein $R^{5ax}$ represents a hydrogen atom, $R^{5eq}$ represents hydroxyl, $R^{4''ax}$ and $R^{4''eq}$, which may be the same or different, represent a hydrogen atom or hydroxyl, n is an integer of 1 to 4, and the steric configuration of carbon atom attached with * represents R or S, the process comprising the steps of introducing protective groups into amino groups at the 3-, 2'- and 6'-positions and a hydroxyl group at 2-position of a compound represented by formula (Xa):

[Chemical formula 14]

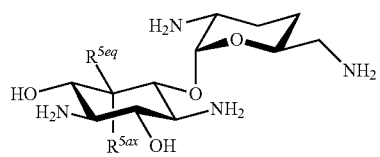

(Xa)

wherein $R^{5ax}$ and $R^{5eq}$ are as defined in formula (Ia), reacting the resultant compound with a compound represented by formula (XVII):

[Chemical formula 15]

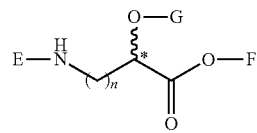

(XVII)

wherein E represents a protective group for amino group; G represents a protective group for hydroxyl group; F represents a hydrogen atom or a carboxylic acid activating group; n is an integer of 1 to 4; and the steric configuration of carbon atom attached with * represents R or S, to give a compound represented by formula (XXV):

[Chemical formula 16]

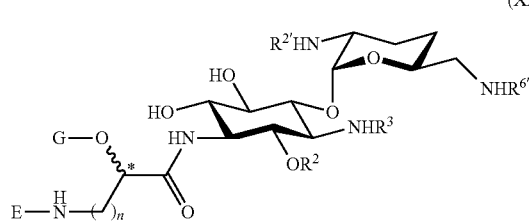

(XXV)

wherein $R^2$ represents a protective group for hydroxyl group; $R^3$, $R^{2'}$ and $R^{6'}$ represent a protective group for amino group, and E, G, n and the steric configuration of the carbon atom attached with * are as defined in formula (XVII), reacting the compound represented by formula (XXV) with a compound represented by formula (Xc) or (Xd):

[Chemical formula 17]

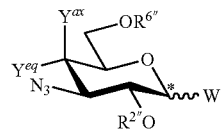

(Xc)

wherein W represents a leaving group; $Y^{ax}$ and $Y^{eq}$, which may be the same or different, represent group —$OR^{4''}$ or a hydrogen atom; $R^{2''}$, $R^{4''}$ and $R^{6''}$ represent a protective group for hydroxyl group; and the steric configuration of carbon atom attached with * represents R or S,

[Chemical formula 18]

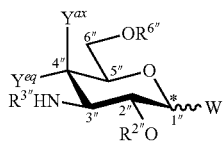

(Xd)

wherein W, $Y^{ax}$, $Y^{eq}$, $R^{2''}$, $R^{6''}$, and the steric configuration of carbon atom attached with * are as defined in (Xc), and $R^{3''}$ represents a protective group for amino group, and removing the protective groups from the resultant compound and, when the compound represented by formula (Xc)

is used, converting an azide group in the compound to an amino group, to give a compound represented by formula (Ia).

In the second production process according to the present invention, the compound represented by formula (XVII) may be an enantiomer mixture with respect to the carbon atom attached with *. Accordingly, according to the second production process of the present invention, a diastereomer mixture with respect to the carbon atom attached with * in the compound represented by formula (Ia) can be produced. The present invention includes this embodiment as well.

In the second production process of the present invention, preferably, hydroxyl exists at 4"-position in the compound represented by formula (Ia). Accordingly, in the second production process of the present invention in a preferred embodiment of the present invention, $R^{4''ax}$ and $R^{4''eq}$, which are different from each other, represent a hydrogen atom or hydroxyl.

In the second production process according to the present invention, specific embodiments of protective groups $R^2$, $R^3$, $R^{2'}$ and $R^{6'}$ introduced into the amino groups at 3-, 2'- and 6-position and the hydroxyl group at 2-position are as described above. Further, W, $Y^{ax}$, $Y^{eq}$, $R^{2''}$ and $R^{6''}$ are the same as those in the first production process.

Reaction conditions for each step in the second production process according to the present invention will be described in detail in (2) and (3) which will be described later.

Production Step of Synthetic Intermediate (Xa)

The compounds represented by formula (Ia) according to the present invention may be synthesized by using the compound represented by formula (II): O-3-deoxy-4-C-methyl-3-(methylamino)-β-L-arabinopyranosyl-(1→6)-O-[2,6-diamino-2,3,4,6-tetradeoxy-α-D-erythro-glucopyranosyl-(1→4)]-D-streptamine (hereinafter referred to as "2-hydroxygentamicin C1a") as one of starting materials for the production of the compounds. The compound represented by formula (II) can be advantageously used as starting materials for the production of compounds represented by formula (Xa) in the above two production processes.

[Chemical formula 19]

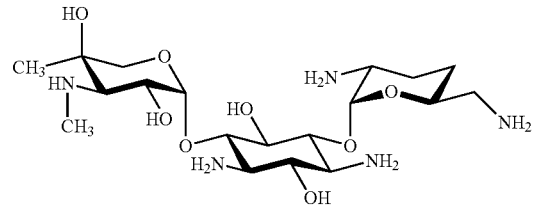

(II)

The compound represented by formula (II) (2-hydroxygentamicin C1a) is a compound obtained by substituting 2-deoxystreptamine, which is a partial constituent element in gentamicin C1a as a gentamicin analogue, by streptamine. This compound may be produced by a conventional method, that is, by adding an analogue of deoxystreptamine to a deoxystreptamine dependent producing strain of an aminoglycoside, culturing the producing strain, and isolating a novel aminoglycoside antibiotic substance which is a substance obtained by substituting a part of the constituent element of the aminoglycoside by the added analogue from the resultant culture. More specifically, the compound represented by formula (II) may be produced by adding streptamine to a deoxystreptamine dependent producing strain of gentamicin C1a and culturing the mixture. Such producing strains include, for example, Micromonospora purpurea ATCC 31119. The above production process is described in detail in Japanese Patent Laid-Open No. 108041/1976 the contents of which are incorporated herein by reference. The process for producing the aminoglycoside antibiotic substance derivative and the method for obtaining a producing strain for use in the production process are described, for example, in Shier, W. T., K. L. Rinehart Jr. & D. Gottlieb et al., Proc. Nat. Acad. Sci. 63: pp. 198 to 204, (1969) in which neomycin is an object compound, and in Kojima M, Sato A et al., J. Antibiot 26 (12): pp. 784-6 (1973) in which ribostamycin and kanamycin are object compounds.

In the production process according to the present invention, when a compound, which is represented by formula (Ia) and of which the hydroxyl group at 5-position is equatorial, is produced, preferably, the compound represented by formula (II) is hydrolyzed to produce a compound represented by formula (Xa). Conditions for hydrolysis are described in detail in the first to sixth steps of scheme 2 which will be described later.

[Chemical formula 20]

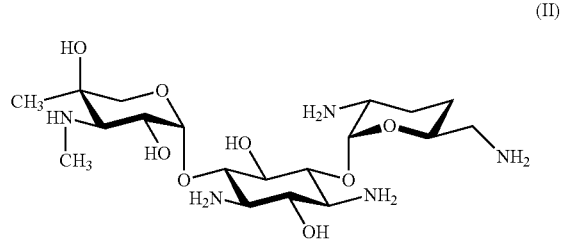

(II)

[Chemical formula 21]

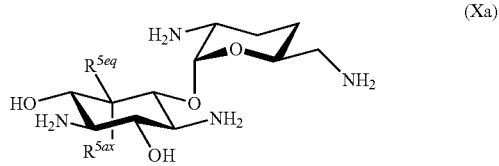

(Xa)

wherein $R^{5ax}$ represents a hydrogen atom; and $R^{5eq}$ represents hydroxyl.

In the production process according to the present invention, when a compound, which is represented by formula (Ia) and of which the steric configuration of the hydroxyl group at 5-position is axial, is produced, the steric configuration of the hydroxyl group at 5-position of the compound represented by formula (II) is inverted. Thus, in another embodiment of the present invention, the process for producing the compound represented by formula (Ia) comprises introducing a protective groups into the hydroxyl groups other than the hydroxyl groups at 4"- and 5-positions, and the amino groups of the compound represented by formula (II), inverting the steric configuration of the hydroxyl group at the 5-position of the resultant compound, removing protective groups of the resultant compound and hydrolyzing the compound to give a compound represented by formula (Xa).

[Chemical formula 22]

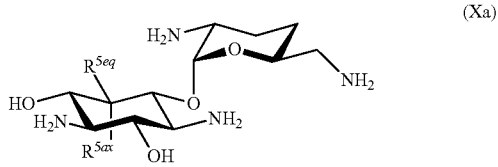

wherein $R^{5ax}$ represents hydroxyl; and $R^{5eq}$ represents a hydrogen atom.

In a preferred embodiment of the present invention, the production process further comprises eliminating the hydroxyl group at the 4"-position before or simultaneously with the inversion of the steric configuration of the hydroxyl group at 5-position. This step is described in detail in step 5-3 to step 5-5 in scheme 10 which will be described later.

The protective groups introduced into the hydroxyl groups other than the hydroxyl group at the 4"- and 5-positions, and the amino groups of the compound represented by formula (II), that is $R^1$, $R^2$, $R^3$, $R^{2'}$, $R^{6'}$, $R^{2''}$, and $R^{3''}$ are as defined above.

The production processes according to the present invention will be classified according to the steric configuration of the hydroxyl groups at 5- and 4"-positions and the type of the production process and will be described in more detail.

(1) Production of Compounds of which 5- and 4"-Positions are Equatorial: First Production Process In the first production process according to the present invention, among the compounds represented by formula (Ia), compounds wherein both $R^{5ax}$ and $R^{4''ax}$ represent a hydrogen atom, both $R^{5eq}$ and $R^{4''eq}$ represent hydroxyl, may be produced according to the following three schemes, that is, scheme 1 (step 1-1 to step 1-5a and step 1-5b), scheme 2 (step 1-6 to step 1-7) and scheme 3 (step 1-8 to step 1-14).

In scheme 1, the process for producing compounds represented by formula (Xc) used in the production process according to the present invention will be specifically described.

[Chemical formula 23]

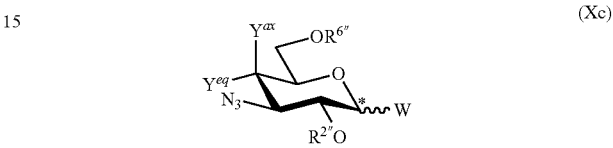

wherein W represents a leaving group; $Y^{ax}$ represents a hydrogen atom; $Y^{eq}$ represents group $-OR^{4''}$; $R^{2''}$, $R^{4''}$ and $R^{6''}$ represent a protective group for hydroxyl group; and the steric configuration of carbon atom attached with * represents R or S.

Scheme 1

Scheme 1 describes step 1-1 to sep 1-5a and step 1-5b. In scheme 1, compounds represented by formula (Xc) are classified into compounds represented by formula (VIII) and compounds represented by formula (IX) according to the type of the leaving group represented by W.

Scheme 1

[Chemical formula 24]

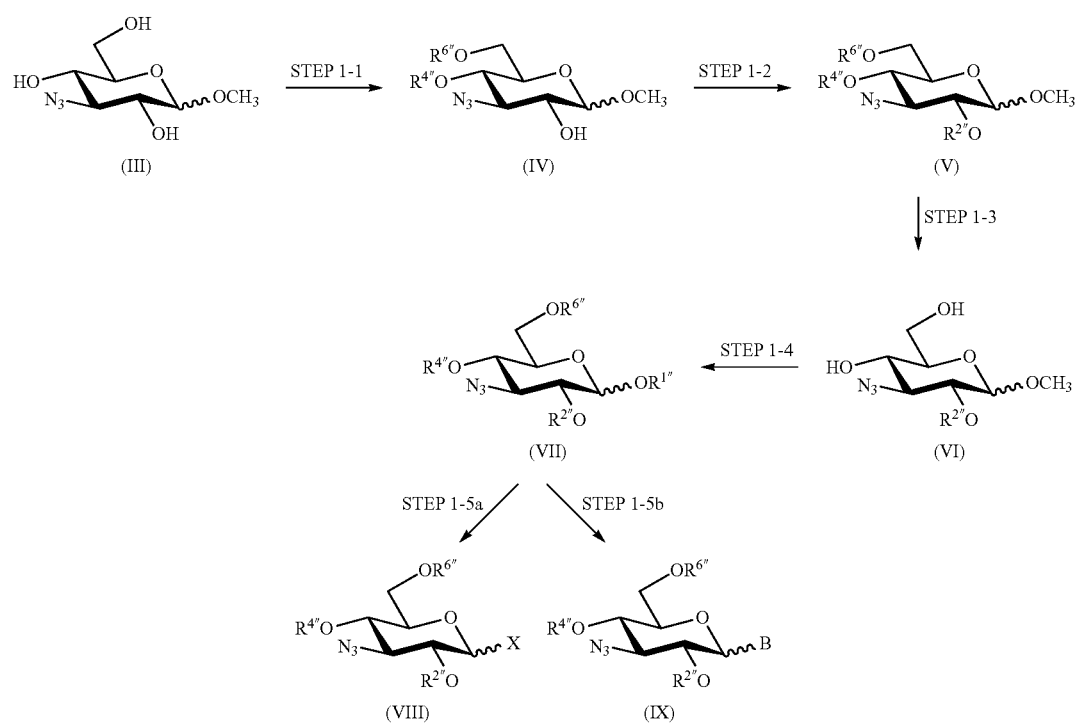

wherein B represents a leaving group containing a sulfur atom such as methylthio, ethylthio, or phenylthio, preferably phenylthio; X represents a halogen atom such as chlorine, bromine or iodine, preferably a bromine atom; $R^{1''}$ represents a protective group for hydroxyl group, preferably, for example, an ester-type protective group such as acetyl or benzoyl, more preferably acetyl; $R^{2''}$ represents a protective group for hydroxyl group, preferably a benzyl-type protective group, which can be removed by a catalytic hydrogen reduction method, such as benzyl, p-methoxybenzyl, or p-nitrobenzyl, more preferably benzyl; and $R^{4''}$ and $R^{6''}$, which may be the same or different, each independently represent a protective group for hydroxyl, for example, an ester-type protective group such as acetyl or benzoyl, or an ether-type protective group such as benzyl, p-methoxybenzyl, or triphenylmethyl, preferably an ester-type protective group such as acetyl or benzoyl, or $R^{4''}$ and $R^{6''}$ together represent a cyclic protective group such as acetal or ketal for simultaneously protecting two hydroxyl groups, for example, cyclohexylidene acetal, isopropylideneacetal, or benzylidene acetal.

Step 1-1

Step 1-1 is a step in which a protective group is introduced into two hydroxyl groups at 4- and 6-positions of the compound represented by formula (III) to give the compound represented by formula (IV). The protective group is an acetal- or ketal-type protective group in which $R^{4''}$ and $R^{6''}$ combine to form one protective group, preferably an isopropylidene group. This step is achieved by reacting the compound represented by formula (III) with a ketone typified by acetone or an acetal typified by 2,2-dimethoxypropane in the presence of an acid.

Solvents usable in this step include, for example, N,N-dimethylformamide, methylene chloride, chloroform, 1,2-dichloroethane, or ethyl acetate. Among them, N,N-dimethylformamide is preferred. Acids usable herein include p-toluenesulfonic acid, pyridinium p-toluene sulfonate, camphor sulfonic acid or hydrochloric acid. Among them, p-toluenesulfonic acid is preferred.

The reaction temperature is in the range of 20° C. to the reflux temperature. The reaction time is, for example, 1 to 24 hr.

In this reaction, for example, when an acetal typified by 2,2-dimethoxypropane is used, a method may also be adopted in which the reaction is carried out while removing the alcohol produced as a by-product by distillation under the reduced pressure from the reaction system to accelerate the reaction.

Step 1-2

Step 1-2 is a step of producing the compound represented by formula (V) by introducing a protective group ($R^{2''}$) into the hydroxyl group at 2-position of the compound represented by formula (IV). This step is achieved by reacting the compound represented by formula (IV) with $R^{2''}$X, wherein $R^{2''}$ represents, for example, benzyl, p-methoxybenzyl or p-nitrobenzyl, and X represents, for example, chlorine, bromine or iodine, in the presence of a base.

Solvents usable in this step include pyridine, N,N-dimethylformamide, tetrahydrofuran, 1,4-dioxane, or methylene chloride. Among them, N,N-dimethylformamide is preferred. Bases usable herein include pyridine, lutidine, collidine, triethylamine, diisopropylethylamine, 4-dimethylaminopyridine, sodium hydride, and potassium hydroxide. Among them, sodium hydride is preferred.

The reaction temperature is −20° C. to 50° C. The reaction time is 1 to 24 hr.

Step 1-3

Step 1-3 is a step of removing the protective group at the 4- and 6-positions of the compound represented by formula (V) to give a compound represented by formula (VI). This step is achieved by reacting the compound represented by formula (V) with an acid.

Solvents usable in this step include tetrahydrofuran, diethyl ether, 1,4-dioxane, methanol, methylene chloride, chloroform, acetic acid, water, or a mixed solvents composed of them. Among them, a mixed solvent composed of acetic acid and water is preferred. Acids usable herein include acetic acid, trifluoroacetic acid, hydrochloric acid, sulfuric acid, p-toluenesulfonic acid, or boron trichloride. Among them, acetic acid is preferred.

The reaction temperature is in the range of 0° C. to the reflux temperature. The reaction time is 0.1 to 12 hr.

Step 1-4

Step 1-4 is a step of introducing a protective group into each of the hydroxyl group at the 4- and 6-positions of the compound represented by formula (VI) and converting the methoxy group at the 1-position of the compound represented by formula (VI) to an acyloxy group to give a compound represented by formula (VII).

This step can be achieved, for example, by simultaneously reacting a carboxylic acid represented by $R^{1''}OH$ such as acetic acid and an acid anhydride represented by $R^{4''}{}_2O$ (or $R^{6''}{}_2O$) such as acetic anhydride with the compound represented by formula (VI) in the presence of an acid catalyst.

Solvents usable in the above step include, for example, methylene chloride, chloroform, 1,2-dichloroethane, acetic acid, acetic anhydride, or a mixed solvent composed of them. Among them, a mixed solvent composed of acetic acid and acetic anhydride is preferred. Acids usable herein include hydrogen chloride or sulfuric acid. Preferred is sulfuric acid.

The reaction temperature is −20° C. to 50° C. The reaction time is 1 to 24 hr.

Step 1-4 can be carried out in two divided steps. In this case, at the outset, a first step of introducing protective groups into the hydroxyl groups at the 4- and 6-positions is carried out, and a second step of converting the methoxy group at the 1-position to the acyloxy group is carried out.

The first step is carried out by reacting a compound represented by formula (VI) with an acid anhydride such as acetic anhydride or an acid halide such as acetyl chloride in the presence of a base. Solvents usable herein include, for example, pyridine, N,N-dimethylformamide, methylene chloride, chloroform, or 1,2-dichloroethane. Among them, pyridine is preferred. Bases usable herein include triethylamine, pyridine, or 4-dimethylaminopyridine. Among them, pyridine is preferred. The reaction temperature is −20° C. to 50° C. The reaction time is 1 to 24 hr.

In the second step, the compound produced in the first step is reacted with a carboxylic acid represented by $R^{1''}OH$ such as acetic acid and an acid anhydride represented by $R^{1''}{}_2O$ such as acetic anhydride in the presence of an acid catalyst. Solvents usable in the second step include methylene chloride, chloroform, 1,2-dichloroethane, acetic acid, acetic anhydride, or a mixed solvent composed of them. Among them, a mixed solvent composed of acetic acid and acetic anhydride is preferred. Acids usable herein include hydrogen chloride or sulfuric acid. Preferred is sulfuric acid.

The reaction temperature is −20° C. to 50° C. The reaction time is 1 to 24 hr.

Step 1-5a

Step 1-5a is a step of converting the acyloxy group (OR$^{1''}$) at 1-position of the compound represented by formula (VII) to a halogen atom to give a compound represented by formula (VIII). This step is achieved by reacting the compound represented by formula (VII) with a hydrogen halide represented by HX or a titanium halide represented by TiX$_4$ wherein X represents a chlorine atom or a bromine atom.

Solvents usable in this step include methylene chloride, chloroform, 1,2-dichloroethane, ethyl acetate, or a mixed solvent composed of them. Among them, a mixed solvent composed of methylene chloride and ethyl acetate is preferred.

The reaction temperature is −20° C. to 50° C. Further, the reaction time is 1 to 24 hr.

Step 1-5b

Step 1-5b is a step of converting the acyloxy group (OR$^{1''}$) at 1-position of the compound represented by formula (VII) to thioalkyl or thioaryl in the presence of a Lewis acid to give a compound represented by formula (IX). Specifically, this step is achieved by reacting the compound represented by formula (VII) with a thiol represented by BH, wherein B represents, for example, methylthio, ethylthio, or phenylthio, or a trimethylsilylated thiol represented by TMS-B, wherein TMS represents trimethylsilyl, and B is as defined above, in the presence of a Lewis acid.

Solvents usable in this step include, for example, methylene chloride, chloroform, 1,2-dichloroethane, ethyl acetate, or a mixed solvent composed of them. Among them, methylene chloride is preferred. Lewis acids usable herein include trimethylsilyltriflate or tin chloride. Preferred is trimethylsilyltriflate. The reaction temperature is in the range of 20° C. to the reflux temperature. The reaction time is 1 to 48 hr.

All the substituents at 1-position of the compound shown in scheme 1 can take two steric configurations, that is, an axial form and an equatorial form. In scheme 1, these two steric configurations may be separated from each other before use in the reaction, or alternatively the two steric configurations in a mixed form as such may be used in the reaction. Further, the compound represented by formula (VIII) and the compound represented by formula (IX) produced in scheme 1 may be separated into an axial form and an equatorial form which are then used separately from each other in scheme 3. Alternatively, these compounds may be used as a mixture of the axial form with the equatorial form.

Next, a process for producing a compound represented by formula (Xa) comprising step 1-6 and step 1-7 will be described in detail according to scheme 2. In scheme 2, the compound represented by formula (Xa) in which the steric configuration of the hydrogen atom at 5-position is equatorial corresponds to the compound represented by formula (X).

[Chemical formula 25]

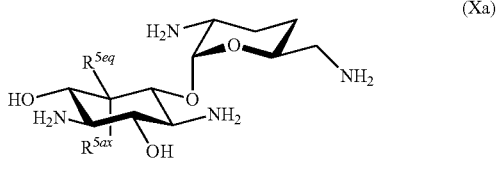

wherein R$^{5ax}$ represents a hydrogen atom; and R$^{5eq}$ represents hydroxyl.

Scheme 2

[Chemical formula 26]

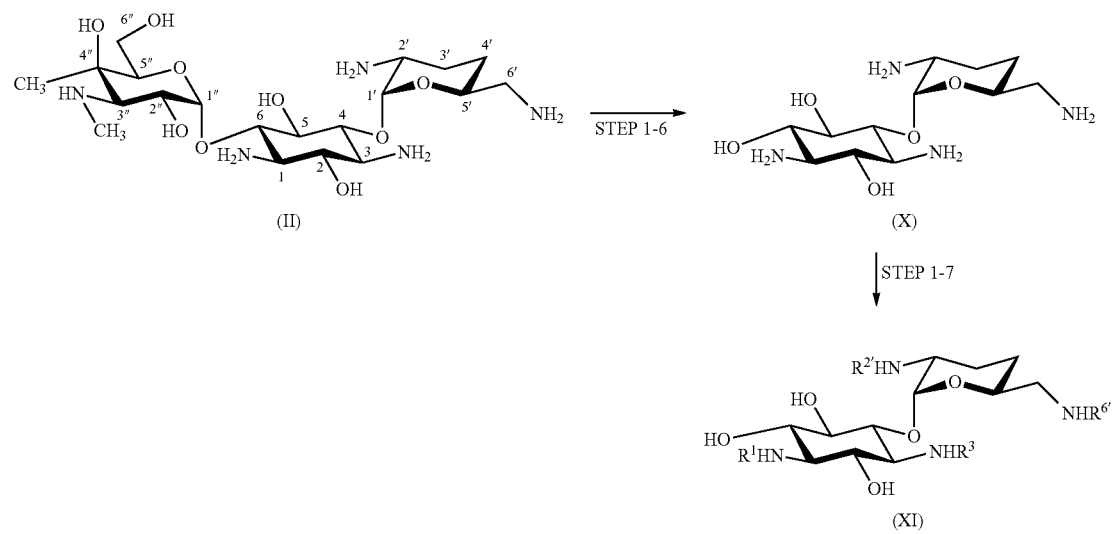

wherein

R¹, R³, R²' and R⁶' represents a protective group for amino group, preferably a protective group commonly used in organic synthetic chemistry such as methanesulfonyl, benzylsulfonyl, p-toluenesulfonyl, benzyloxycarbonyl, tert-butoxycarbonyl, p-methoxybenzyloxycarbonyl, or p-nitrobenzyloxycarbonyl, more preferably p-toluenesulfonyl or benzyloxycarbonyl.

Step 1-6

Step 1-6 is a step for hydrolyzing the compound represented by formula (II) (2-hydroxygentamicin C1a) as a starting compound to give a compound represented by formula (X). This step is achieved by heating the compound represented by formula (II) in the presence of an acid.

In the above step, water is preferably used as a solvent. Acids usable herein include hydrochloric acid, sulfuric acid, nitric acid or hydrobromic acid. Among them, 3 to 5 M hydrochloric acid is preferred.

The reaction temperature is in the range of 20° C. to the reflux temperature. The reaction time is 0.5 to 24 hr.

Step 1-7

Step 1-7 is a step of introducing protective groups into four amino groups in the compound represented by formula (X) to give a compound represented by formula (XI). This step can be achieved by reacting the compound represented by formula (X) with a chloroformic ester such as benzyl chloroformate, p-methoxybenzyl chloroformate, or p-nitrobenzyl chloroformate, a carbonic diester such as di-tert-butyl dicarbonate, or a sulfonylating agent such as methanesulfonyl chloride, benzylsulfonyl chloride, or p-toluenesulfonyl chloride in the presence of a base.

Solvents usable in this step include water, N,N-dimethylformamide, tetrahydrofuran, 1,4-dioxane, acetone, or a mixed solvent composed of them. Among them, a mixed solvent composed of water and 1,4-dioxane is preferred. Bases usable herein include sodium hydroxide, potassium carbonate, sodium carbonate, triethylamine, pyridine, or 4-dimethylaminopyridine. Preferred is sodium carbonate.

The reaction temperature is −20° C. to 50° C., and the reaction time is 1 to 24 hr.

The first production process according to the present invention will be described in more detail according to scheme 3 which shows step 1-8 to step 1-14. In scheme 3, the compound represented by formula (Ia) is finally synthesized through a compound represented by formula (XIV) which is a key intermediate of the compound represented by formula (Ia).

Scheme 3

[Chemical formula 27]

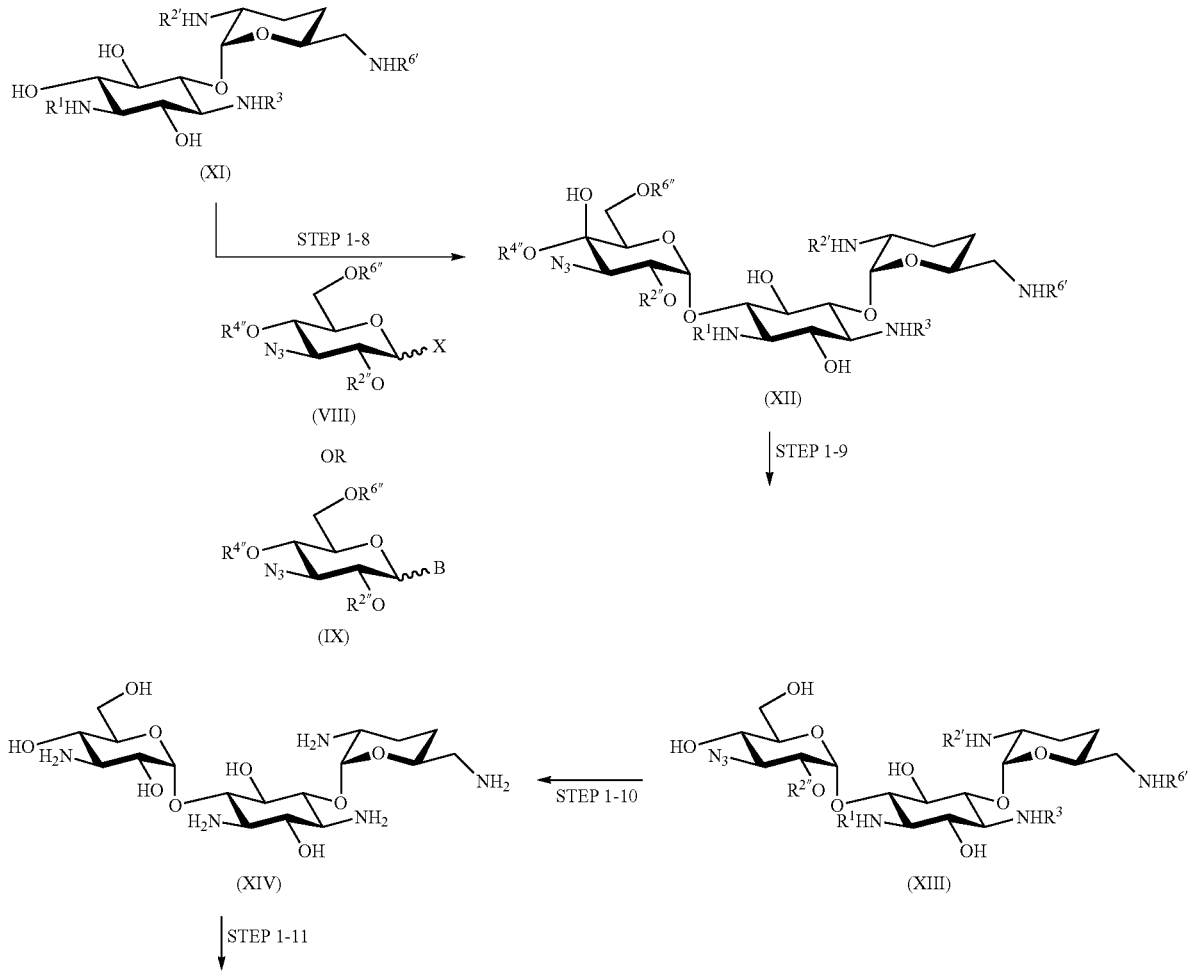

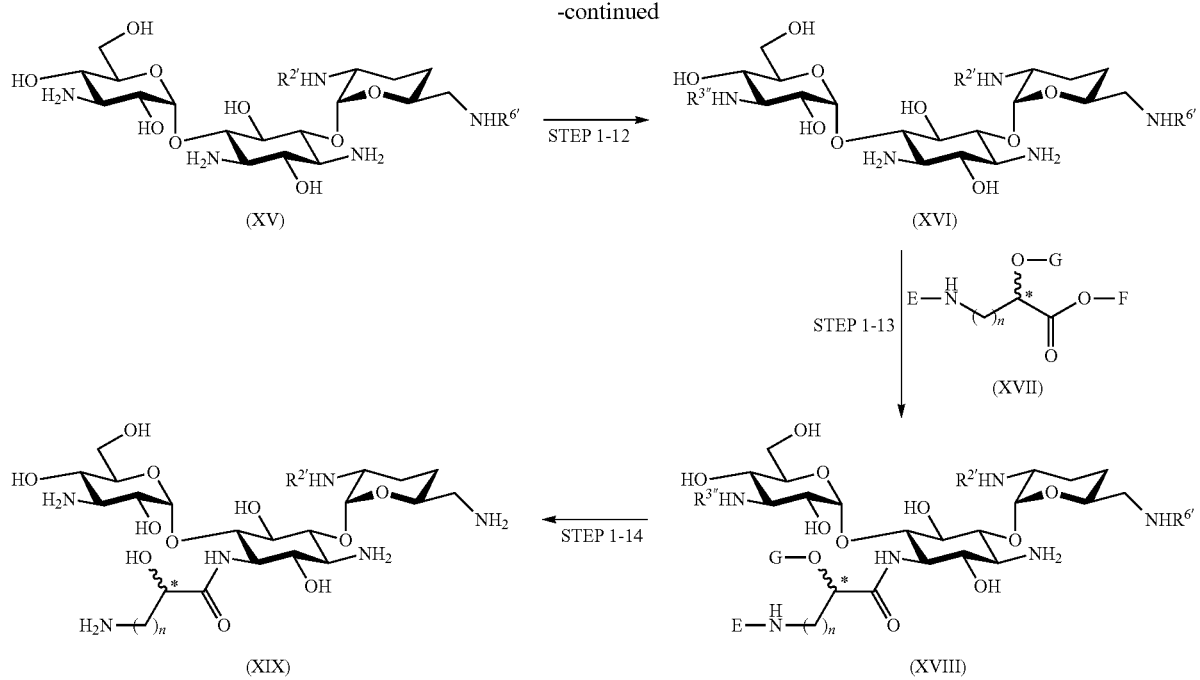

wherein

B, X, $R^1$, $R^3$, $R^{2'}$, $R^{6'}$, $R^{2''}$, $R^{4''}$, $R^{6''}$, n, and the steric configuration of carbon atom attached with * are as described in schemes 1 and 2, E represents a protective group for amino, preferably a protective group for amino group commonly used in organic synthetic chemistry, more preferably benzyloxycarbonyl, F represents a hydrogen atom or a carboxylic acid activation group used in a reaction which activates carboxyl to form a peptide bond (an active esterification method), preferably a succinimide group, p-nitrophenyl, pentafluorophenyl, or 1-hydroxybenzotriazole, more preferably succinimide group, G represents a hydrogen atom or a protective group for hydroxyl group, for example, an ester-type protective group such as acetyl or benzoyl, or an ether-type protective group such as benzyl, p-methoxybenzyl, or triphenylmethyl, and $R^{3''}$ represents a protective group for amino group, preferably a protective group for amino group commonly used in organic synthetic chemistry, more preferably trifluoroacetyl.

Step 1-8

Step 1-8 is a step of condensing the hydroxyl group at 6-position of the compound represented by formula (XI) with the compound represented by formula (VIII) produced in step 1-5a or the compound represented by formula (IX) produced in step 1-5b to give a compound represented by formula (XII). This step can be achieved by reacting the compound represented by formula (XI) with the compound represented by formula (VIII) or formula (IX) in the presence of a catalyst and a dehydrating agent.

Solvents usable in this step include, for example, N,N-dimethylformamide, methylene chloride, chloroform, 1,2-dichloroethane, diethyl ether, or ethyl acetate, preferably 1,2-dichloroethane. Catalysts usable herein include trifluoromethanesulfonic acid, mercuric cyanide, N-iodosuccinimide, trifluoroacetic acid, mercury bromide, or yellow mercury oxide. Preferred is mercuric cyanide. Dehydrating agents usable herein include, for example, molecular sieves 4 A or Drierite, preferably Drierite.

The reaction temperature is −20° C. to 60° C. The reaction time is 1 to 24 hr.

When X in formula (VIII) produced in step 1-5a is a bromine atom, the step may be carried out by applying a conventional glycosylation reaction using a brominated succharide donor called a Koenigs-Knorr's glycosylation reaction (Chem. Ber., Vol. 34, p. 957 (1901)). Conditions for this reaction may be properly determined by reference to a review of H. Paulsen et al. (Angew. Chem. Int. Ed. Engl., Vol. 21, pp. 155-173 (1982)), a review of R. R. Schmidt (Angew. Chem. Int. Ed. Engl., Vol. 25, pp. 212-235 (1986)) and the like.

On the other hand, when B in formula (IX) produced in step 1-5b is thiophenyl, the step may be carried out by reference to a report of G. H. Veeneman et al. (Tetrahedron Letters, Vol. 31, pp. 1331-1334 (1990)), a report of P. Konradsson et al. (Tetrahedron Letters, Vol. 31, pp. 4313-4316 (1990)) and the like.

Step 1-9

Step 1-9 is a step of removing the protective group ($R^{4''}$) at 4"-position and the protective group ($R^{6''}$) at 6"-position of the compound represented by formula (XII) to give a compound represented by formula (XIII). This step can be achieved by reacting the compound represented by formula (XII) with a base.

Solvents usable in this step include methanol, ethanol, isopropyl alcohol, tert-butyl alcohol, methylene chloride, chloroform, or a mixed solvent composed of them. Among them, methanol is preferred. Bases usable herein include potassium carbonate, sodium carbonate, potassium hydroxide, sodium hydroxide, sodium methoxide, sodium ethoxide, or tert-BuOK. Preferred is sodium methoxide.

The reaction temperature is −20° C. to 60° C., and the reaction time is 1 to 24 hr.

Step 1-10

Step 1-10 is a step of producing the compound represented by formula (XIV) as the key intermediate. The compound represented by formula (XIV) constitutes a basic skeleton of the compound represented by formula (Ia). Accordingly, the compound represented by formula (XIV) may be used as an intermediate for the production of the compound represented by formula (Ia) and its derivatives, and the present invention includes this embodiment.

In step 1-10, all the protective groups in the compound represented by formula (XIII) are removed, and, further, the azido group at 3"-position is converted to amino to give a compound represented by formula (XIV). This step can be achieved by radically reacting the compound represented by formula (XIII) with an alkali metal to remove the protective groups for all the amino groups and a hydroxyl group at 2"-position, and converting the azido group at 3"-position to amino group, that is, by adopting the so-called "Birch reduction conditions."

Solvents usable in the above step include liquid ammonia, methylamine, ethylamine, hexamethylphosphoamide, diethyl ether, tetrahydrofuran, or a mixed solvent composed of them, preferably liquid ammonia. Alkali metals usable herein include lithium, sodium, or potassium, preferably sodium.

The reaction temperature is −60° C. to 20° C., and the reaction time is 0.5 to 24 hr.

When the protective group for amino group in the compound represented by formula (XIII) is a protective group which can be removed by a catalytic hydrogen reduction reaction, for example, benzyloxycarbonyl, p-methoxybenzyloxycarbonyl, or p-nitrobenzyloxycarbonyl, the above step can also be carried out by reacting the compound represented by formula (XIII) with hydrogen in the presence of a catalytic hydrogen reduction catalyst. Catalytic hydrogen reduction catalysts usable herein include palladium-carbon, palladium black, palladium hydroxide, and platinum oxide. Among them, palladium-carbon is preferred. In the reaction, any solvent may be used without particular limitation so far as the solvent is not involved in the reaction. Preferred are methanol, ethanol, tetrahydrofuran, 1,4-dioxane, a mixed solvent composed of them, or a mixed solvent composed of the above organic solvent and water.

The reaction temperature is 10° C. to 30° C. The reaction time is generally 1 to 8 hr.

When the protective group for amino in the compound represented by formula (XIII) is tert-butoxycarbonyl, a method may also be adopted in which the compound represented by formula (XIII) is reacted with hydrogen in the presence of a catalytic hydrogen reduction catalyst to remove the protective group for hydroxyl group at 2"-position and to convert the azido group at 3"-position to amino group, followed by a reaction of the resultant compound with an acid to remove tert-butoxycarbonyl. In this case, solvents usable for removing the protective group for amino group include ethyl acetate, methylene chloride, acetonitrile, acetone, anisole, water, or a mixed solvent composed of them. Among them, water is preferred. Acids usable herein include p-toluenesulfonic acid, methanesulfonic acid, acetic acid, or trifluoroacetic acid, preferably trifluoroacetic acid.

The reaction temperature is generally 0° C. to 30° C. The reaction time is 1 to 12 hr.

Step 1-11

Step 1-11 is a step of selectively introducing protective group ($R^{2'}$ and $R^{6'}$) into the amino groups at 2' and 6'-positions of the compound represented by formula (XIV) to give a compound represented by formula (XV). This step can be achieved by the compound represented by formula (XIV) with a chloroformic ester such as benzyl chloroformate, p-methoxybenzyl chloroformate, or p-nitrobenzyl chloroformate, a carbonic diester such as di-tert-butyl dicarbonate, or an N-(benzyloxycarbonyloxy)succinimide in the presence of a metal salt.

Solvents usable in this step include, for example, N,N-dimethylformamide, dimethylsulfoxide, methanol, ethanol, or isopropyl alcohol, preferably methanol. Transition metal salts usable herein include zinc acetate, nickel acetate, or cobalt acetate, preferably nickel acetate.

The reaction temperature is −20° C. to 50° C., and the reaction time is 1 to 24 hr.

Step 1-12

Step 1-12 is a step of selectively introducing a protective group ($R^{3''}$) into the amino group at 3"-position of the compound represented by formula (XV) to give a compound represented by formula (XVI). This step can be achieved by reacting the compound represented by formula (XV), for example, with a halogenated carboxylic anhydride such as trifluoroacetic anhydride or trichloroacetic anhydride, a halogenated carboxylic ester such as methyl trifluoroacetate or ethyl trifluoroacetate, or an acid halide of a halogenated carboxylic acid.

In the above step, preferred reactants usable herein include ethyl trifluoroacetate.

Solvents usable in this step include, for example, N,N-dimethylformamide, dimethylsulfoxide, tetrahydrofuran, or 1,4-dioxane, preferably N,N-dimethylformamide.

The reaction temperature is −20° C. to 50° C., and the reaction time is 1 to 24 hr.

Step 1-13

Step 1-13 is a step of reacting the amino group at 1-position of the compound represented by formula (XVI) with an ω-amino-α-hydroxycarboxylic acid derivative represented by formula (XVII) to give a compound represented by formula (XVIII), that is, a step of conducting a peptide bond forming reaction. The compound represented by formula (XVII) is, for example, a 4-amino-2-hydroxybutyric acid derivative which can be prepared by conventional organic synthesis using a proper starting compound. Alternatively, the compound may be synthesized by reference to the process reported by H. Kawaguchi et al. (Journal of Antibiotics, Vol. 25, pp. 695-708 (1972)). In this step, when a compound represented by formula (XVII) wherein F represents a hydrogen atom is used, a peptide condensing agent commonly used in organic synthesis is used. Peptide condensing agents include, for example, dicyclohexylcarbodiimide, diisopropylcarbodiimide, N-ethyl-N'-dimethyl aminopropylcarbodiimide and its hydrochloride, benzotriazol-1-yl-tris(dimethylamino)phosphonium hexafluorophosphide, and diphenylphosphorylazide. They may be used solely, or alternatively may be used in combination with N-hydroxysuccinimide, 1-hydroxybenzotriazole or the like. When a reaction which activates the carboxyl group to form a peptide bond (an active esterification method) is used, in formula (XVII), F represents a carboxylic acid activation group selected from a succinimide group, p-nitrophenyl, pentafluorophenyl, 1-hydroxybenzotriazole or the like. That is, a compound called "active ester" is formed. In some cases, this active ester is isolated before use.

Solvents usable in the above step include N,N-dimethylformamide, dimethylsulfoxide, tetrahydrofuran, or 1,4-dioxane. Among them, tetrahydrofuran is preferred.

The reaction temperature is −20° C. to 50° C., and the reaction time is 1 to 48 hr.

Step 1-14

Step 1-14 is a step of removing the protective group in the compound represented by formula (XVIII) to give a compound represented by formula (Ia) wherein both $R^{ax}$ and $R^{4''ax}$ represent a hydrogen atom; and both $R^{5eq}$ and $R^{4''eq}$ represent hydroxyl. This step can be achieved by reacting the compound represented by formula (XVIII) with a base to remove the protective group for amino group at 3''-position and then reacting the resultant compound with hydrogen in the presence of a catalytic hydrogen reduction catalyst to remove the remaining protective group for amino group.

Solvents usable in the above step of removing the protective group for amino at the 3''-position include methanol, ethanol, isopropyl alcohol, tert-butyl alcohol, tetrahydrofuran, 1,4-dioxane, water, or a mixed solvent composed of them. Among them, a mixed solvent composed of tetrahydrofuran and water is preferred. Bases usable herein include aqueous ammonia, potassium carbonate, sodium carbonate, potassium hydroxide, or sodium hydroxide. Among them, aqueous ammonia is preferred.

The reaction temperature is 0° C. to 50° C., and the reaction time is 1 to 48 hr.

Catalytic hydrogen reduction catalysts usable in the step of removing the remaining protective group for amino group other than the amino group at 3''-position include palladium-carbon, palladium black, palladium hydroxide, Raney nickel, or platinum oxide. Among them, palladium black is preferred. Any solvent may be used without particular limitation so far as the solvent is inert to the reaction. Preferred solvents include methanol, ethanol, tetrahydrofuran, 1,4-dioxane, acetic acid, a mixed solvent composed of them, or a mixed solvent composed of the organic solvent and water. A hydrogen gas may be used as hydrogen added. The pressure of the hydrogen gas may be 1 atom which is the atmospheric pressure. If necessary, a pressurized hydrogen gas may also be used. Regarding hydrogen sources different from the hydrogen gas, if necessary, formic acid, a salt of formic acid, cyclohexene or the like may also be used.

The reaction temperature is 10° C. to 30° C., and the reaction time is generally 1 to 8 hr.

When the protective group for amino group in the compound represented by formula (XVIII) is, for example, tert-butoxycarbonyl or p-methoxybenzyloxycarbonyl which can be removed under acidic conditions, the remaining protective group for amino group other than the amino group at 3''-position may also be removed by reacting the compound, produced by removing the protective group for amino at 3''-position, with a acid. In this case, solvents usable in the step of removing the protective group for amino group include ethyl acetate, methylene chloride, acetonitrile, acetone, anisole, water, or a mixed solvent composed of them. Among them, water is preferred. Acids usable herein include p-toluenesulfonic acid, methanesulfonic acid, acetic acid, or trifluoroacetic acid. Among them, trifluoroacetic acid is preferred.

The reaction temperature is generally 0° C. to 30° C., and the reaction time is 1 to 12 hr.

(2) Production of Compounds of which the 5- and 4''-Positions are Equatorial: Second Production Process In the second production process according to the present invention, among the compounds represented by formula (Ia), compounds wherein both $R^{5ax}$ and $R^{4''ax}$ represent a hydrogen atom and both $R^{5eq}$ and $R^{4''eq}$ represent hydroxyl, may be produced according to the following scheme 4 (step 2-1 to step 2-7), scheme 5 (step 2-8 to step 2-10). In this case, the starting compound (X) is the same as the compound synthesized from the compound represented by (2-hydroxygentamicin C1a) represented by formula (II) in scheme 2.

Scheme 4

[Chemical formula 28]

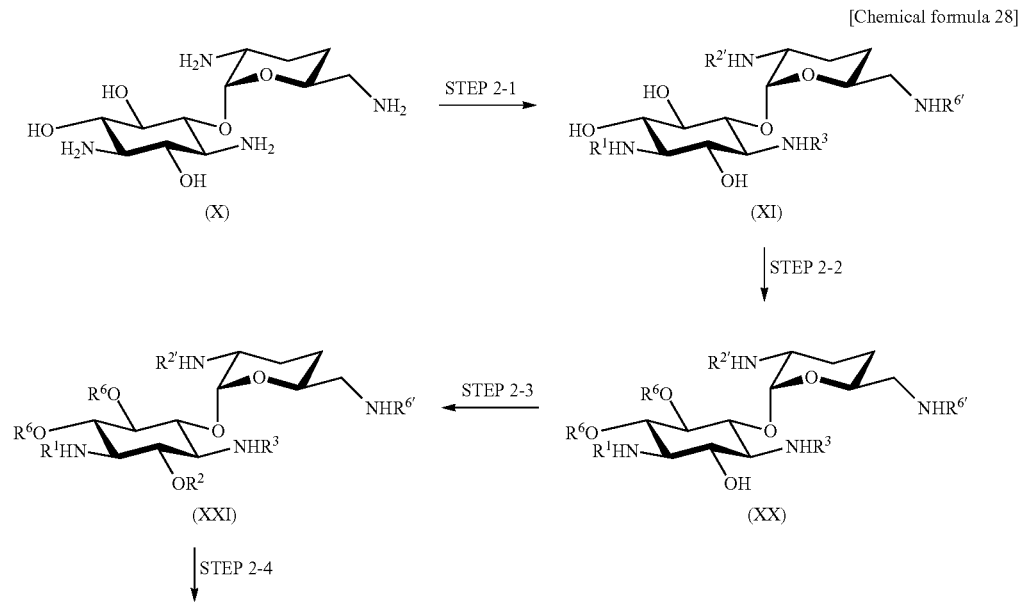

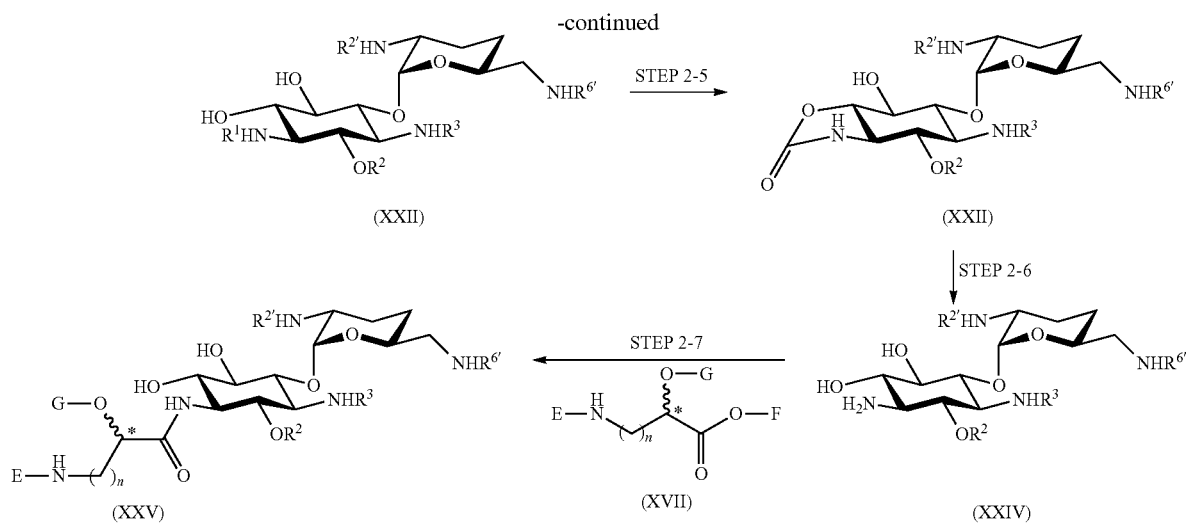

wherein
$R^1, R^3, R^{2'}, R^{6'}, E, F, G, n$, and the steric configuration of the carbon atom attached with * are as defined in schemes 1 and 2; $R^2$ represents a protective group for hydroxyl group commonly used in organic synthesis, preferably a benzyl-type protective group which can be removed by a catalytic hydrogen reduction reaction such as benzyl, p-methoxybenzyl, or p-nitrobenzyl, more preferably benzyl; $R^5$ and $R^6$ represent a protective group for hydroxyl group and each independently represent a protective group for hydroxyl group, or $R^5$ and $R^6$ together represent a cyclic protective group which simultaneously protects two hydroxyl groups, for example, an acetal or a ketal, preferably cyclohexylidene acetal.

In scheme 4, step 2-1 to step 2-6 are steps of introducing a protective group into the amino groups at 3, 2' and 6'-positions and the hydroxyl group at 2-position of the compound represented by formula (X).

Step 2-1

Step 2-1 is a step of introducing an identical protective group into four amino groups in the compound represented by formula (X) synthesized in scheme 2 to give a compound represented by formula (XI). This step can be achieved by reacting the compound represented by formula (X) with a chloroformic ester such as benzyl chloroformate, p-methoxybenzyl chloroformate, or p-nitrobenzyl chloroformate, a carbonic diester such as di-tert-butyl dicarbonate, or N-(benzyloxycarbonyloxy)succinimide in the presence of a base.

Solvents usable in this step include, for example, 1,2-dimethoxyethane, N,N-dimethylformamide, dimethylsulfoxide, methanol, ethanol, isopropyl alcohol, tetrahydrofuran, 1,4-dioxane, diethyl ether, methylene chloride, chloroform, and water. They may be mixed together for use as a mixed solvent. A mixed solvent composed of 1,2-dimethoxyethane or 1,4-dioxane and water is preferred. Bases usable herein include organic bases such as triethylamine, diisopropylethylamine, N-methylmorpholine, and pyridine, and inorganic bases such as sodium carbonate, potassium carbonate, and sodium hydrogencarbonate. Among them, triethylamine is preferred.

The reaction temperature is −20° C. to 50° C., and the reaction time is 1 to 24 hr.

Step 2-2

Step 2-2 is a step of introducing protective groups ($R^5$ and $R^6$) into the hydroxyl group adjacent to 5- and 6-positions of the compound represented by formula (XI) to give a compound represented by formula (XX). The protective group for hydroxyl to be selected may be such that $R^5$ and $R^6$ each independently serve as a protective group for hydroxyl group. The protective group for hydroxyl group is preferably such that $R^5$ and $R^6$ together form a cyclic protective group. Such protective groups include cyclohexylidene acetal, isopropylideneacetal, and benzylidene acetal. In this scheme, cyclohexylidene acetal is preferred.

Solvents usable in this step include, for example, N,N-dimethylformamide, methylene chloride, chloroform, 1,2-dimethoxyethane, 1,2-dichloroethane, ethyl acetate, or a mixed solvent composed of them. Among them, 1,2-dimethoxyethane is preferred. Acids usable herein include p-toluenesulfonic acid, pyridinium p-toluene sulfonate, camphor sulfonic acid, or hydrochloric acid. Among them, pyridinium p-toluene sulfonate is preferred.

The reaction temperature is in the range of 20° C. to the reflux temperature, and the reaction time is, for example, 1 to 24 hr.

In this reaction, when an acetal such as 2,2-dimethoxypropane or cyclohexanone dimethylacetal is used, the reaction may be carried out while removing the alcohol as a by-product from the reaction system by distillation under the reduced pressure to accelerate the reaction.

Step 2-3

Step 2-3 is a step of introducing a protective group ($R^2$) into the hydroxyl group at 2-position of the compound represented by formula (XX) to give a compound represented by formula (XXI). This step can be achieved by reacting the compound represented by formula (XX) with $R^2$—X, wherein $R^{2'''}$ represents benzyl, p-methoxybenzyl, or p-nitrobenzyl, and X represents chlorine, bromine, iodine or the like, in the presence of a base.

Solvents usable in this step include pyridine, N,N-dimethylformamide, tetrahydrofuran, 1,4-dioxane, or methylene chloride. Among them, N,N-dimethylformamide and tetrahydrofuran are preferred. Bases usable herein include pyridine, lutidine, collidine, triethylamine, diisopropylethylamine, 4-dimethylaminopyridine, sodium hydride, or potassium hydroxide. Among them, sodium hydride is preferred.

In this reaction, for example, iodides such as sodium iodide and tetrabutylammonium iodide, silver salts such as silver oxide or silver nitrate, or crown ether may be added from the viewpoint of accelerating the reaction.

The reaction temperature is −20° C. to 50° C., and the reaction time is 1 to 24 hr.

Step 2-4

Step 2-4 is a step of removing the protective groups for hydroxyl group in $R^5$ and $R^6$ introduced in the step 2-3 to give a compound represented by formula (XXII). Reaction conditions used are those commonly used in organic synthesis depending upon the protective groups introduced into $R^5$ and $R^6$.

When the protective group for hydroxyl is such that $R^5$ and $R^6$ in formula (XXI) together form a cyclic protective group, this step can be achieved by reacting the compound represented by formula (XXI) with an acid.

Solvents usable in this step include tetrahydrofuran, diethyl ether, 1,4-dioxane, methanol, methylene chloride, chloroform, acetic acid, water, or a mixed solvent composed of them. Among them, a mixed solvent composed of chloroform and methanol or a mixed solvent composed of acetic acid and water is preferred. Acids usable herein include acetic acid, trifluoroacetic acid, hydrochloric acid, sulfuric acid, p-toluenesulfonic acid, or boron trichloride. Among them, trifluoroacetic acid or acetic acid is preferred.

The reaction temperature is in the range of 0° C. to the reflux temperature. The reaction time is 0.1 to 12 hr.

Step 2-5

Step 2-5 is a step of removing the protective group ($R^1$) for amino group at 1-position of the compound represented by formula (XXI) and, at the same time, forming a cyclic carbamate between the amino group and an adjacent hydroxyl group at 6-position to give a compound represented by formula (XXIII).

This step is achieved by treating the compound represented by formula (XXI) with a base. Bases usable herein include sodium hydride and potassium hydroxide. Among them, sodium hydride is preferred. Solvents usable herein include N,N-dimethylformamide, tetrahydrofuran, 1,4-dioxane, or methylene chloride. Among them, N,N-dimethylformamide is preferred.

Step 2-6

Step 2-6 is a step of cleaving the cyclic carbamate formed between 1- and 6-position of the compound represented by formula (XXIII) to give a compound represented by formula (XXIV). This step can be achieved by treating the compound represented by formula (XXIII) with a base.

Bases usable herein include inorganic bases such as sodium carbonate and potassium carbonate, and metal alkoxides such as sodium methoxide and sodium ethoxide.

Solvents usable herein include N,N-dimethylformamide, tetrahydrofuran, 1,4-dioxane, methylene chloride, water, and a mixed solvent composed of them. Among them, a mixed solvent composed of 1,4-dioxane and water is preferred.

The reaction temperature is in the range of 0° C. to the reflux temperature, and the reaction time is 0.1 to 12 hr.

Step 2-7

Step 2-7 is a step of condensing the amino group at 1-position of the compound represented by formula (XXIV) produced in step 2-6 with the compound represented by formula (XVII) to give a compound represented by formula (XXV).

This step can be achieved under the same reaction conditions as the reaction conditions described in step 1-13 or reaction conditions similar to the reaction conditions described in step 1-13 in scheme 3.

Scheme 5 shows the step of reacting the compound represented by formula (XXV) with the compound represented by formula (Xc) (step 2-8),

[Chemical formula 29]

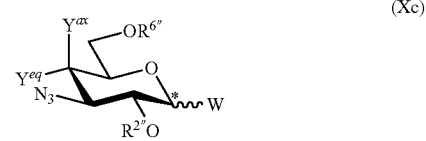

wherein W, $Y^{ax}$, $Y^{eq}$, $R^{6''}$, $R^{2''}$, and the steric configuration of carbon atom attached with * are as defined above, and The step of removing the protective group from the resultant compound (step 2-9 and step 2-10) and the step of reducing the azido group of the compound to give a compound represented by formula (Ia) (step 2-10) are explained below.

Scheme 5

[Chemical formula 30]

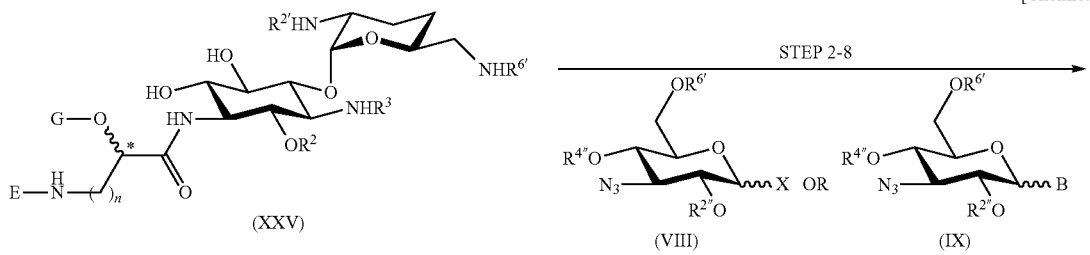

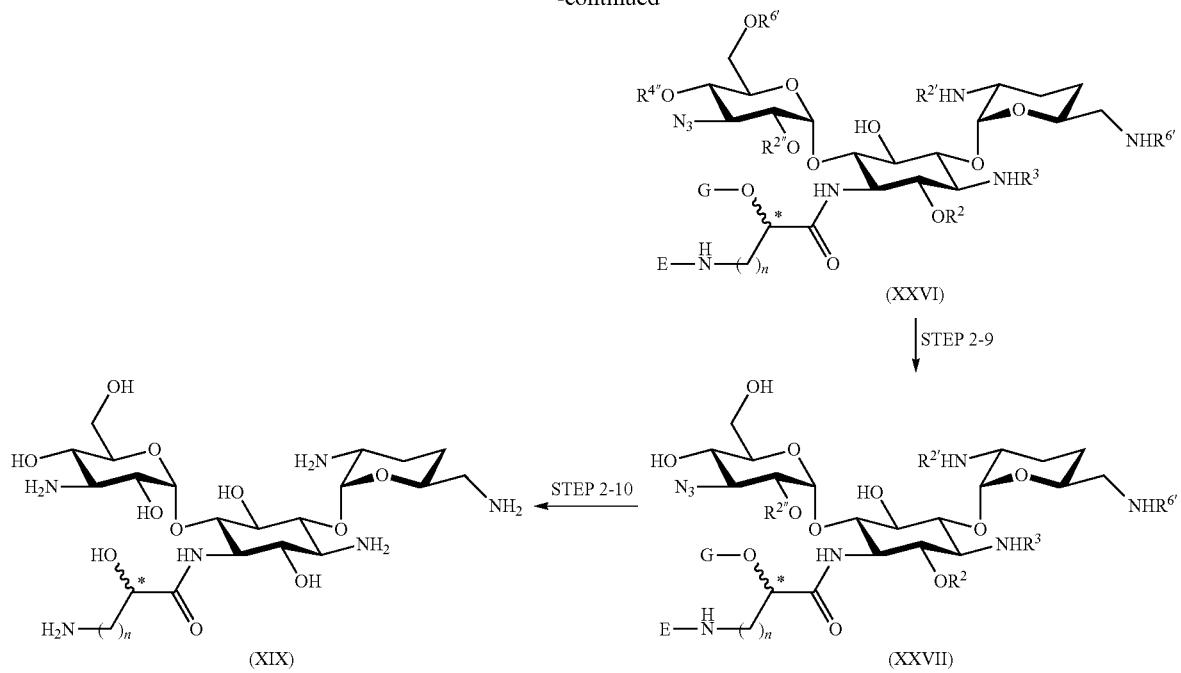

wherein $R^2$, $R^3$, $R^{2'}$, $R^{6'}$, $R^{2''}$, $R^{4''}$, $R^{6''}$, B, X, E, G, n, and the steric configuration of carbon atom attached with * are as defined above.

Step 2-8

Step 2-8 is a step of condensing the compound represented by formula (XXV) produced in scheme 4 with the compound represented by formula (Xc) (the compound represented by formula (VIII) or the compound represented by formula (IX)) to give a compound represented by formula (XXVI).

This step can be achieved under the same reaction conditions as the reaction conditions described in step 1-8 or reaction conditions similar to the reaction conditions described in step 1-8 in scheme 3.

Step 2-9

Step 2-9 is a step of removing two protective groups ($R^{4''}$ and $R^{6''}$) for hydroxyl group in the compound represented by formula (XXVI) to give a compound represented by formula (XXVII).

This step can be achieved by hydrolysis under basic conditions or under acidic conditions, or by treating the compound with a nucleophilic base, for example, sodium methoxide or sodium ethoxide under anhydrous conditions.

In the case of hydrolysis, in addition to water, alcohol solvents such as methanol or ethanol, and solvents miscible with water, for example, with tetrahydrofuran or 1,4-dioxane may be used as the reaction solvent. Further, solvents immiscible with water, for example, ethyl acetate and methylene chloride, may be used by adopting a two layer-type reaction with water. Solvents commonly used in organic synthesis may be used as the solvent under anhydrous conditions.

Step 2-10

Step 2-10 is a step of reducing the azido group in the compound represented by formula (XXVII) produced in step 2-9 to amino group and further removing three protective groups ($R^3$, $R^{2'}$, and $R^{6'}$) for amino group and the protective group ($R^2$) for hydroxyl group at 2-position to give a compound represented by formula (XIX) which is a compound represented by formula (Ia) wherein both $R^{5ax}$ and $R^{4''ax}$ represent a hydrogen atom and both $R^{5eq}$ and $R^{4''eq}$ represent hydroxyl.

In this reaction, the reduction reaction of the azido group and the deprotection may be carried out separately from each other through a plurality of stages. Alternatively, when both the reactions can be carried out under the same reaction conditions, this step may be carried out by a single reaction.

A reaction with hydrogen in the presence of a catalytic hydrogen reduction catalyst may be mentioned as the reaction through which the azido group is reduced and converted to amino group. Catalytic hydrogen reduction catalysts usable herein include palladium-carbon, palladium black, palladium hydroxide, Raney nickel, or platinum oxide. Among them, palladium black is preferred. Any solvent may be used without particular limitation so far as the solvent is inert to this reaction. Preferred solvents include methanol, ethanol, tetrahydrofuran, dioxane, acetic acid, a mixed solvent composed of them, or a mixed solvent composed of the organic solvent and water. A hydrogen gas may be used as hydrogen to be added. The pressure of the hydrogen gas may be 1 atm which is the atmospheric pressure. If necessary, pressurized hydrogen gas may also be used. Hydrogen sources different from the hydrogen gas, for example, formic acid, salts of formic acid, and cyclohexene may also be used according to need.

Methods for reducing the azido group for conversion to amino group include the method of Staudinger et al. in which the azido compound is reacted with phosphine or phosphite to give iminophosphorane which is then hydrolyzed for conversion to amino (Helvetica Chemica Acta, Vol. 2, p. 635 (1919)). Phosphine reagents usable in this method include triphenylphosphine and trimethylphosphine. For example, trimethyl phosphite may be mentioned as the phosphite reagent. Solvents usable in the reaction include tetrahydrofuran, 1,4-dioxane, diethyl ether, acetonitrile, methylene chloride, water, and a mixed solvent composed of them. Iminophosphorane produced as an intermediate may be isolated before hydrolysis. The production of iminophosphorane and hydrolysis can be carried out in one step by adding water to a reaction solvent.

The method for removing the three protective groups ($R^3$, $R^{2'}$, and $R^{6'}$) for amino group and the protective group ($R^2$) for hydroxyl group at 2-position may be selected by taking into consideration deprotection conditions commonly used in organic synthesis depending upon the type of the protective group. The method may be carried out stepwise or in one step.

When a protective group, which can remove by a catalytic hydrogenation reaction, is selected for both the three protective groups ($R^3$, $R^{2'}$, and $R^{6'}$) for amino group and the protective group ($R^2$) for hydroxyl group at 2-position and, in this case, when all of $R^3$, $R^{2'}$, and $R^{6'}$ represents benzyloxycarbonyl while $R^2$ represents benzyl, a reduction reaction for converting the azido group to amino group can also be advantageously simultaneously achieved by a one-step catalytic hydrogenation reaction.

(3) Production of Compounds of which the 5- and 4"-Positions are Equatorial: Second Production Process In the second production process according to the present invention, the compound represented by formula (Ia) may also be produced by using the compound represented by formula (Xd) instead of the compound represented by formula (Xc).

[Chemical formula 31]

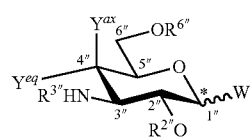

(Xd)

wherein W, $Y^{ax}$, $Y^{eq}$, $R^{2''}$, $R^{3''}$, $R^{6''}$, and the steric configuration of carbon atom attached with * are as defined above.

The second production process will be described with reference to scheme 6 (step 3-1 to step 3-4) and scheme 7 (step 3-5 to step 3-7).

In the following scheme 6, compounds represented by formula (Xd), wherein $Y^{ax}$ represents a hydrogen atom, $Y^{eq}$ represents hydroxyl, and W represents a leaving group (B), are described as compounds represented by formula (XXXI), and the production process thereof will be described.

Scheme 6

[Chemical formula 32]

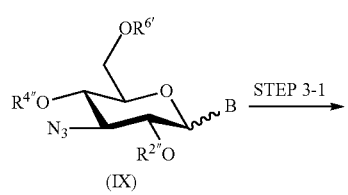

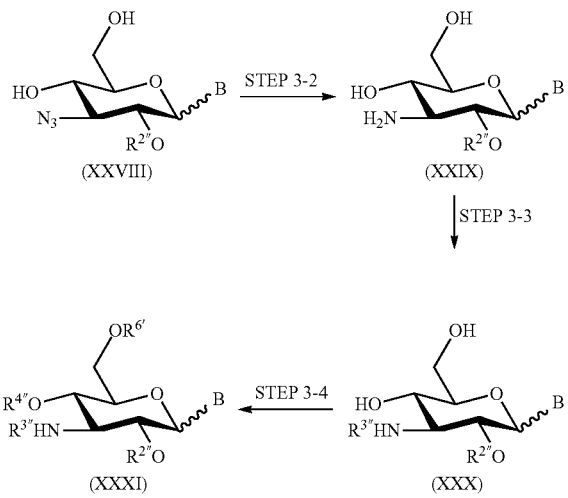

wherein
$R^{2''}$, $R^{3''}$, $R^{4''}$, $R^{6''}$, and B are as defined above; and $R^{4'''}$ and $R^{6'''}$ preferably represent an ester-type protective group.

Step 3-1

Step 3-1 is a step of removing the two protective groups ($R^{4'''}$ and $R^{6'''}$) for hydroxyl group in the compound represented by formula (IX) to give a compound represented by formula (XXVIII).

When $R^{4'''}$ and $R^{6'''}$ represent an ester-type protective group, a hydrolysis reaction or a solvolysis reaction can be applied. More preferred is a solvolysis reaction.

More specifically, the solvolysis reaction may be carried out using sodium methoxide, sodium ethoxide or the like. Any solvent may be used without limitation so far as the solvent is inert to the reaction. Preferred are alcohol solvents such as methanol and ethanol.

The reaction temperature is in the range of −20° C. to the reflux temperature, and the reaction time is 0.1 to 12 hr.

Step 3-2

Step 3-2 is a step of reducing the azido group in the compound represented by formula (XXVIII) to amino group to give a compound represented by formula (XXIX).

In step 2-10 in scheme 5, the step of reducing the azido group to amino group is described in detail. The same conditions can be applied to step 3-2. In scheme 6, preferably, the method of Staudinger et al. (Helvetica Chemica Acta, Vol. 2, p. 635 (1919)) is used. The compound represented by formula (XXIX) produced in this step may be isolated for use in step 3-3. Alternatively, the compound as such may be subsequently used as a starting compound for step 3-3 without isolation.

Step 3-3

Step 3-3 is a step of protecting an amino group of the compound represented by formula (XXIX) to give the compound represented by formula (XXX).

Protective groups for amino group commonly used in organic synthesis may be used as the protective group. Preferably, the protective group can be one which can be removed by a catalytic hydrogenation reaction. Specifically, benzyl-type protective groups such as benzyloxycarbonyl may be mentioned as the protective group. The protective group may be introduced, for example, by a method described in connection with step 1-7 in scheme 2, a method using a chloroformic ester described in connection with step 2-1 in scheme 4, or a method using a benzyloxycarbonylation reagent such as an N-(benzyloxycarbonyloxy)succinimide group.

Step 3-4

Step 3-4 is a step of simultaneously protecting the hydroxyl group at 4-position and the hydroxyl group at 6-position in the compound represented by formula (XXX) to give a compound represented by formula (XXXI). $R^{4''}$ and $R^{6''}$ in scheme 6 preferably represent an ester-type protective group, particularly preferably acetyl.

The ester-type protective group can be introduced by a method commonly used in organic synthesis using the acid anhydride or the acid halide in the presence or absence of a base. Any solvent may be used without particular limitation so far as the solvent is inert to the reaction. Preferred is a solvent which can serves both as a solvent and a base such as pyridine.

The reaction temperature is in the range of −20° C. to the reflux temperature, and the reaction time is 0.1 to 72 hr.

Next, scheme 7 shows the step of reacting the compound represented by formula (XXV) with the compound represented by formula (XXXI) (step 3-5) and the step of removing the protective group of the resultant compound to give a compound represented by formula (XIX) (step 3-6 and 3-7).

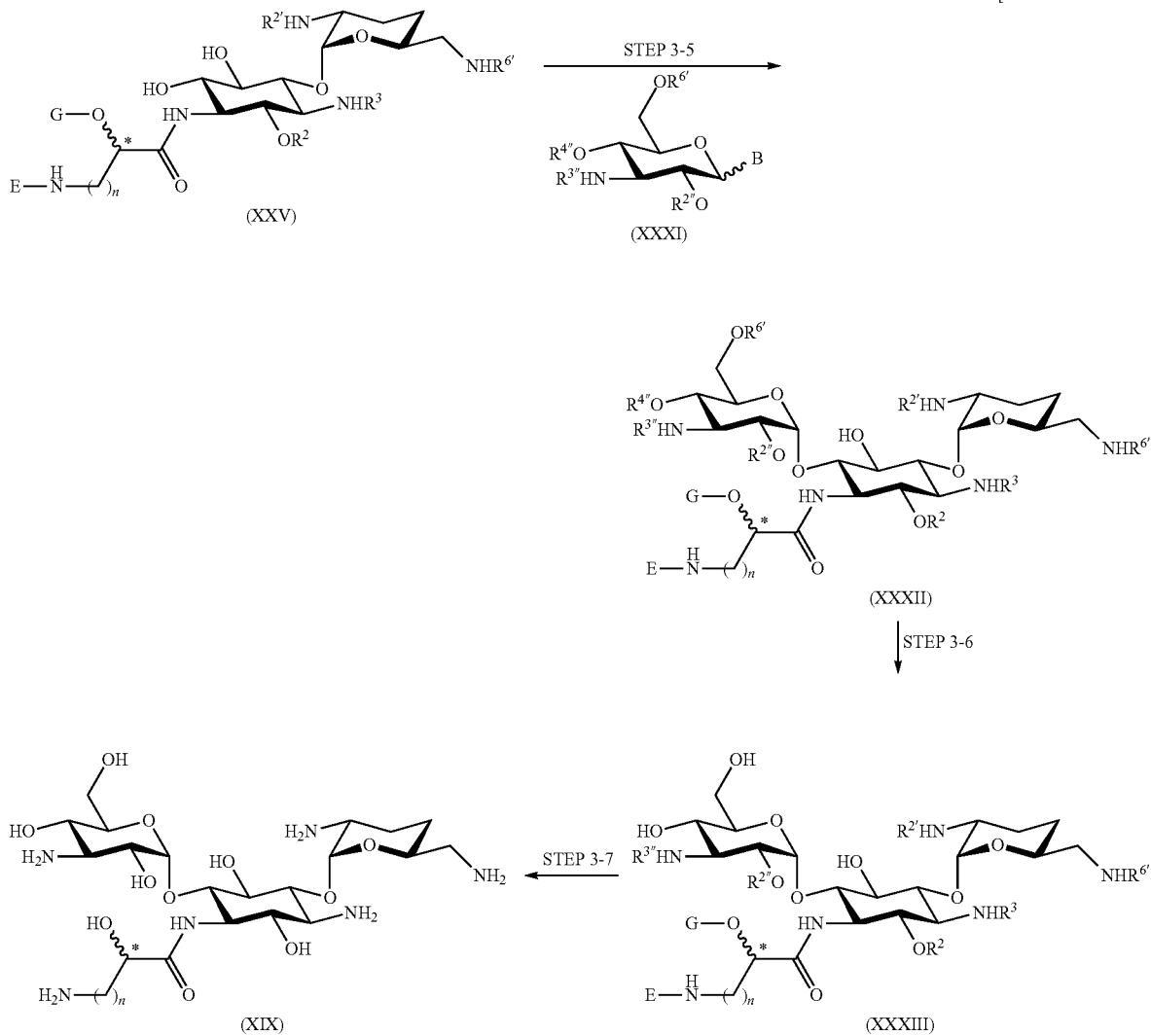

wherein $R^2$, $R^3$, $R^{2'}$, $R^{6'}$, $R^{2''}$, $R^{3''}$, $R^{4''}$, $R^{6''}$, B, E, G, n, and the steric configuration of carbon atom attached with * are as defined above.

Step 3-5

Step 3-5 is a step of condensing the compound represented by formula (XXV) produced in scheme 4 with the compound represented by formula (XXXI) in scheme 6 to give a compound represented by formula (XXXII).

Specifically the condensation can be carried out in the same manner as in step 2-8 in scheme 5.

Step 3-6

Step 3-6 is a step of removing the two protective groups ($R^{4''}$ and $R^{6''}$) for hydroxyl group in the compound represented by formula (XXXII) produced in step 3-5 to convert the compound represented by formula (XXXIII).

Specifically, this step can be carried out in the same manner as in step 2-9 in scheme 5.

Step 3-7

Step 3-7 is a step of removing all the protective groups ($R^2$, $R^3$, $R^{2'}$, $R^{6'}$, $R^{2''}$, $R^{3''}$, E, and G) in the compound represented by formula (XXXIII) produced in step 3-6 to give a compound represented by formula (XIX) which is a compound represented by formula (Ia) in which both $R^{5eq}$ and $R^{4''ax}$ represent a hydrogen atom and both $R^{5eq}$ and $R^{4''eq}$ represent hydroxyl.

All the protective groups ($R^2$, $R^3$, $R^{2'}$, $R^{6'}$, $R^{2''}$, $R^{3''}$, E, and G) in the compound represented by formula (XXXIII) can be removed stepwise or in one step (if possible) under deprotection conditions in conventional organic synthesis. For example, when all the protective groups in the compound represented by formula (XXXIII) can be removed by a catalytic hydrogenation reaction, the protective groups can be removed in one step by applying the same catalytic hydrogenation reaction conditions as in step 1-14 in scheme 3 or conditions similar to the catalytic hydrogenation reaction conditions in step 1-14 in scheme 3.

(4) Production of Compounds of which the 5-Position is Equatorial and the 4''-Position is Axial: Second Production Process Further, according to the second production process of the present invention, compounds represented by formula (Ia), wherein both $R^{5ax}$ and $R^{4''eq}$ represent a hydrogen atom and both $R^{5eq}$ and $R^{4''ax}$ represent hydroxyl, can be produced according to scheme 8 (step 4-1 to step 4-5a and step 4-5b) and scheme 9.

The process for producing compounds represented by formula (Xc) will be described in detail with reference to scheme 8.

[Chemical formula 34]

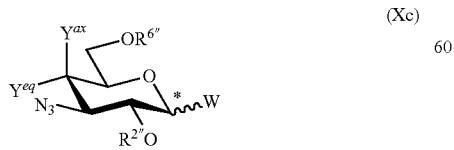

wherein W represents a leaving group; $Y^{ax}$ represents group —$OR^{4''}$; $Y^{eq}$ represents a hydrogen atom; $R^{2''}$, $R^{4''}$ and $R^{6''}$ represent a protective group for hydroxyl group; and the steric configuration of carbon atom attached with * represents R or S.

In scheme 8, the compounds represented by formula (Xc) are classified according to the type of the leaving group represented by W into compounds represented by formula (XXXVIII) and compounds represented by formula (XXXIX).

Scheme 8

[Chemical formula 35]

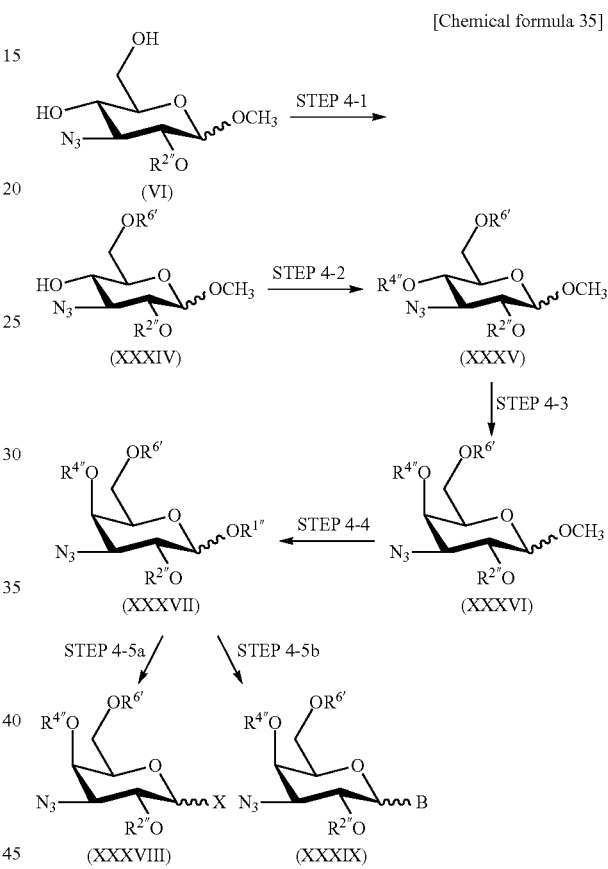

wherein $R^{2''}$ represents a protective group for hydroxyl group, preferably a group selected from benzyl ether-type protective groups such as benzyl and p-methoxybenzyl; $R^{4''}$ and $R^{6''}$, which are different from each other, represent a protective group for hydroxyl group, for example, are selected from ester-type protective groups such as acetyl and benzoyl, and sulfonyl-type protective groups such as p-toluenesulfonyl, methanesulfonyl, and trifluoromethanesulfonyl; and B and X are as defined above.

Step 4-1

Step 4-1 is a step of selectively introducing a protective group ($R^{6''}$) into only the hydroxyl group located at 6-position in the two hydroxyl groups in the compound represented by formula (VI) in scheme 1 to give the compound represented by formula (XXXIV).

The protective group introduced is preferably a structurally bulky protective group among protective groups used as a protective group for hydroxyl group in organic synthesis, specifically preferably benzoyl or substituted benzoyl.

The reaction may be carried out in the same manner as in step 3-4 in scheme 6.

Step 4-2

Step 4-2 is a step of introducing a leaving group into the hydroxyl group at 4-position of the compound represented by formula (XXXIV) to give a compound represented by formula (XXXV) which is a starting compound in step 4-3 for synthesizing a compound represented by formula (XXXVI) in which the hydroxyl group at 4-position has been inverted.

A leaving group having a higher leaving ability than the protective group introduced in $R^{6''}$ in step 4-2 among leaving groups for hydroxyl group in organic synthesis is selected as the leaving group introduced. Specifically, a sulfonyl-type leaving group is selected. More specifically, for example, $R^{4''}$ in formula (XXXV) is preferably trifluoromethanesulfonyl.

The reaction can be carried out in the same manner as in step 3-4 in scheme 6.

Step 4-3

Step 4-3 is a step of utilizing the leaving group at 4-position of the compound represented by formula (XXXV) to give a compound represented by formula (XXXVI) of which the steric configuration at 4-position has been inverted.

$R^{4''}$ in the compound represented by formula (XXXVI) is preferably a protective group which serves as a protective group for hydroxyl group at 4-position and can be removed in the same manner as in $R^{6''}$ as the protective group for hydroxyl group at 6-position. $R^{4''}$ is an ester-type protective group, preferably acetyl.

The reaction which can provide the compound represented by formula (XXXVI) can be achieved by reacting the metal salt of a carboxylic acid with the compound represented by formula (XXXV). The acetyl group which is preferred as $R^{4''}$ can be successfully introduced by using a salt of acetic acid such as cesium acetate.

Any solvent may be used without particular limitation so far as the solvent is inert to this reaction. The solvent is preferably N,N-dimethylformamide.

The reaction temperature is in the range of −20° C. to reflux temperature, and the reaction time is 0.1 to 72 hr.

Step 4-4

Step 4-4 is a step of converting the methoxy group at 1-position of the compound represented by formula (XXXVI) to acyloxy ($OR^{1''}$) to give the compound represented by formula (XXXVII).

This step can be achieved in the same manner as in step 1-4 in scheme 1.

Step 4-5a

Step 4-5a is a step of converting the acyloxy group ($OR^{1''}$) at 1-position of the compound represented by formula (XXXVII) to a halogen atom to give a compound represented by formula (XXXVIII).

This step can be carried out in the same manner as in step 1-5a in scheme 1.

Step 4-5b

Step 4-5b is a step of converting the acyloxy group ($OR^{1''}$) at 1-position of the compound represented by formula (XXXVII) to thioalkyl or thioaryl in the presence of Lewis acid to give a compound represented by formula (XXXIX).

This step can be carried out in the same manner as in step 1-5b in scheme 1.

The substituent at 1-position of the compound shown in scheme 8 can take two steric configurations, that is, an equatorial form and an axial form. In scheme 8, they may be separated from each other before use in the reaction, or alternatively the two steric configurations in a mixed form as such may be used in the reaction. Further, the compound represented by formula (XXXVIII) and the compound represented by formula (XXXIX) produced in scheme 8 may be separated into an axial form and an equatorial form which are then used separately from each other in scheme 9. Alternatively, these compounds may be used as a mixture of the axial form with the equatorial form.

Scheme 9

[Chemical formula 36]

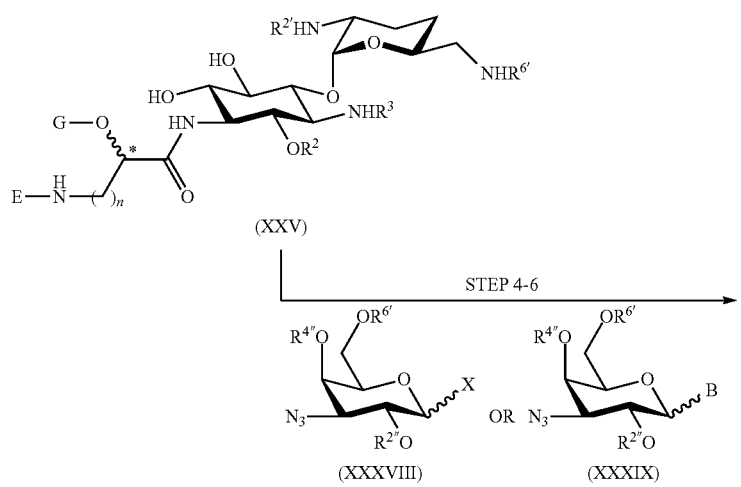

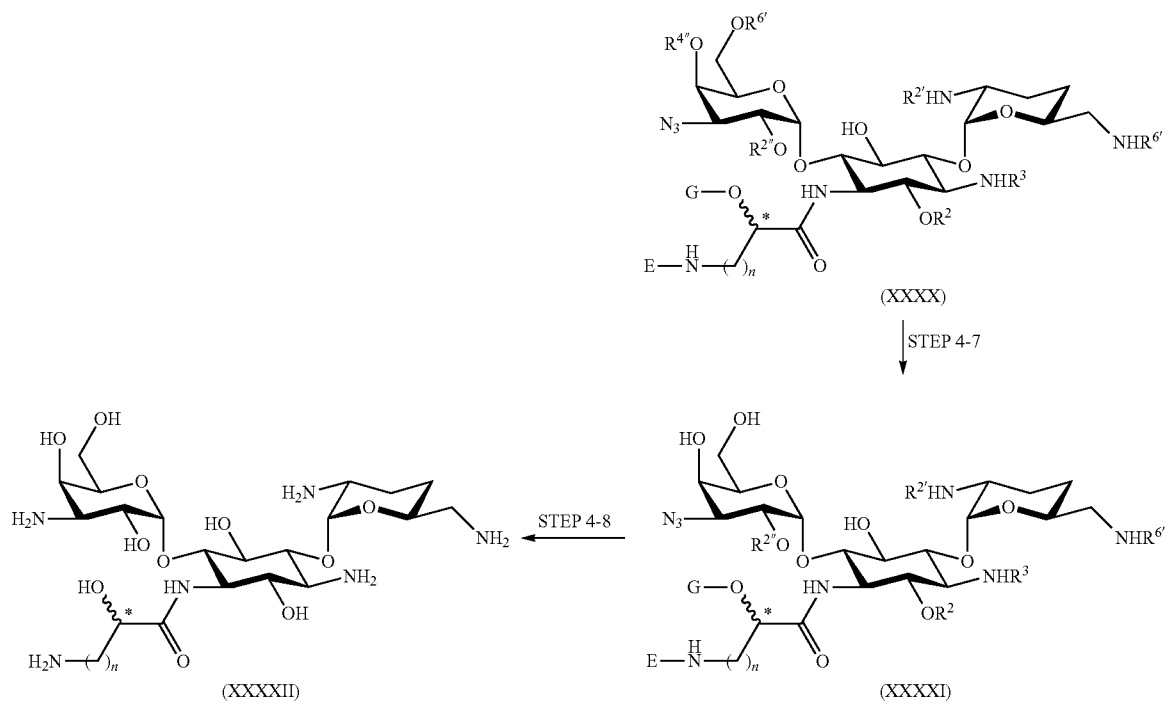

(XXXX)

|STEP 4-7

(XXXXII) ← STEP 4-8 — (XXXXI)

wherein $R^2$, $R^3$, $R^{2'}$, $R^{6'}$, $R^{2''}$, $R^{4''}$, $R^{6''}$, B, E, G, X, n, and the steric configuration of the carbon atom attached with * are as defined above.

Step 4-6

Step 4-6 is a step of condensing the compound represented by formula (XXV) produced in scheme 4 with the compound represented by formula (XXXVIII) or formula (XXXIX) in scheme 8 to introduce a compound represented by formula (XXXX).

The condensation can be carried out in the same manner as in step 2-8 in scheme 5.

Step 4-7

Step 4-7 is a step of removing two protective groups ($R^{4''}$ and $R^{6''}$) for hydroxyl group in the compound represented by formula (XXXX) produced in the step 4-6 and converting to the compound represented by formula (XXXXI).

Specifically, this step can be carried out in the same manner as in step 2-9 in scheme 5.

Step 4-8

Step 4-8 is a step of removing all the protective groups ($R^2$, $R^3$, $R^{2'}$, $R^{6'}$, $R^{2''}$, E, and G) in the compound represented by formula (XXXXI) produced in the step 4-7 to give a compound represented by formula (XXXXII) which is a compound represented by formula (Ia) wherein $R^{5ax}$ and $R^{4''eq}$ represent a hydrogen atom and $R^{5eq}$ and $R^{4''ax}$ represent a hydroxyl.

Specifically, this step can be carried out in the same manner as in step 2-10 in scheme 5.

(5) Production of Compounds of which the 5-Position is Axial and the 4''-Position is Equatorial: First Production Process In the first production process according to the present invention, a compound represented by formula (Ia), wherein both $R^{5eq}$ and $R^{4''ax}$ represent a hydrogen atom and both $R^{5ax}$ and $R^{4''eq}$ represent hydroxyl, can be produced according to the following scheme 10 (step 5-1 to step 5-6) and scheme 11 (step 5-7 to step 5-13).

The production process of compounds represented by formula (Xa), wherein the steric configuration of the hydroxyl group at 5-position is axial, will be specifically described with reference to step 5-1 to step 5-6 in scheme 10. In scheme 10, the compound represented by formula (Xa), wherein the steric configuration of the hydroxyl group at 5-position is axial, corresponds to the compound represented by formula (XXXXVIII).

[Chemical formula 37]

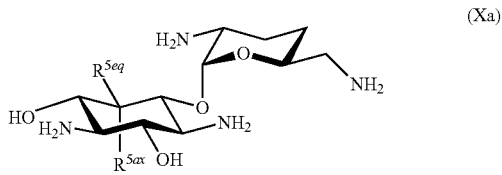

(Xa)

wherein, $R^{5ax}$ represents hydroxyl; and $R^{5eq}$ represents a hydrogen atom.

Scheme 10

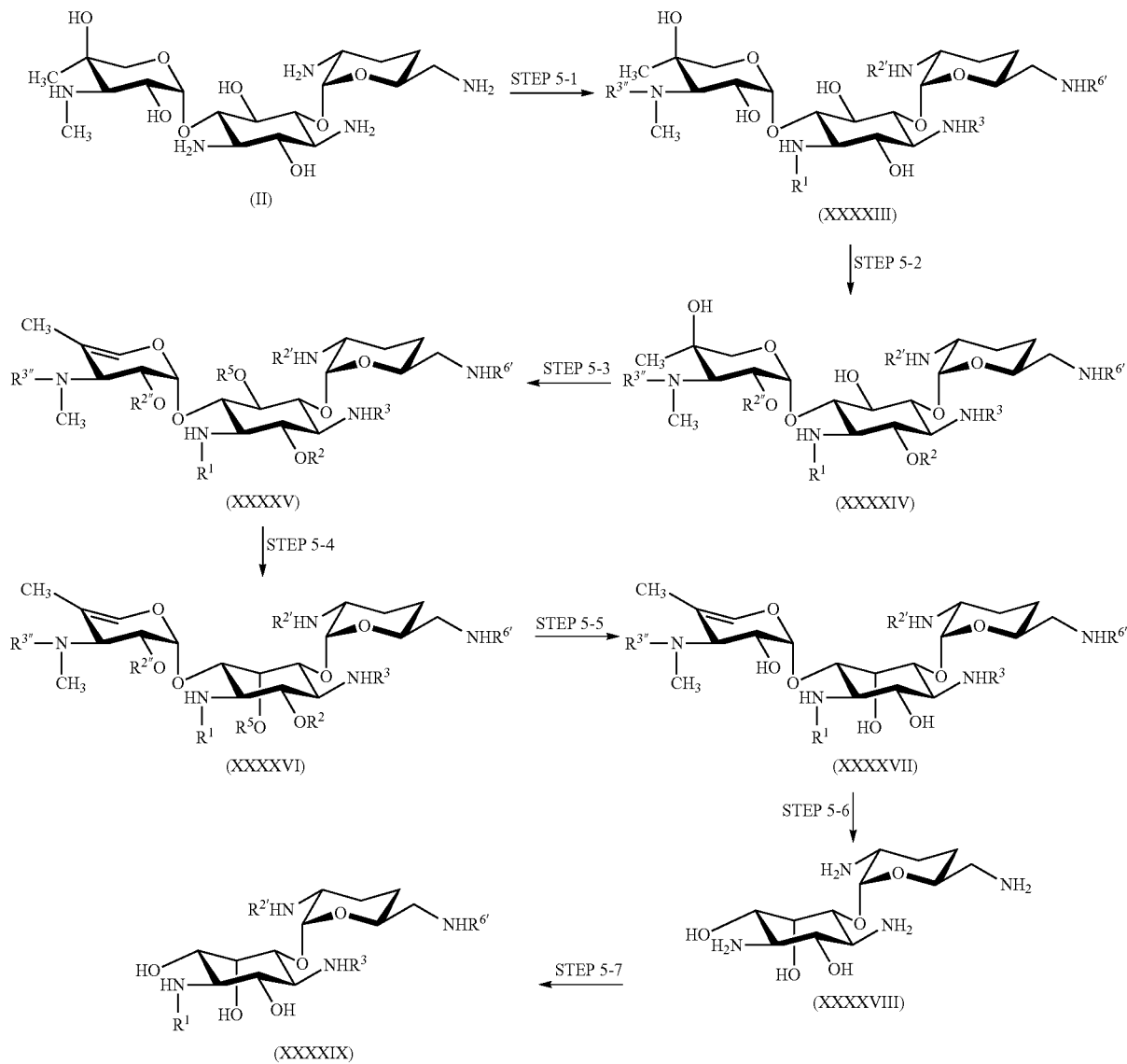

wherein, $R^1$, $R^3$, $R^{2'}$, $R^{6'}$, and $R^{3''}$ are as defined above; $R^5$ represents a protective group for hydroxyl group and is selected from, for example, ester-type protective groups such as acetyl or benzoyl and sulfonyl-type protective groups such as p-toluenesulfonyl, methanesulfonyl, or trifluoromethanesulfonyl; and $R^2$ and $R^{2''}$ are preferably an ester-type protective group.

Step 5-1

Step 5-1 is a step of introducing protective groups into five amino groups in 2-hydroxygentamicin C1a represented by formula (II).

The protective group introduced is preferably the protective group exemplified in scheme 2. In this step for producing a compound represented by formula (XXXXIII), tert-butoxycarbonyl is particularly preferred. The protective group can be introduced under conditions described in detail in connection with step 1-7 in scheme 2.

Step 5-2

Step 5-2 is a step of introducing protective groups ($R^2$ and $R^{2''}$) into two hydroxyl groups in the compound represented by formula (XXXXIII). An ester-type protective group such as acetyl is preferred as the protective group introduced, and acetyl is selected for the compound represented by formula (XXXXIV).

The acetyl group can be introduced in the same manner as in step 3-4 in scheme 6.

Step 5-3

Step 5-3 is a step of introducing a leaving group into the tertiary hydroxyl group of the compound represented by formula (XXXXIV) in the presence of a base to cause elimination and thus to form an unsaturated bond and, at the same time, introducing a leaving group into the hydroxyl group at 5-position to give a compound represented by formula (XXXXV).

The leaving group to be introduced may be selected from alkylsulfonyl groups such as methanesulfonyl and trifluoromethanesulfonyl, or arylsulfonyl groups such as p-toluenesulfonyl. In the production of the compound represented by formula (XXXXV), methanesulfonyl is preferred. The reaction is carried out by treating sulfonyl chloride and the compound represented by formula (XXXXIV) in the presence of a base. Bases usable in the reaction include organic bases such as triethylamine or 4-dimethylaminopyridine. Preferred is 4-dimethylaminopyridine.

Any solvent may be used in the reaction without particular limitation so far as the solvent is inert to the reaction. Preferred are halide solvents such as methylene chloride.

Step 5-4

Step 5-4 is a step of inverting the steric configuration at 5-position of the compound represented by formula (XXXXV) to introduce protected hydroxyl group and thus to synthesize a compound represented by formula (XXXXVI). An ester group is preferred as the protected hydroxyl group in consideration of a deprotection step which will be described later. In the compound represented by formula (XXXXVI), acetyl is preferred.

This step of introducing acetyl to invert the hydroxyl group at 5-position can be carried out in the same manner as in step 4-3 in scheme 8.

Step 5-5

Step 5-5 is a step of removing the three protective groups ($R^2$, $R^{2''}$, $R^5$) for hydroxyl groups in the compound represented by formula (XXXXVI) to give a compound represented by formula (XXXXVII).

In the compound represented by formula (XXXXVI), the three protective groups ($R^2$, $R^{2''}$, and $R^5$) for hydroxyl groups are acetyl. The deprotection thereof can be carried out under the same conditions as in step 3-1 of scheme 6 or under conditions similar to the conditions in step 3-1 of scheme 6.

Step 5-6

Step 5-6 is a step of subjecting the compound represented by formula (XXXXVII) to acid hydrolysis reaction to give a compound represented by formula (XXXXVIII).

This reaction can be carried out by reference to the reaction conditions of step 1-6 in scheme 2. A solvent, which does not inhibit the reaction, such as methanol, may also be additionally used from the viewpoint of enhancing the solubility of the compound represented by formula (XXXXVII) to accelerate the reaction.

Step 5-7

Step 5-7 is a step of introducing protective groups into the four amino groups in the compound represented by formula (XXXXVIII) produced in step 5-6 to give a compound represented by formula (XXXXIX).

The protective group to be introduced is preferably a protective group exemplified in scheme 2, more preferably p-toluenesulfonyl. Conditions described in detail in step 1-7 of scheme 2 may be applied to the introduction of the protective group.

The compound represented formula (Ia), wherein both $R^{5eq}$ and $R^{4''ax}$ represent a hydrogen atom and both $R^{5ax}$ and $R^{4''eq}$ represent hydroxyl, can be produced according to scheme 12 (step 5-8 to step 5-14). In scheme 12, the compound is represented by formula (XXXXXVI).

Scheme 11 includes the step of reacting the compound represented by formula (XXXXIX) with the compound represented by formula (Xc) (step 5-8), the step of removing the protective groups of the resultant compound and converting the azido group in the compound to amino group (step 5-9 and step 5-10), the step of optionally introducing a protective groups into functional groups other than the amino group at 1-position in the resultant compound (step 5-11 and step 5-12), the step of reacting the resultant compound with the compound represented by formula (XVII) (step 5-13), and the step of removing the protective groups in the resultant compound to give a contemplated compound represented by formula (XXXXXVI) (step 5-14). In scheme 11, the compound represented by formula (Xc) corresponds to the compound represented by formula (VIII) or formula (IX).

Scheme 11

[Chemical formula 39]

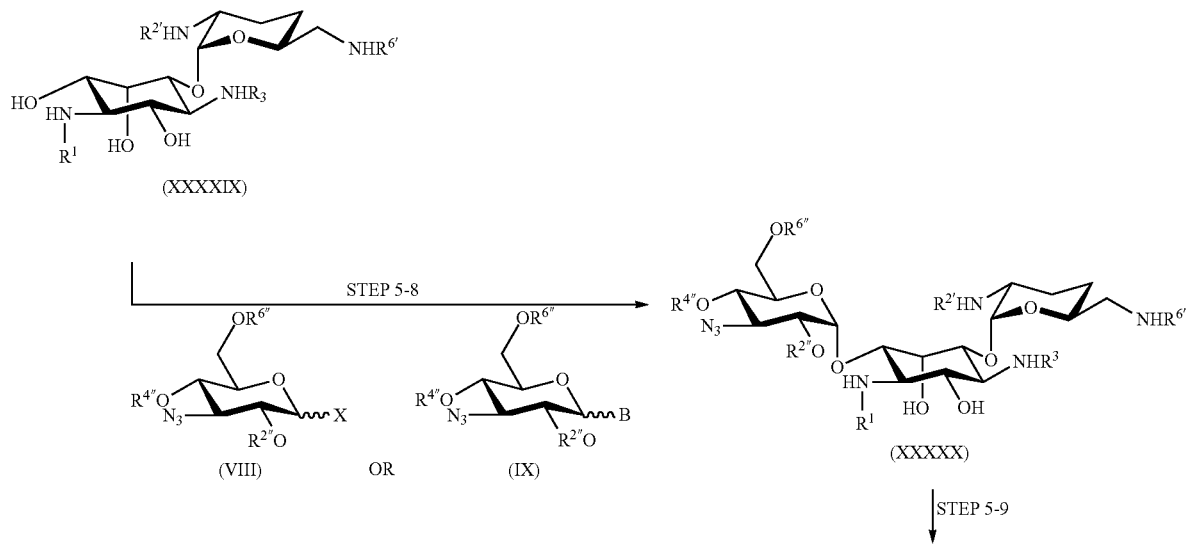

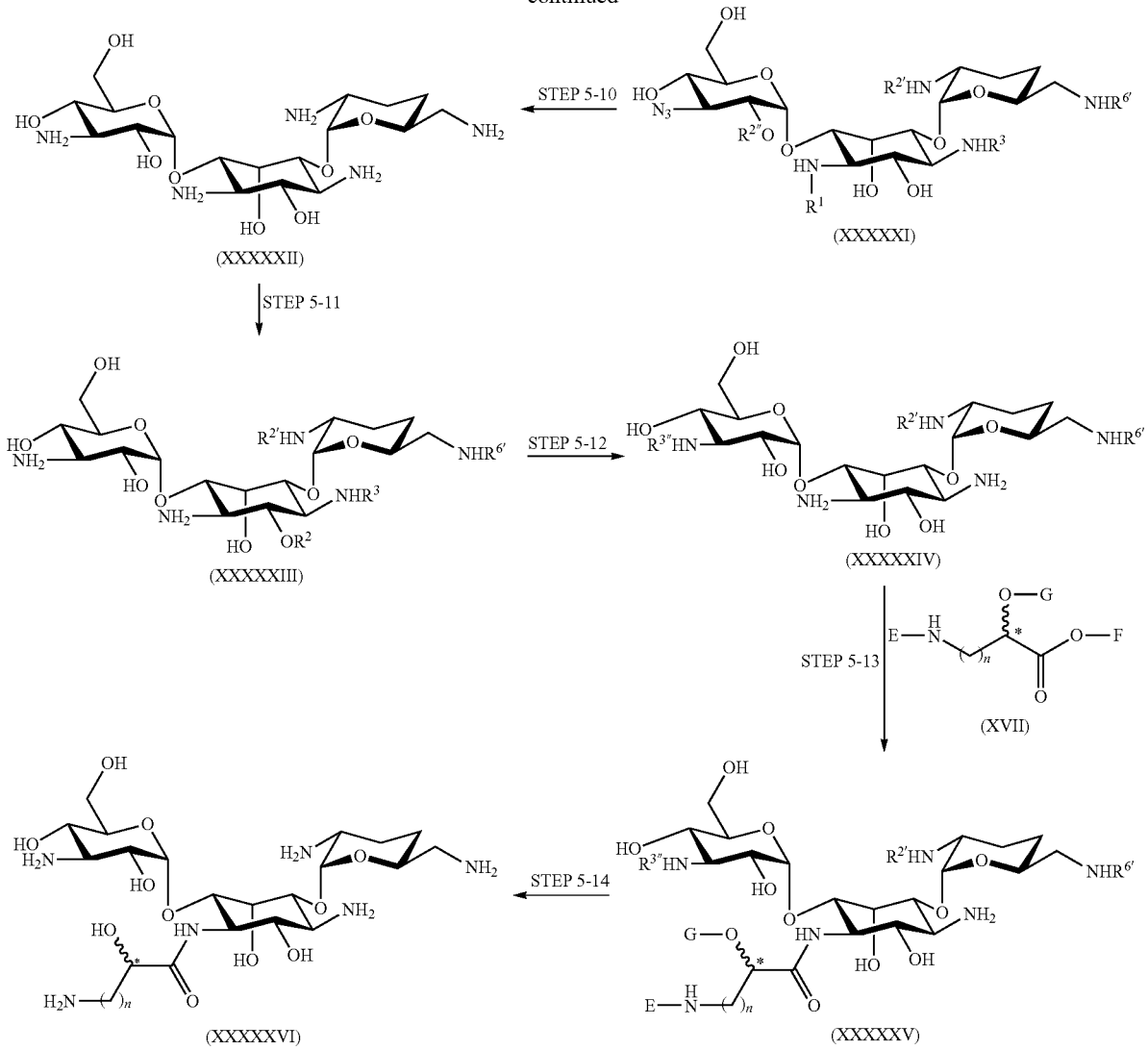

wherein $R^1$, $R^3$, $R^{2'}$, $R^{6'}$, $R^{2''}$, B, E, F, G, X, n, and the steric configuration of carbon atom attached with * are as defined above; and, $R^{4'''}$ and $R^{6'''}$ independently represent protective groups for hydroxyl, which are respectively the same protective groups for hydroxyl groups as defined in scheme 1, and are selected from ester-type protective groups such as acetyl and benzoyl.

Step 5-8

Step 5-8 is a step of condensing the compound represented by formula (XXXXIX) produced in scheme 10 with the compound represented by formula (VIII) produced in scheme 1 or the compound represented by formula (IX) to give a compound represented by formula (XXXXX). In formula (VIII) or formula (IX), $R^{4'''}$ and $R^{6'''}$ which are an ester-type protective group for hydroxyl group are preferably acetyl.

The reaction in this step can be achieved under the same conditions used in step 1-8 in scheme 3 or under conditions similar to the conditions used in step 1-8 in scheme 3.

Step 5-9

Step 5-9 is a step of removing the two protective groups ($R^{4'''}$ and $R^{6'''}$) for hydroxyl groups in the compound represented by formula (XXXXX) produced in step 5-8 to give a compound represented by formula (XXXXXI).

The two protective groups ($R^{4'''}$ and $R^{6'''}$) for hydroxyl groups in the compound represented by formula (XXXXX) are acetyl and can be removed in the same manner as in step 3-1 in scheme 6.

Step 5-10

Step 5-10 is a step of reducing the azido group in the compound represented by formula (XXXXXI) produced in step 5-9 to amino group and further removing the four protective groups ($R^1$, $R^3$, $R^{2'}$ and $R^{6'}$) for amino groups and the protective group ($R^{2''}$) for hydroxyl group in one step to give a compound represented by formula (XXXXXII).

This step is the same as step 1-10 in scheme 3, and conditions for Birch reduction in the conditions for step 1-10 can be applied.

Step 5-11

Step 5-11 is a step of selectively introducing protective groups ($R^{2'}$ and $R^{6'}$) into the amino groups at 2'- and 6'-positions in the compound represented by formula (XXXXXII) produced in step 5-10 to give a compound represented by formula (XXXXXIII). In formula (XXXXXIII), $R^{2'}$ and $R^{6'}$ represent benzyloxycarbonyl, and the reaction conditions described in step 1-11 in scheme 3 can be applied.

Step 5-12

Step 5-12 is a step of selectively introducing a protective group ($R^{3''}$) into the amino group at 3"-position of the compound represented by formula (XXXXXIII) to give a compound represented by formula (XXXXXIV). In formula (XXXXXIV), preferably, $R^{3''}$ represents trifluoroacetyl, and the reaction conditions for step 1-12 in scheme 3 can be applied to the reaction.

Step 5-13

Step 5-13 is a step of reacting the amino group at the 1-position of the compound represented by formula (XXXXXIV) with a ω-amino-α-hydroxycarboxylic acid derivative represented by formula (XVII) to give a compound represented by formula (XXXXXV), that is, a step of conducting a reaction for peptide bond formation. This step can be carried out in the same manner as in step 1-13 in scheme 3.

Step 5-14

Step 5-14 is a step of removing all the protective groups in the compound represented by formula (XXXXXV) to give a compound represented by formula (Ia) wherein both $R^{5eq}$ and $R^{4''ax}$ represent a hydrogen atom and both $R^{5ax}$ and $R^{4''eq}$ represent hydroxyl.

This step can be achieved in the same manner as in step 1-14 in scheme 3.

(6) Production of Compound of which 5-Position is Axial and 4"-Position is Axial: Inversion Reaction of Steric Configuration at 4"-Position The compound represented by formula (Ia), wherein both $R^{5eq}$ and $R^{4''eq}$ represent a hydrogen atom and both $R^{5ax}$ and $R^{4''ax}$ represent hydroxyl, can be produced according to scheme 12 (step 6-1 to 6-8). In scheme 12, this compound is represented by formula (XXXXXXIV).

Scheme 12 includes the step of introducing protective groups into the functional groups other than the functional group at 4"-position of the compound represented by formula (XXXXXVI) produced in scheme 11 (step 6-1 to step 6-5), the step of inverting the steric configuration of the hydroxyl group at 4"-position (step 6-6), and the step of removing the protective groups (step 6-7 and step 6-8).

Scheme 12

[Chemical formula 40]

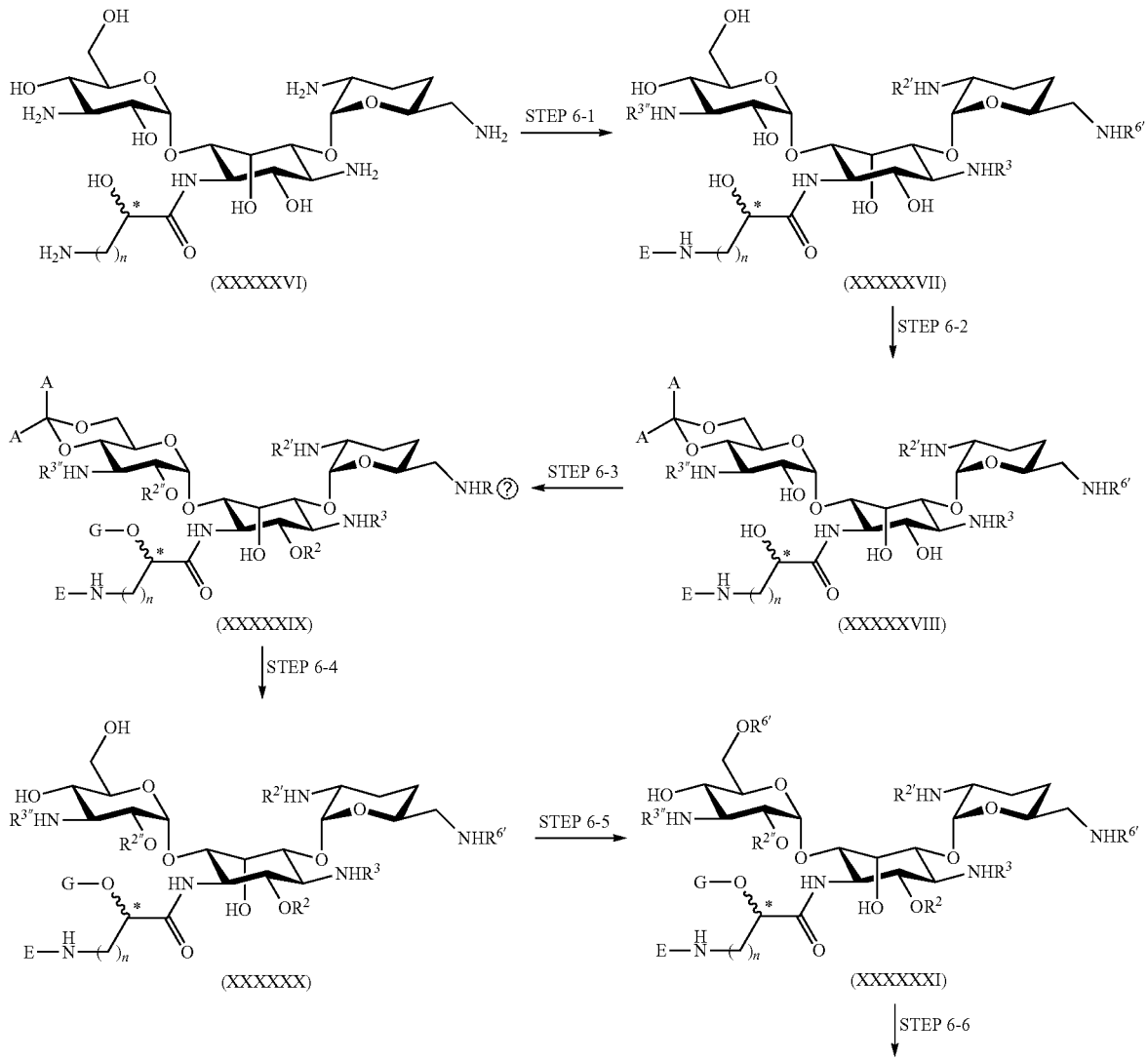

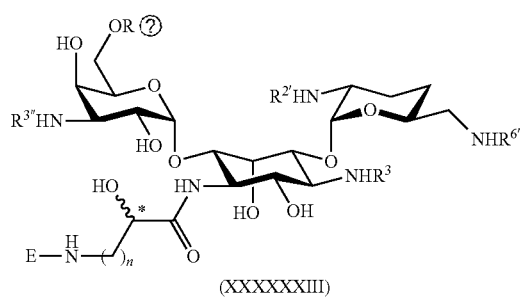

(XXXXXXIII)

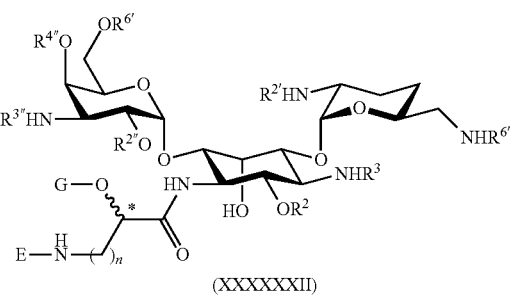

(XXXXXXII)

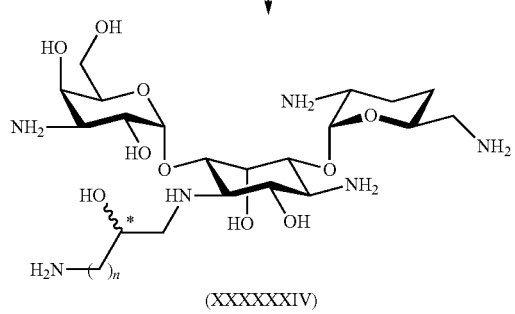

(XXXXXXIV)

wherein $R^3$, $R^{2'}$, $R^{6'}$, $R^{3''}$, and E represent a protective group for amino group, preferably t-butoxycarbonyl; $R^2$, $R^{2''}$, and G represent an ester-type protective group such as acetyl and benzoyl, preferably acetyl; $R^{4''}$ represents a group selected from the group consisting of ester-type protective groups such as acetyl and benzoyl and sulfonyl-type protective groups such as p-toluenesulfonyl, methanesulfonyl and trifluoromethanesulfonyl; $R^{6''}$ represents a protective group for hydroxyl group which can be removed under acidic condition such as triphenylmethyl; A represents C1-6 lower alkyl, or two of A together may form five-membered or eight-membered cyclic alkyl; and n and the steric configuration of carbon atom attached with * are as defined above.

Step 6-1

Step 6-1 is a step of introducing protective groups into the five amino groups in the compound represented by formula (XXXXXVI) produced in scheme 11 to give a compound represented by formula (XXXXXVII). This step can be carried out by the method described in detail in step 1-7 in scheme 2.

Step 6-2

Step 6-2 is a step of introducing cyclic acetal, preferably cyclohexylidene acetal, as a protective group into the two hydroxyl groups in the compound represented by formula (XXXXXVII). This step is similar to step 2-2 in scheme 4 and can be achieved by applying the reaction conditions adopted in step 2-2 in scheme 4.

Step 6-3

Step 6-3 is a step of protecting the three hydroxyl groups in the compound represented by formula (XXXXXVIII) produced in step 6-2 by ester-type protective groups.

Conditions for introducing an ester-type protective group for hydroxyl group in organic synthesis, for example, the conditions applied in step 3-4 in scheme 6, can be applied to this step.

Step 6-4

Step 6-4 is a step of removing the cyclic acetal as the protective group in the compound represented by formula (XXXXXIX) produced in step 6-3 to give a compound represented by formula (XXXXXX).

The conditions adopted in step 2-4 in scheme 4 can be applied to this step.

Step 6-5

Step 6-5 is a step of selectively introducing a protective group into the primary hydroxyl group in the compound represented by formula (XXXXXX) produced in step 6-4 to give a compound represented by formula (XXXXXXI).

A particularly bulky protective group selected from protective groups used as protective groups for hydroxyl group in conventional organic synthesis, specifically, for example, triphenylmethyl, is selected as the protective group to be introduced. The reaction is carried out by allowing triphenylmethyl chloride or triphenylmethyl bromide chloride to act on the compound represented by formula (XXXXXX) in the presence of a base. Any base may be used without particular limitation so far as the base is inert to the reaction. Preferred bases are, for example, pyridine and 4-dimethylaminopyridine. Further, in this reaction, any solvent may be used without particular limitation so far as the solvent is inert to the reaction.

Step 6-6

Step 6-6 is a step of inverting the hydroxyl group at 4"-position in the compound represented by formula (XXXXXXI) produced in step 6-5 to give a compound represented by formula (XXXXXXII).

This step is a step similar to the two steps, step 4-2 and step 4-3, in scheme 8 and can be carried out by applying the reaction conditions. Step 6-6 may also be divided into two steps as in scheme 8.

Step 6-7

Step 6-7 is a step of removing the four ester-type protective groups ($R^2$, $R^{2''}$, $R^{4''}$, and G) among the protective groups for hydroxyl group in the compound represented by formula (XXXXXXII) produced in step 6-6 to give a compound represented by formula (XXXXXXIII). This step can be carried out by applying step 2-9 in scheme 5.

Step 6-8

Step 6-8 is a step of removing all the protective groups in the compound represented by formula (XXXXXXIII) produced in step 6-7 to give a compound represented by formula (XXXXXXIV) which is a compound represented by formula (Ia) wherein both $R^{5eq}$ and $R^{4''eq}$ represent a hydrogen atom and both $R^{5ax}$ and $R^{4''ax}$ represent hydroxyl.

In formula (XXXXXXIII), reaction conditions for the deprotection depend upon the selected protective group. For example, when $R^3$, $R^{2'}$, $R^{6'}$, $R^{3''}$, and E represent t-butoxycarbonyl while $R^{6''}$ represents triphenylmethyl, the deprotection can be carried out under acidic conditions, for example, using trifluoroacetic acid.

As described above, according to the reaction shown in scheme 12, in the compound represented by formula (Ia) produced in the first or second production process according to the present invention, the steric configuration of the hydroxyl at the 4''-position can be inverted to axial. Accordingly, the first or second production process according to the present invention may comprise introducing a protective group into the functional group other than the hydroxyl group at the 4''-position of the compound represented by formula (Ia), inverting the steric configuration of the hydroxyl group at the 4''-position, and removing the protective group to give a compound represented by formula (Ia) wherein the steric configuration of the hydroxyl group at the 4''-position has been inverted. The present invention includes this embodiment as well (7) Production of Compound of which 5-Position is Axial and 4''-Position is Axial: Production of Synthetic Intermediate of which 5-Position is Axial and 4''-Position is Axial (First Production Process)

In the first production process according to the present invention, the compound represented by formula (Ia), wherein both $R^{5eq}$ and $R^{4''eq}$ represent a hydrogen atom and both $R^{5ax}$ and $R^{4''ax}$ represent hydroxyl, can be produced using a synthetic intermediate produced according to scheme 13.

In scheme 13, the compound represented by formula (XXXXXXVII) corresponds to a compound represented by formula (Xb) which is a synthetic intermediate in the first production process according to the present invention and of which the steric configuration of the hydroxyl group at the 5-position and 4''-position is axial.

[Chemical formula 41]

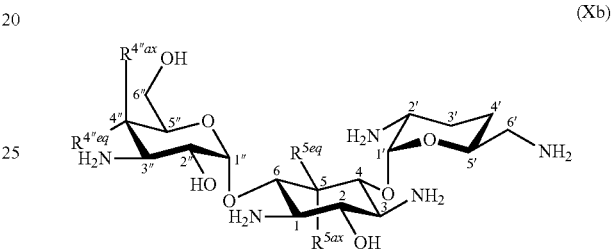

wherein both $R^{5eq}$ and $R^{4''eq}$ represent a hydrogen atom; and both $R^{5ax}$ and $R^{4''ax}$ represent hydroxyl.

Scheme 13

[Chemical formula 42]

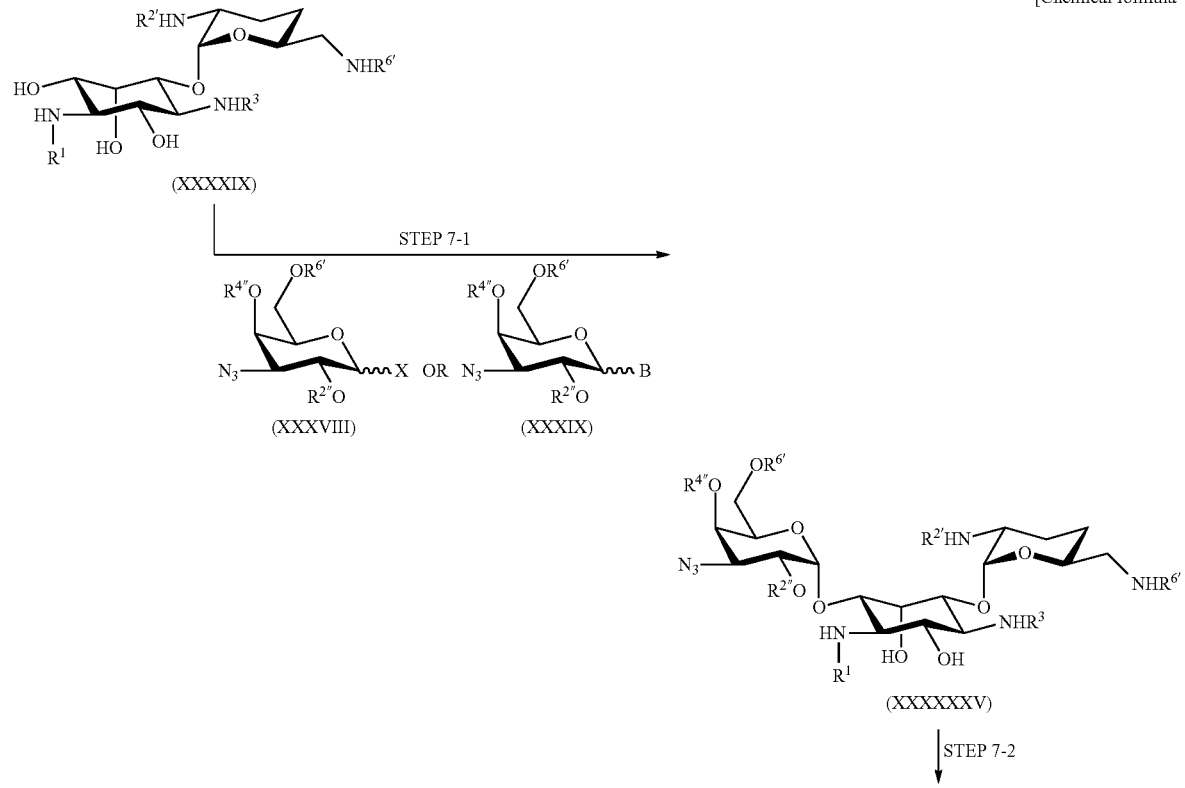

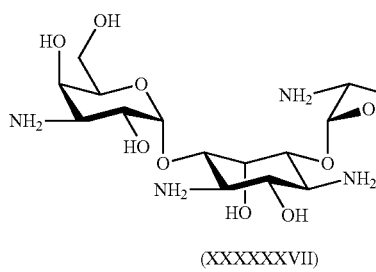

(XXXXXXVII)

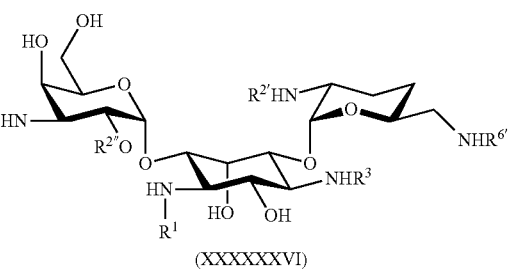

(XXXXXXVI)

wherein $R^1$, $R^3$, $R^{2'}$, and $R^{6'}$ represent protective groups for amino groups, preferably p-toluenesulfonyl; $R^{2''}$ represents an ether-type protective group such as benzyl, preferably benzyl; $R^{4''}$ represents an ester-type protective group such as acetyl or benzoyl, preferably acetyl; $R^{6''}$ represents an ester-type protective group such as acetyl or benzoyl, preferably benzoyl; B represents a sulfur atom-containing leaving group such as methylthio, ethylthio, or phenylthio, preferably phenylthio; and X represents a halogen atom such as chlorine, bromine, or iodine, preferably a bromine atom.

Step 7-1

Step 7-1 is a step of condensing the compound represented by formula (XXXXIX) produced in scheme 10 with the compound represented by formula (XXXVIII) or the compound represented by formula (XXXIX) in scheme 8 to give a compound represented by formula (XXXXXXV). This step can be carried out by the method which has been described in detail in step 2-8 in scheme 5.

Step 7-2

Step 7-2 is a step of removing the two ester-type protective groups ($R^{4''}$ and $R^{6''}$) in the compound represented by formula (XXXXXXV) to give a compound represented by formula (XXXXXXVI). This step is similar to step 5-9 in scheme 11 and can be achieved by applying the reaction conditions adopted in step 5-9 in scheme 11.

Step 7-3

Step 7-3 is a step of removing all the protective groups in the compound represented by formula (XXXXXXVI) produced in step 7-2, reducing the azido group to amino to give a compound represented by formula (XXXXXXVII).

The reaction condition's for the deprotection of the compound represented by formula (XXXXXXVII) vary depending upon the selected protective group. For example, when $R^1$, $R^3$, $R^{2'}$, and $R^{6'}$ represent p-toluenesulfonyl, the deprotection can be carried out, for example, by Birch reduction in which a radical reaction is carried out using liquid ammonia and metallic sodium.

It would be apparent to a person having ordinary skill in the art that, after step 7-3, the compound represented by formula (Ia) can be produced by applying step 1-11 to step 1-14 in scheme 3 to the compound represented by formula (XXXXXXVII).

The compounds according to the present invention and the compounds produced in the production steps can be purified and isolated by conventional purification operation. The purification and isolation can be carried out, for example, by liquid separation, distillation, sublimation, precipitation, crystallization, column chromatography on silica gel in which normal- or reverse-phase silica gel is packed, column chromatography using an ion exchange resin such as Amberlite CG-50, Dowex 50 W×2, or CM-Sephadex C-25, column chromatography using cellulose or the like, preparative thin-layer chromatography or high performance liquid chromatography. Alternatively, the compounds produced in the above productions steps can also be properly used in subsequent steps without the isolation and purification.

Antimicrobial Agent

The compounds represented by formula (Ia) according to the present invention or their pharmacologically acceptable salts, or their solvates have excellent antimicrobial activity against bacteria, which causes infectious diseases, for example, MRSA, *staphylococcus aureus*, colibacillus, and *Pseudomonas aeruginosa*, and are preferably used as antimicrobial agents, more preferably anti-MRSA agents. Thus, according to another aspect of the present invention, there is provided use of a compound according to the present invention or its pharmacologically acceptable salt or their solvates for the manufacture of an antimicrobial agent. Further, according to still another preferred aspect of the present invention, there is provided use of a compound according to the present invention or its pharmacologically acceptable salt or their solvates for the manufacture of an anti-MRSA agent.

Pharmaceuticals

The compounds represented by formula (Ia) according to the present invention or their pharmacologically acceptable salts, or their solvates optionally together with pharmaceutically acceptable additives may be used as pharmaceuticals. Thus, according to a further aspect of the present invention, there is provided a composition, especially a pharmaceutical composition comprising a compound represented by formula (Ia) or its pharmacologically acceptable salt, or their solvate. Further, according to another aspect of the present invention, there is provided use of a compound represented by formula (Ia) or its pharmacologically acceptable salt, or their solvate for the manufacture of a pharmaceutical composition. The pharmaceutical composition according to the present invention can be specifically used for preventing or treating an infectious disease. Preferred infectious diseases for which the pharmaceutical composition according to the present invention is very effective for the treatment or prevention, include nosocomial infectious diseases and opportunistic infectious diseases. More preferred are skin suppurative diseases, tympanitis, sinusitis, conjunctivitis, pneumonia, bronchitis, sepsis, cystitis, pyelonephritis, enteritis (including food poisoning) and the like.

The pharmaceutical composition according to the present invention can be administered to patients parenterally or orally by administration routes, for example, parenteral administration (for example, intravenous administration, intramuscular administration, subcutaneous administration, rectal administration, or percutaneous administration), or oral administration depending, for example, upon the type of pathogenic bacteria and diseases and the nature of the patient. Further, the pharmaceutical composition according to the present invention may be formulated into a suitable dosage form depending upon the administration route. Examples of such dosage forms include, for example, injections used mainly, for example, for intravenous administration and intramuscular administration; external preparations for parenteral administration, for example, eye drops, ear drops, nasal drops, ophthalmic ointments, skin mucosa absorbers, dermatologic preparations, inhalants, or suppositories; and preparations for oral administration, for example, capsules, tablets, pills, fine subtilaes, granules, powders, syrups, or troches.

The above preparations can be produced by a conventional method using additives, for example, excipients, extenders, binders, wetting agents, disintegrators, surfactants, lubricants, dispersants, buffers, preservatives, solubilizers, antiseptics, corrigents, soothing agents, and stabilizers. Specific examples of nontoxic additives usable herein, for injections, eye drops, ear drops, and nasal drops, include, dissolving agents or solubilizers which can constitute aqueous or dissolution-before-use dosage forms (for example, distilled water for injection, physiological saline, ethanol, glycerin, propylene glycol, corn oils, and sesame oils), pH adjustors (for example, inorganic acid addition salts such as trisodium orthophosphate and sodium hydrogencarbonate, organic acidic salts such as sodium citrate, and organic basic salts such as L-lysine and L-arginine), tonicity adjusting agents (for example, sodium chloride, glucose, and glycerin), buffering agents (for example, sodium chloride, benzalkonium chloride, and sodium citrate), surfactants (for example, sorbitan monooleate and polysorbate 80), dispersing agents (for example, D-mannitol), stabilizers (for example, antioxidants such as ascorbic acid, sodium sulfite, and sodium pyrosulfite and chelate agents such as citric acid and tartaric acid); for ophthalmic ointments, skin mucosa absorbers, and dermatologic preparations, include, for example, preparation components suitable as ointments, creams, and patch preparations (for example, white petrolatum, macrogol, glycerin, liquid paraffin, and cotton clothes); for liquid inhalants, include, for example, pH adjustors (for example, sodium citrate and sodium hydroxide), tonicity adjusting agents (for example, sodium chloride, benzalkonium chloride, and sodium citrate), and buffering agents (for example, sodium chloride, benzalkonium chloride, and sodium citrate); for powdery inhalants, include, for example, lactose as a carrier; and, for preparations for oral administration and suppositories, include, for example, excipients (for example, lactose, D-mannitol, corn starch, and crystalline cellulose), disintegrators (for example, carboxymethylcellulose and carboxymethylcellulose calcium), binders (for example, hydroxypropylcellulose, hydroxypropylmethylcellulose, and polyvinyl pyrrolidone), lubricants (for example, magnesium stearate and talc), coating agents (for example, shellac, hydroxypropylmethylcellulose, saccharose, and titanium oxide), plasticizers (for example, glycerin and polyethylene glycol), and substrates (for example, cacao butter, polyethylene glycol, and hard fat).

Further, when an enhancement in the therapeutic or preventive effect of infectious diseases is taken into consideration, the pharmaceutical composition according to the present invention may contain, in addition to the compound according to the present invention, clinically useful one or more conventional antimicrobial agents (for example, β-lactam antimicrobial agents (for example, carbapenems, cephalosporins, cephamycins, and penicillins), glycopeptide antimicrobial agents, ansamycin antimicrobial agents, aminoglycoside antimicrobial agents, quinolone antimicrobial agents, monobactam antimicrobial agents, macrolide antimicrobial agents, tetracycline antimicrobial agents, chloramphenicol antimicrobial agents, lincomycin antimicrobial agents, streptogramin antimicrobial agents, oxazolidinone antimicrobial agents, fosfomycins, novobiocins, cycloserines, and moenomycins). Alternatively, the pharmaceutical composition together with the above antimicrobial agent may be administered to the living body. Further, when the fact that the pharmaceutical composition according to the present invention can expand or improve the effectiveness against gram-negative bacteria and resistant bacterial against existing antimicrobial agents is taken into consideration, the pharmaceutical composition according to the present invention may contain, for example, a drug discharge pump (efflux pump) inhibitor and an existing antimicrobial agent degradative enzyme (for example, β-lactamase) inhibitor. Alternatively, the pharmaceutical composition according to the present invention, together with these inhibitors or the like may be administered to the living body. Furthermore, when the fact that the pharmaceutical composition according to the present invention can enhance the therapeutic or preventive effect of infectious diseases is taken into consideration, the pharmaceutical composition according to the present invention can be used in combination with compounds not having any antimicrobial activity (for example, medicaments for treating complication). The present invention includes this embodiment.

As described above, the compound represented by formula (Ia) according to the present invention or its pharmacologically acceptable salt, or their solvate can be advantageously utilized as an antimicrobial agent or a pharmaceutical in the prevention or treatment of infectious diseases. Thus, according to another aspect of the present invention, there is provided a method for preventing or treating an infectious disease, comprising administering the compound represented by formula (Ia) or its pharmacologically acceptable salt, or their solvate to an animal including a human. Animals as candidates for the prevention or treatment are preferably mammals, more preferably humans. The dose of the compound represented by formula (Ia) or its pharmacologically acceptable salt, or their solvate may be appropriately determined by a person having ordinary skill in the art, for example, in consideration of dose regimen, the type of pathogenic bacteria, and the age, sex, and weight of patients, and disease severity of patients. In particular, the dose per day and the number of doses per day may, if necessary, be appropriately varied.

EXAMPLES

The present invention is further illustrated by the following Examples that are not intended as a limitation of the invention.

In the following description, all temperatures are expressed in Celsius degree.

$^1$H-NMR denotes a proton nuclear magnetic resonance spectral method, and $^{13}$C-NMR denotes a carbon nuclear magnetic resonance spectral method. Further, chemical shifts obtained therefrom are expressed in shifts (ppm) from tetramethylsilane (TMS) to a lower magnetic filed side.

MS denotes a mass spectral method, and the results obtained by an electron spray ionization method (ESI), an atmospheric pressure ionization method (API), a fast atom bombardment method (FAB), and a high-performance liquid chromatography-mass analysis method (LCMS) are expressed in m/z (mass/charge).

Rf values in thin-layer chromatographny are values measured with a silica gel plate of ART5715 manufactured by Merck, and a developing solvent, which gave the Rf values, are described within the parentheses.

In the following structural formulae, Bn represents benzyl, Ac acetyl, Ph phenyl, Ts p-toluenesulfonyl, and Cbz benzyloxycarbonyl.

Example 1

Production of 2-hydroxyarbekacin

[Chemical formula 43]

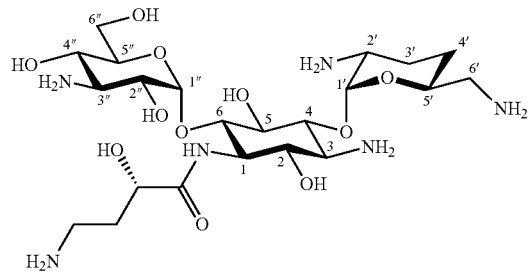

(I)

Production Step 1-1

Methyl 3-azido-3-deoxy-4,6-O-isopropylidene-D-glucopyranoside

[Chemical formula 44]

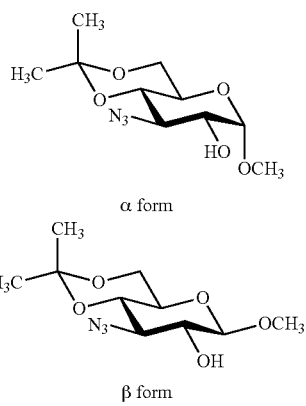

Methyl 3-azido-3-deoxy-D-glucopyranoside (32.7 g) synthesized according to the description of the method of C. B. Barlow et al. (J. Chem. Soc., Abstracts pp. 3870-3871, (June), (1965)) was dissolved in 330 mL of N,N-dimethylformamide. 2,2-Dimethoxypropane (26.8 mL) and 1.92 g of p-toluenesulfonic acid were added to the solution, and the mixture was stirred at 50° C. Three hr after the start of the stirring, 26.8 mL of 2,2-dimethoxypropane was further added to the reaction solution; after 5.5 hr, 2.10 g of p-toluenesulfonic acid was further added to the reaction solution; after 6.5 hr, 17.9 mL of 2,2-dimethoxypropane was further added to the reaction solution; and after 24 hr, 16.2 mL of triethylamine was added under ice cooling to the reaction solution, and the mixture was concentrated to dryness with a vacuum pump. Chloroform (1.5 L) was added to the residue. The solution was washed twice with 500 mL of a saturated aqueous sodium bicarbonate solution and was further washed twice with 500 mL of saturated brine, was dried over Glauber's salt, and was concentrated to dryness to give the title compound (a mixture of an α form and a β form, 36.3 g, yield 96%) as a brown syrup.

ESIMS: m/z 282 [M+Na]$^+$

α Form $^1$H-NMR (CDCl$_3$): δ 4.74 (d, 1H, J=4 Hz), 3.88 (dd, 1H, J=5, 10 Hz), 3.72 (t, 1H, J=10, 10 Hz), 3.65 (dddd 1H, J=5, 9, 10 Hz), 3.61 (t, 1H, J=10, 10 Hz), 3.55 (dt, 1H, J=4, 10, 10 Hz), 3.45 (s, 3H), 3.47 (t, 1H, J=10, 10 Hz), 2.35 (d, 1H, J=10 Hz), 1.51 (s, 3H), 1.44 (s, 3H).

β Form $^1$H-NMR (CDCl$_3$): δ 4.27 (d, 1H, J=8 Hz), 3.95 (dd, 1H, J=5, 10 Hz), 3.78 (t, 1H, J=10, 10 Hz), 3.64 (m, 1H), 3.56 (t, 1H, J=10, 10 Hz), 3.55 (s, 3H), 3.50 (t, 1H, J=10, 10 Hz), 3.37 (dd, 1H, J=8, 10 Hz), 2.67 (br. s, 1H), 1.51 (s, 3H), 1.44 (s, 3H).

Production Step 1-2

Methyl 3-azido-2-O-benzyl-3-deoxy-4,6-O-isopropylidene-D-glucopyranoside

[Chemical formula 45]

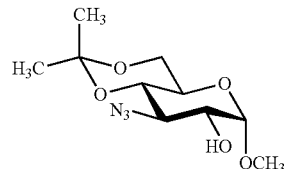

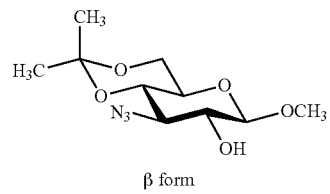

The above compound (46.0 g) product in production step 1-1 was dissolved in 690 mL of N,N-dimethylformamide. Sodium hydride 11.4 g (60% oil suspension) was added to the solution with stirring under ice cooling and a nitrogen atmosphere, and the mixture was further stirred under ice cooling and a nitrogen atmosphere for 30 min. Benzyl bromide (27.4 mL) was added to the reaction solution, and the mixture was stirred under a nitrogen atmosphere at room temperature for 1.5 hr. The reaction solution was then ice cooled and was adjusted to pH 4 to 5 by the addition of a 50% aqueous acetic acid solution. The reaction mixture was then concentrated to dryness, and 2.0 L of chloroform was added thereto. The solution was washed twice with 500 mL of a saturated aqueous sodium bicarbonate solution and was washed once with 500 mL of water. The washed solution was dried over Glauber's salt and was concentrated to dryness to give 73.4 g of a crude product. The crude product was purified by column chromatography on silica gel (hexane:ethyl acetate=7:1 to 3:1) using 350 g of a neutral silica gel to give the title compound (a mixture of an α form and a β form: 55.1 g, yield 89%).

ESIMS: m/z 372 [M+Na]$^+$

α Form $^1$H-NMR (CDCl$_3$): δ 7.30-7.40 (m, 5H), 4.70-4.90 (ABq, 2H, Jgem=12 Hz), 4.52 (d, 1H, J=4 Hz), 3.85 (dd, J=2, 10 Hz), 3.82 (t, 1H, J=10, 10 Hz), 3.66 (t, 1H, J=10, 10 Hz), 3.65 (t, 1H, J=10, 10 Hz), 3.36 (s, 3H), 3.39 (dt, 1H, J=2, 10, 10 Hz), 3.37 (dd, 1H, J=4, 10 Hz), 1.47 (s, 3H), 1.43 (s, 3H).

β Form
$^1$H-NMR (CDCl$_3$): δ 7.30-7.40 (m, 5H), 4.71-4.88 (ABq, 2H, Jgem=12 Hz), 4.38 (d, 1H, J=8 Hz), 3.93 (dd, J=5, 10 Hz), 3.75 (t, 1H, J=10, 10 Hz), 3.56 (s, 3H), 3.51 (t, 1H, J=10, 10 Hz), 3.45 (t, 1H, J=10, 10 Hz), 3.27 (dd, 1H, J=8, 10 Hz), 3.26 (dt, 1H, J=5, 10, 10 Hz), 1.49 (s, 3H), 1.44 (s, 3H).

Production Step 1-3

Methyl 3-azido-2-O-benzyl-3-deoxy-D-glucopyranoside

[Chemical formula 46]

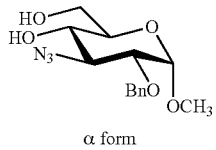
α form

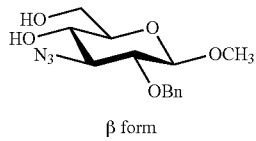
β form

An 80% aqueous acetic acid solution (186 mL) was added to 37.3 g of the compound produced in production step 1-2. A reaction was allowed to proceed at 80° C., and, 30 min after the start of the reaction, the reaction solution was cooled to room temperature and was concentrated to dryness to give 32.9 g of the title compound (a mixture of an α form and a β form) at a quantitative yield.

ESIMS: m/z 332 [M+Na]$^+$

α Form
$^1$H-NMR (CDCl$_3$): δ 7.30-7.45 (m, 5H), 4.63-4.80 (ABq, 2H, Jgem=12 Hz), 4.57 (d, 1H, J=3.5 Hz), 3.78-3.85 (m, 2H), 3.63 (dt, 1H, J=4, 4, 10 Hz), 3.44 (t, 1H, J=10, 10 Hz), 3.40 (dd, 1H, J=3.5, 10 Hz), 3.38 (t, 1H, J=10, 10 Hz), 3.37 (s, 3H), 2.44 (d, 1H, J=3.5 Hz), 1.82 (dd, 1H, J=6, 7.5 Hz).

β Form
$^1$H-NMR (CDCl$_3$): δ 7.30-7.45 (m, 5H), 4.71-4.92 (ABq, 2H, Jgem=12 Hz), 4.39 (d, 1H, J=8 Hz), 3.91 (m, 1H), 3.78-3.85 (m, 2H), 3.58 (s, 3H), 3.45 (t, 1H, J=10, 10 Hz), 3.39 (t, 1H, J=10, 10 Hz), 3.27 (dd, 1H, J=8, 10 Hz), 2.50 (d, 1H, J=2.5 Hz), 1.97 (dd, 1H, J=6, 7.5 Hz).

Production Step 1-4

1,4,6-Tri-O-acetyl-3-azido-2-O-benzyl-3-deoxy-D-glucopyranose

[Chemical formula 47]

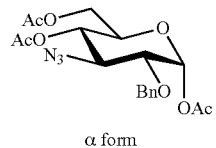
α form

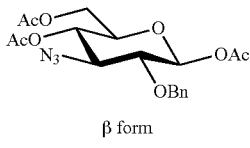
β form

Acetic acid-acetic anhydride-concentrated sulfuric acid (50:50:1) (164 mL) was added to and dissolved in 32.8 g of the compound produced in production step 1-3 with an ultrasonic cleaner, and a reaction was allowed to proceed at room temperature for 5 hr. The reaction solution was dropped with vigorous stirring to 1.7 L of an ice cooled 10% aqueous sodium acetate solution. Chloroform (20 mL) was added four times to the reaction solution, and mixture was vigorously stirred under ice cooling for 20 min. The reaction solution was returned to room temperature and was further vigorously stirred for one hr. The reaction solution was then extracted with 2.5 L of chloroform (once with 900 mL and twice with 800 mL). The chloroform layer was washed once with 500 mL of saturated brine, twice with 500 mL of a saturated aqueous sodium bicarbonate solution, and once with 500 mL of saturated brine. The chloroform layer was further dried over Glauber's salt and was concentrated to dryness to give 48.4 g of a crude product. The crude product thus obtained was purified by column chromatography on silica gel (250 g) (hexane:ethyl acetate=5:1) to give the title compound (a mixture of an α form and a β form: 41.3 g, yield 92%) as a light yellow syrup.

ESIMS: m/z 444 [M+Na]$^+$

α Form
$^1$H-NMR (CDCl$_3$): δ 7.30-7.40 (m, 5H), 6.32 (d, 1H, J=4 Hz), 4.90 (t, 1H, J=10, 10 Hz), 4.62-4.71 (ABq, 2H, Jgem=12 Hz), 4.22 (dd, 1H, J=5, 13 Hz), 4.01 (dd, 1H, J=2.5, 10 Hz), 3.98 (m, 1H), 3.88 (t, 1H, J=10, 10 Hz), 3.58 (dd, 1H, J=4, 10 Hz), 2.06, 2.12, 2.17 (each s, each 3H).

β Form
$^1$H-NMR (CDCl$_3$): δ 7.30-7.40 (m, 5H), 5.62 (d, 1H, J=9 Hz), 4.91 (t, 1H, J=10, 10 Hz), 4.72-4.82 (ABq, 2H, Jgem=12 Hz), 4.25 (dd, 1H, J=5, 13 Hz), 3.99 (dd, 1H, J=2.5, 13 Hz), 3.74 (ddd, 1H, J=2.5, 5, 10 Hz), 3.66 (t, 1H, J=10, 10 Hz), 3.59 (dd, 1H, J=9, 10 Hz), 2.07, 2.12, 2.22 (each s, each 3H).

Production Step 1-5a 4,6-Di-O-acetyl-3-azido-2-O-benzyl-1-bromo-3-deoxy-α-D-glucopyranose

[Chemical formula 48]

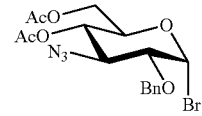

The compound (347 mg) synthesized in production step 1-4 was dissolved in a mixed solution composed of 6.2 mL of methylene chloride and 0.69 mL of ethyl acetate. Titanium tetrabromide (605 mg) was added to the mixed solution with stirring under ice cooling, and the mixture was stirred at room temperature for 14.5 hr. The reaction solution was ice cooled, and 30 mL of ice cooled methylene chloride was added thereto. The solution was washed eight times with 15 mL of ice cooled water until the water layer had pH 7. The solution was then dried over Glauber's salt under ice cooling and was concentrated to dryness to give the title compound (352 mg, yield: 97%) as a light yellow syrup.

$^1$H-NMR (CDCl$_3$): δ 7.20-7.45 (m, 5H), 6.32 (d, 1H, J=3.5 Hz), 4.92 (t, 1H, J=10, 10 Hz), 4.68-4.74 (ABq, 2H, Jgem=12 Hz), 4.27 (dd, 1H, J=4.5, 12.5 Hz), 4.17 (ddd, 1H, J=2.5, 4.5, 10 Hz), 4.03 (dd, 1H, J=2.5, 12.5 Hz), 3.98 (t, 1H, J=10, 10 Hz), 3.43 (dd, 1H, J=3.5, 10 Hz), 2.13 (s, 3H), 2.06 (s, 3H).

Production Step 1-5b

4,6-Di-O-acetyl-3-azido-2-O-benzyl-3-deoxy-1-thiopheny 1-α-D-glucopyranose

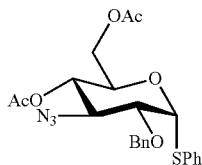

[Chemical formula 49]

The compound (19.9 g) produced in production step 1-4 was dissolved in 200 mL of methylene chloride. Trimethylsilylthiophenol (26.8 mL) and 11.0 mL of trimethylsilyltriflate were added to the solution, and the mixture was refluxed. The reaction mixture was ice cooled 41 hr after the start of the reflux. Further, ice cooled chloroform (1.8 L) was added thereto. The reaction mixture was then washed three times with 1 L of an ice cooled 5% aqueous NaOH solution and twice with 1 L of ice cooled water. The reaction mixture was then dried over Glauber's salt, was concentrated to dryness to give a crude product (22.1 g). The crude product was then dissolved in 20 mL of ethyl acetate. Hexane (120 mL) was further added to the solution for recrystallization. The resultant crystal was washed with ice cooled ethyl acetate:hexane (1:9) to give the title compound (17.7 g, yield 79%). Further, the mother liquor and the wash liquid for the crystal were combined and were concentrated to dryness to give the title compound (4.3 g).

ESIMS: m/z 494 [M+Na]$^+$ $^1$H-NMR (CDCl$_3$): δ 7.20-7.48 (m, 10H), 5.59 (d, 1H, J=5 Hz), 4.83 (t, 1H, J=10, 10 Hz), 4.68-4.78 (ABq, 2H, Jgem=12 Hz), 4.46 (ddd, 1H, J=2.5, 5, 10 Hz), 4.22 (dd, 1H, J=5, 12 Hz), 3.96 (t, 1H, J=2.5, 12 Hz), 3.86 (t, 1H, J=10, 10 Hz), 3.79 (dd, 1H, J=5, 10 Hz), 2.13 (s, 3H), 1.99 (s, 3H).

Production Step 1-6

3',4'-Dideoxy-2-hydroxyneamine

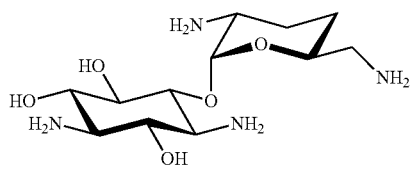

[Chemical formula 50]

Process A: 2-Hydroxygentamicin C1a (18.0 g) represented by formula (II) was produced according to the description of Japanese Patent Laid-Open No. 108041/1976 and was purified. Next, 3 M HCl (360 mL) was added to the resultant 2-hydroxygentamicin C1a, and the mixture was refluxed for 1.5 hr. The reaction solution was returned to room temperature, was then ice cooled, was adjusted to pH about 6.8 by the addition of 4 M NaOH, was diluted with 1.8 L of water, and was added into an Amberlite CG-50 (previously equilibrated with 0.005 M aqueous ammonia) 500 mL column. This column was washed with 1 L of 0.005 M aqueous ammonia. Elution was carried out with 2 L of 0.1 M aqueous ammonia and 2 L of 0.3 M aqueous ammonia. Fractions containing the title compound were combined and were concentrated to dryness to give 6.1 g of the title compound. Fractions containing impurities were again purified by the Amberlite CG-50 column to give 0.6 g of the title compound. Thus, 6.7 g in total of the title compound (monocarbonate, yield 72%) was obtained.

Process B: 2-Hydroxygentamicin C1a (600 g) represented by formula (II) was produced and was purified according to the description of Japanese Patent Laid-Open No. 108041/1976. Next, 2-hydroxygentamicin C1a (300 g, 483 mmol as 2.5 carbonate) was dissolved in 3 N HCl (3 L), and the solution was stirred at 95° C. for 70 min. After standing to cool, the solution was ice cooled to 10° C. and was neutralized and adjusted to pH 6.88 by the addition of 5 N NaOH. Further, the same reaction was again carried out using 2-hydroxygentamicin C1a (300 g, 483 mmol as 2.5 carbonate). The resultant two reaction mixtures were combined and were purified with Amberlite CG-50 (NH$_4$ type; equilibrated with 0.005 M NH$_3$, 10 L). Elution solvent: 0.1 M→0.2 M→0.3 M NH$_3$. The purified product was lyophilized to give the title compound (335.9 g; 781 mmol as dicarbonate; yield 81%).

ESIMS: m/z 329 [M+Na]$^+$ $^1$H-NMR (26% ND$_3$-D$_2$O: δ 5.09 (d, 1H, J=3.5 Hz), 3.82 (m, 1H), 3.56 (t, 1H, J=10, 10 Hz), 3.30 (t, 1H, J=10, 10 Hz), 3.35 (t, 1H, J=10, 10 Hz), 3.08 (t, 1H)=10, 10 Hz), 2.82 (dt, 1H, J=3.5, 3.5, 12 Hz), 2.78 (t, 1H, J=10, 10 Hz), 2.58-2.68 (m, 2H), 2.63 (t, 1H, J=10, 10 Hz), 1.67-1.79 (m, 2H), 1.60 (dq, 1H, J=4, 12, 12, 12 Hz), 1.36 (dq, 1H, J=4, 12, 12, 12 Hz).

Production Step 1-7

3',4'-Dideoxy-2-hydroxyl-1,3,2',6'-tetra-N-tosyl-neamine

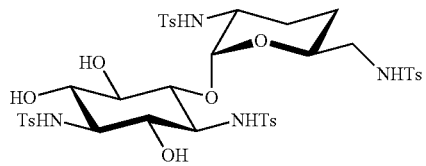

[Chemical formula 51]

The compound (6.7 g) produced in production step 1-6 was dissolved in 67 mL of water. Sodium carbonate (11.6 g) was added to the solution, and 134 mL of dioxane was further added. p-Toluenesulfonyl chloride (20.8 g) was added to the mixture under ice cooling, and the mixture was vigorously stirred for 15 min under ice cooling. The solution was returned to room temperature and was vigorously stirred overnight. Dioxane (134 mL) was then added to the reaction solution; after 42.5 hr, 3.9 g of sodium carbonate was added to the reaction solution; after 88 hr, 3.5 g of p-toluenesulfonyl chloride was added to the reaction solution; and after 112.5 hr, 8.5 mL of concentrated aqueous ammonia was added to the reaction solution, and the mixture was stirred for 30 min. The reaction mixture was concentrated to dryness. Ethyl acetate (700 mL) was added to the residue, and the mixture was washed twice with 300 mL of water, was dried over Glauber's salt, and was then concentrated to dryness. The crude product was purified by column chromatography on silica gel (chloroform:methanol=20:1) on 250 g of silica gel to give 3.47 g of the title compound. A fraction containing impurities was also subjected to column chromatography on silica gel to give 7.05 g of the title compound. As a result, 10.52 g (total amount; yield 63%) of the title compound was produced.

ESIMS: m/z 945 [M+Na]+

$^1$H-NMR (Pyridine-d5): δ 9.20 (d, 1H, J=7 Hz), 9.15 (d, 1H, J=8 Hz), 8.80 (d, 1H, J=8 Hz), 8.46 (t, 1H, J=6, 6 Hz), 7.90-8.18 (m, 8H), 7.00-7.15 (m, 8H), 5.97 (d, 1H, J=3 Hz), 5.09 (m, 1H), 4.14 (t, 1H, J=10, 10 Hz), 4.07 (t, 1H, J=10, 10 Hz), 3.91 (t, 1H, J=10, 10 Hz), 3.79-3.86 (m, 2H), 3.74 (t, 1H, J=10, 10 Hz), 3.73 (m, 1H), 3.30-3.47 (m, 2H), 2.40 (dq, 1H, J=5, 12, 12, 12 Hz), 2.17 (s, 6H), 2.16 (s, 3H), 2.11 (s, 3H), 1.77 (m, 1H), 1.58-1.72 (m, 2H).

Production Step 1-8

4",6"-Di-O-acetyl-3"-azido-2"-O-benzyl-3"-deoxy-2-hydroxyl-1,3,2',6'-tetra-N-tosyldibekacin

[Chemical formula 52]

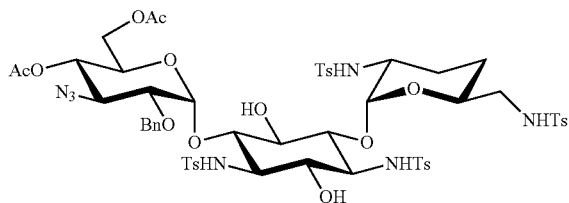

Process A: A solution of 352 mg of the compound produced in production step 1-5a in 7.3 mL of 1,2-dichloroethane was added to 363 mg of the compound produced in production step 1-7. Drierite (1070 mg) was added thereto, and the mixture was stirred at room temperature for 30 min. Mercuric cyanide (397 mg) was added to the reaction solution, and the mixture was stirred under light shielding at 60° C. until the compound produced in production step 1-5a disappeared when the reaction was traced by TLC. The reaction solution was returned to room temperature and was filtered through Celite. The insolubles were washed with 73 mL of chloroform. The filtrate and the wash liquid were combined, were washed three times with 36 mL of a saturated aqueous sodium bicarbonate solution, three times with 36 mL of a 10% aqueous sodium iodide solution and twice with 36 mL of water in that order, were dried over a Glauber's salt, and were concentrated to dryness. The residue was purified by column chromatography on silica gel (chloroform:ethyl acetate=5:2) on 36 g of silica gel to give the title compound (190 mg, yield 37.5%).

Process B: The compound (10.52 g) produced in production step 1-7 and the compound (9.67 g) produced in production step 1-5b were dissolved in 210 mL of methylene chloride. A molecular sieves 4 A powder (31.6 g) was added to the solution, and the mixture was stirred at room temperature for 30 min. Next, a solution of 5.54 g of N-iodosuccinimide and 0.55 mL of trifluoromethanesulfonic acid in 9.45 mL of methylene chloride was added to the reaction solution with stirring at −20° C. under light shielding. Further, the mixture was stirred at −20° C. for 30 min under light shielding. Next, 3.4 mL of triethylamine was added to the reaction solution, and the mixture was filtered through Celite, and the insolubles were washed with 1.8 L of chloroform. Next, the filtrate and the wash liquid were combined, were washed twice with 1 L of a saturated aqueous sodium bicarbonate solution, twice with 1 L of a 10% aqueous sodium thiosulfate solution, and twice with 500 mL of water in that order, were dried over a Glauber's salt, and were concentrated to dryness to give 20.2 g of a crude product. Next, the crude product was purified by column chromatography on 500 g of silica gel (chloroform:ethyl acetate=5:2) to give the title compound (5.4 g, yield 37%).

Rf value 0.68 (chloroform:ethyl acetate=2:3)

ESIMS: m/z 1306 [M+Na]+

$^1$H-NMR (Pyridine-d5): δ 9.22 (d, 1H, J=7.5 Hz), 8.82 (d, 1H, J=8.5 Hz), 8.73 (t, 1H, J=6, 6 Hz), 8.25 (d, 1H, J=8.5 Hz), 7.8-8.1 (m, 10H), 7.0-7.45 (m, 11H), 6.75 (d, 1H, J=3 Hz), 6.09 (d, 1H, J=2 Hz), 5.51 (ABq, 1H, Jgem=11 Hz), 5.23 (t, 1H, J=10, 10 Hz), 5.03 (m, 1H), 4.96 (m, 1H), 4.93 (ABq, 1H, Jgem=11 Hz), 4.41 (t, 1H, J=10, 10 Hz), 4.38 (dd, 1H, J=4, 12 Hz), 4.23 (m, 1H), 4.07-4.21 (m, 5H), 3.83 (dd, 1H, J=3, 10 Hz), 3.78 (t, 1H, J=9, 9 Hz), 3.72 (m, 1H), 3.27 (m, 1H), 3.17 (m, 1H), 2.35 (m, 1H), 2.21 (s, 3H), 2.20 (s, 6H), 2.19 (s, 3H), 2.03 (s, 3H), 2.01 (s, 3H), 1.65 (m, 1H), 1.45-1.60 (m, 2H).

Production Step 1-9

3"-Azido-2"-O-benzyl-3"-deoxy-2-hydroxyl-1,3,2',6'-tetra-N-tosyldibekacin

[Chemical formula 53]

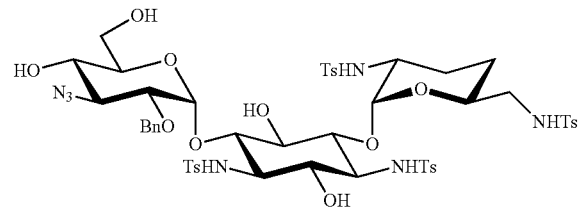

A 0.1% solution (118 mL) of sodium methoxide in methanol was added to 5.91 g of the compound produced in production step 1-8, and the mixture was allowed to react at room temperature. A 28% solution (1.74 mL) of sodium methoxide in methanol was added to the reaction solution 50 min after the start of the reaction. After 1.5 hr, the reaction solution was neutralized and adjusted to pH 6 to 7 with Dowex 50 W×2 (H+ form, 200-400 mesh, substituted with MeOH). Next, the resin was removed from the reaction solution by filtration, and the insolubles were washed five times or more with methanol. The filtrate and the wash liquid were combined and were concentrated to dryness to give 5.2 g of the crude title compound. This compound as such was used in the next reaction.

Rf value 0.39 (chloroform:ethyl acetate=2:3)

ESIMS: m/z 1222 [M+Na]+

Production Step 1-10

2-Hydroxydibekacin

[Chemical formula 54]

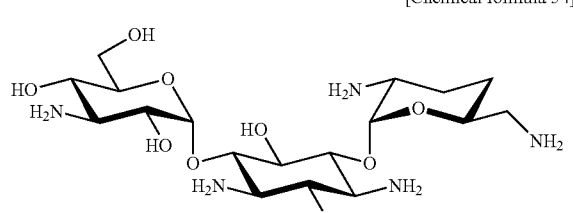

Liquid ammonia (about 10 mL) was stored at −50° C. in an egg-plant type flask containing 45.7 mg of the compound produced in production step 1-9. Next, 70 mg of metallic sodium was added to the egg-plant type flask at −50° C., and the mixture was vigorously stirred with a glass stirrer bar for 2 hr. Methanol was slowly added to the egg-plant type flask until the color of radicals disappeared. The mixture was returned to room temperature to evaporate ammonia and was finally concentrated to dryness with an evaporator. Water (3 mL) was added to the egg-plant type flask, and the contents of the flask were adjusted to pH 4 to 5 with Dowex 50 W×2 ($H^+$ form). The contents of the flask together with the resin were added to a column paced with 2 mL of the same resin. The column was washed with 20 mL of water, was eluted with 1 M aqueous ammonia. Ninhydrin positive fractions were combined and were concentrated to dryness to give 20.1 mg of a crude product. This was brought to an aqueous solution (10 mL) which was then added to a CM-Sephadex C-25 column (equilibrated with 0.005 M aqueous ammonia, 10 mL). The column was washed with water (10 mL). Next, elution was carried out while successively changing the concentration of aqueous ammonia from 0.05M (50 mL) to 0.2 M (100 mL, 2 mL cut), and the corresponding fraction was concentrated to dryness to give 16.4 mg of the title compound (monocarbonate•monohydrate, yield 79%).

Rf value 0.35 (1-butanol:ethanol:chloroform:17% aqueous ammonia=4:7:2:7).

ESIMS: m/z 490 [M+Na]$^+$ $^1$H-NMR (26% $ND_3$-$D_2O$): δ 5.12 (d, 1H, J=3.5 Hz), 5.01 (d, 1H, J=4 Hz), 3.88 (m, 1H), 3.83 (m, 1H), 3.75 (dd, 1H, J=2.5, 12 Hz), 3.68 (dd, 1H, J=5, 12 Hz), 3.66 (t, 1H, J=10, 10 Hz), 3.46 (dd, 1H, J=4, 10 Hz), 3.35 (t, 1H, J=10, 10 Hz), 3.28 (t, 1H, J=10, 10 Hz), 3.27 (t, 1H, J=10, 10 Hz), 3.10 (t, 1H, J=10, 10 Hz), 2.99 (t, 1H, J=10, 10 Hz), 2.83 (t, 1H, J=10, 10 Hz), 2.80 (m, 1H), 2.79 (t, 1H, J=10, 10 Hz), 2.66 (dd, 1H, J=4.5, 13 Hz), 2.62 (dd, 1H, J=7, 13 Hz), 1.68-1.77 (m, 2H), 1.60 (m, 1H), 1.37 (m, 1H).

$^{13}$C-NMR (26% $ND_3$-$D_2O$): δ 102.62, 101.41, 85.70, 84.53, 75.36, 74.00, 73.67, 72.89, 71.83, 70.35, 61.35, 57.67, 56.81, 55.65, 51.35, 46.60, 28.97, 27.45.

Production Step 1-11

2',6'-Di-N-benzyloxycarbonyl-2-hydroxydibekacin

[Chemical formula 55]

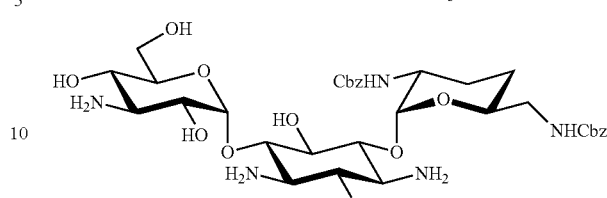

Nickel acetate tetrahydrate (1136 mg) was added to the compound (625 mg; as calculated as monocarbonate•monohydrate) produced in production step 1-10. Methanol (25 mL) was added to thereto, and the mixture was treated with an ultrasonic cleaner to give a homogeneous solution. N-Benzyloxycarbonyloxysuccinimide (626 mg) was added little by little to the solution under ice cooling over a period of about 2 min. The mixture was stirred under ice cooling for one hr, was returned to room temperature, and was further stirred for 2.5 hr. Next, 57 mg of N-benzyloxycarbonyloxysuccinimide was added to the reaction solution under ice cooling, was returned to room temperature, and was further stirred for 2 hr. The reaction solution was concentrated to dryness. Concentrated aqueous ammonia (30 mL) saturated with sodium chloride was added to the residue, and the mixture was extracted three times with 20 mL of 1-butanol. The butanol layer thus obtained was concentrated to dryness. N,N-Dimethylformamide was added to 1423 mg of the residue and was filtered through Celite. The substance on the Celite was washed with N,N-dimethylformamide (20 mL×1, 10 mL×4). The filtrate and the wash liquid were concentrated to dryness to give 1222 mg of a crude product.

Rf value 0.60 (1-butanol:ethanol:chloroform:17% aqueous ammonia=4:7:2:7)

ESIMS: m/z 758 [M+Na]

$^1$H-NMR (Pyridine-d5): δ 8.35 (br. s, 1H), 7.90 (d, 1H, J=7.5 Hz), 7.15-7.55 (m, 10H), 5.62 (d, 1H, J=3 Hz), 5.41 (d, 1H, J=3 Hz), 5.33 (s, 2H), 5.30 (ABq, 1H, Jgem=12 Hz), 5.14 (ABq, 1H, Jgem=12 Hz), 4.64 (m, 1H), 4.44 (dd, 1H, J=2, 12 Hz), 4.42 (m, 1H), 4.28 (dd, 1H, J=5, 12 Hz), 4.24 (t, 1H, J=10, 10 Hz), 4.20 (dd, 1H, J=3, 10 Hz), 4.05 (m, 1H), 4.04 (t, 1H, J=10, 10 Hz), 3.90 (t, 1H, J=10, 10 Hz), 3.85 (t, 1H, J=10, 10 Hz), 3.68 (t, 1H, J=10, 10 Hz), 3.60 (t, 1H, J=10, 10 Hz), 3.52 (m, 1H), 3.39 (m, 1H), 3.29 (t, 1H, J=10, 10 Hz), 3.11 (t, 1H, J=10, 10 Hz), 2.05 (m, 1H), 1.89 (dq, 1H, J=3.5, 13, 13, 13 Hz), 1.64 (m, 1H), 1.43 (q, 1H, J=13, 13, 13 Hz).

Production Step 1-12

2',6'-Di-N-benzyloxycarbonyl-2-hydroxy-3"-N-trifluoroacetyldibekacin

[Chemical formula 56]

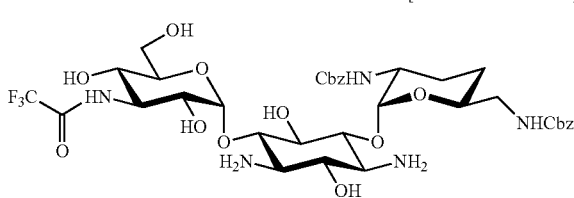

The crude product (1222 mg) produced in production step 1-11 was dissolved in 17 mL of anhydrous N,N-dimethylformamide. Ethyl trifluoroacetate (0.15 mL) was added to the solution with stirring under ice cooling. The mixture was returned to room temperature and was stirred for 8 hr. The reaction solution was concentrated to dryness to give 1416 mg of the product.

Rf value 0.42 (lower layer part of a solution of chloroform: methanol: 15 M aqueous ammonia (concentrated aqueous ammonia)=1:1:1 was used)

$^1$H-NMR (Pyridine-d5): δ 10.65 (d, 1H, J=9 Hz), 8.35 (br. s, 1H), 7.89 (d, 1H, J=8.5 Hz), 7.10-7.55 (m, 10H), 5.70 (d, 1H, J=3 Hz), 5.41 (d, 1H, J=3 Hz), 5.33 (s, 2H), 5.30 (ABq, 1H, Jgem=12 Hz), 5.26 (ABq, 1H, Jgem=12 Hz), 5.18 (m, 1H), 4.77 (m, 1H), 4.58 (t, 1H, J=10, 10 Hz), 4.50 (dd, 1H, J=3, 10 Hz), 4.31-4.46 (m, 3H), 4.18 (t, 1H, J=10, 10 Hz), 4.04 (m, 1H), 3.96 (t, 1H, J=10, 10 Hz), 3.82 (t, 1H, J=10, 10 Hz), 3.71 (t, 1H, J=10, 10 Hz), 3.51 (m, 1H), 3.40 (m, 1H), 3.31 (t, 1H, J=10, 10 Hz), 3.10 (t, 1H, J=10, 10 Hz), 2.05 (m, 1H), 1.89 (m, 1H), 1.64 (m, 1H), 1.43 (m, 1H).

Production Step 1-13

1-N-(4-Benzyloxycarbonylamino-2-(S)-hydroxybutyryl)-2',6'-di-N-benzyloxycarbonyl-2-hydroxy-3''-N-trifluoroacetyldibekacin

[Chemical formula 57]

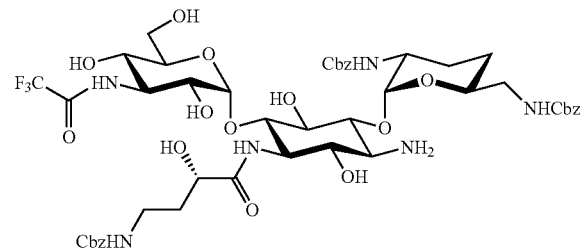

The product (438 mg) produced in production step 1-12 was dissolved in 6.2 mL of tetrahydrofuran. A solution (2 mL) of 149 mg of an (S)-4-N-benzyloxycarbonylamino-2-hydroxybutyric acid succinimide ester synthesized according to a report of Kawaguchi et al. (Journal of Antibiotics, Vol. 25, pp. 695 to 708 (1972)) in tetrahydrofuran was added dropwise to the solution with stirring under ice cooling over a period of 2 min, and the mixture was returned to room temperature and was stirred. A solution (2 mL) of 149 mg of an N-benzyloxycarbonyl-4-amino-2-(S)-hydroxybutyrylic acid succinimide ester in tetrahydrofuran was added to the reaction solution with stirring under ice cooling 19 hr after the start of stirring, and the mixture was returned to room temperature and was stirred. After 20.5 hr, the reaction solution was concentrated to dryness.

Ethyl acetate (70 mL) was added to the residue, and the mixture was washed twice with 14 mL of a saturated aqueous sodium bicarbonate solution and twice with 14 mL of water and was concentrated to dryness to give 571 mg of the reaction mixture.

Rf value 0.59 (lower part of a solution of chloroform: methanol:15 M aqueous ammonia (concentrated aqueous ammonia)=1:1:1 was used)

Production Step 1-14

2-Hydroxyarbekacin

[Chemical formula 58]

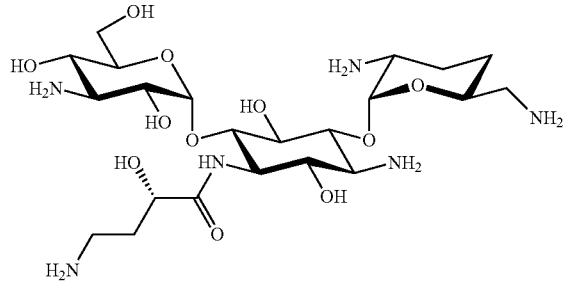

Tetrahydrofuran (22.8 mL) and 17.8 mL of 3.5 M aqueous ammonia were added to 571 mg of the reaction mixture produced in production step 1-13, and the mixture was stirred at room temperature for 20 hr. The reaction solution was concentrated to dryness. Tetrahydrofuran-acetic acid-water (4:1:1) (22 mL) was added to 624 mg of the residue. Further, 12 drops of a suspension of palladium black in water was added, and the mixture was stirred at the atmospheric pressure for 6 hr while blowing a hydrogen gas into the system. Next, palladium black was removed from the reaction solution by filtration. The removed palladium black was washed with water, and the filtrate and the wash liquid were combined and were concentrated to dryness. 2 M aqueous ammonia (15 mL) was added to the residue, and the mixture was allowed to stand at room temperature overnight. The insolubles were removed by filtration through a cotton stopper, followed by concentration to dryness to give 467 mg of a crude product. The crude product was dissolved in water to give 50 mL of an aqueous solution, and the aqueous solution added to a CM-Sephadex C-25 column (equilibrated with 0.005 M aqueous ammonia, 50 mL). The column was washed with 100 mL of 0.005 M aqueous ammonia, and elution was carried out with aqueous ammonia with 0.05 M (250 mL) to 0.5 M (500 mL) and further 0.75 M (500 mL). The corresponding fractions were concentrated to give 39.1 mg of the title compound: 2-hydroxyarbekacin.

$^1$H-NMR (26% ND$_3$-D$_2$O): δ 5.13 (d, 1H, J=3.5 Hz), 5.03 (d, 1H, J=4 Hz), 4.16 (dd, 1H, J=4, 9.5 Hz), 3.98 (m, 1H), 3.83-3.90 (m, 2H), 3.65-3.77 (m, 4H), 3.37 (t, 1H, J=10, 10 Hz), 3.34 (t, 1H, J=10, 10 Hz), 3.32 (dd, 1H, J=4, Hz), 3.25 (t, 1H, J=10, 10 Hz), 2.97 (t, 1H, J=10, 10 Hz), 2.86 (t, 1H, J=10, 10 Hz), 2.82 (m, 1H), 2.70-2.78 (m, 2H), 2.65 (dd, 1H, J=5, 13 Hz), 2.62 (dd, 1H, J=7, 13 Hz), 1.86-1.96 (m, 1H), 1.69-1.80 (m, 3H), 1.61 (dq, 1H, J=4, 13, 13, 13 Hz), 1.37 (dq, 1H, J=4, 13, 13, 13 Hz).

$^{13}$C-NMR (26% ND$_3$-D$_2$O): δ 177.84, 102.09, 98.99, 83.65, 78.17, 75.41, 72.87, 72.23, 71.71, 71.28, 70.45, 69.81, 60.79, 56.60, 56.15, 54.88, 50.71, 46.02, 38.26, 37.23, 28.39, 26.94.

Example 2

2-Hydroxyarbekacin 2.5 sulfate trihydrate

[Chemical formula 59]

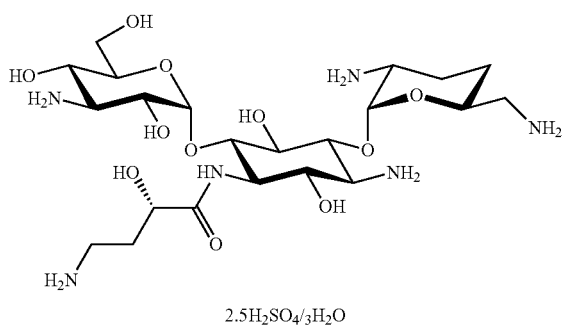

2.5H$_2$SO$_4$/3H$_2$O

The compound (2-hydroxyarbekacin; 126.8 mg) represented by formula (I) produced in production step 1-14 of Example 1 was brought to an aqueous solution. The aqueous solution was adjusted to pH 7.0 by the addition of 0.1 M sulfuric acid and was lyophilized to give 147.3 mg of 2.5 sulfate (trihydrate) of the title compound.

Calcd. for C$_{22}$H$_{44}$N$_6$O$_{11}$·2.5H$_2$SO$_4$·3H$_2$O. C, 30.45; H, 6.39; N, 9.67.

Found, C, 30.41; H, 6.45; N, 9.46.

Example 3

Production of 2-hydroxyarbekacin

[Chemical formula 60]

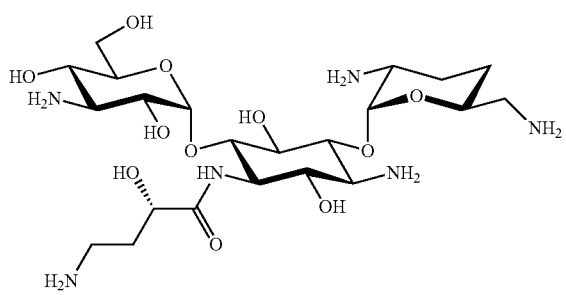

Production Step 3-1

1,3,2',6'-Tetra-N-benzyloxycarbonyl-3',4'-dideoxy-2-hydroxyneamine

[Chemical formula 61]

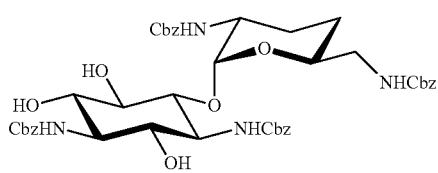

Process A: The compound (16.5 g, 38.3 mmol: calculated as dicarbonate) produced in production step 1-6 was dissolved in water (83 ml). Dimethoxyethane (165 ml) was added to the solution, and the mixture was then stirred. N-Benzyloxycarbonyloxysuccinimide (66.8 g, 268 mmol) was added thereto, triethylamine (56.0 ml, 402 mmol) was then added, and the mixture was stirred overnight (heat up to about 45° C. was generated). Ethyl acetate (490 ml) and water (83 mL) were added to the reaction solution followed by separation. The organic layer was washed with a saturated aqueous sodium hydrogencarbonate solution (247 mL) and a 10% aqueous sodium thiosulfate solution (247 mL) in that order. The organic layer was dried over anhydrous magnesium sulfate, was filtered, and was then concentrated under the reduced pressure. Methanol (133 ml) was added to the residue (as a foam), and the mixture was stirred on a water bath heated to 60° C. As a result, crystals were precipitated. The mixture was stirred at room temperature overnight (slurry washing). The precipitated crystals were collected by filtration and were dried under the reduced pressure at 40° C. overnight to give the title compound (yield 33.8 g, quantitative).

Process B: The compound (303 g, 704 mmol as dicarbonate) produced in production step 1-6 was dissolved in water (1.5 L), and 1,2-dimethoxyethane (3.0 L) was added to the solution. N-Benzyloxycarbonyloxysuccinimide (1229 g, 4.93 mol, 7.0 eq.) was added thereto, and triethylamine (1013 mL, 7.40 mol, 10.5 eq.) was then added, and the mixture was stirred overnight. Ethyl acetate (9.1 L) and water (1.5 L) were added to the reaction solution, followed by separation. The water layer was again extracted with ethyl acetate: 1,2-dimethoxyethane=3:1 (1.8 L). The organic layers were combined and were washed once with a 5% aqueous sodium hydrogencarbonate solution (4.6 L) and once with a 10% aqueous sodium thiosulfate solution (4.6 L). The organic layer was dried over anhydrous magnesium sulfate, and the solvent was then removed by distillation under the reduced pressure. Methanol (2.4 L) was added to the residue, and the mixture was stirred at room temperature overnight. The precipitated crystal was filtered to give the title compound (619.1 g, 734 mmol, yield 104%).

APIMS: m/z 843 [M+H]$^+$ $^1$H-NMR (Pyridine-d5): δ 7.73 (d, 1H, J=6.9 Hz), 7.12-7.56 (m, 22H), 6.82-6.95 (m, 1H), 5.67 (d, 1H, J=2.9 Hz), 5.12-5.31 (m, 8H), 4.26-4.40 (m, 1H), 3.90-4.30 (m, 7H), 3.35-3.50 (m, 2H), 1.85-2.01 (m, 2H), 1.43-1.65 (m, 2H).

Production Step 3-2

1,3,2',6'-Tetra-N-benzyloxycarbonyl-5,6-O-cyclohexylidene-3',4'-dideoxy-2-hydroxyneamine

[Chemical formula 62]

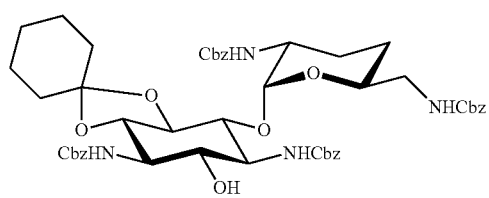

Process A: The compound (2.0 g, 2.4 mmol) produced in production step 3-1 was dissolved in dimethoxyethane (40 mL). 1,1-Dimethoxycyclohexane (0.54 mL, 3.56 mmol) and pyridinium p-toluenesulfonate (PPTS) (0.060 g, 0.24 mmol) were added to the solution, and the mixture was stirred on an oil bath at 110° C. for 2 hr with an apparatus comprising a dropping funnel containing molecular sieves 5 A 1/16 (30 g, 40 mL) and a Dimroth condenser provided on the dropping funnel (internal temperature 85° C.). Ethyl acetate (40 mL) and a saturated aqueous sodium hydrogencarbonate solution (40 mL) were added to the reaction solution, followed by separation. The organic layer was washed with a saturated aqueous NaCl solution and was dried over anhydrous magnesium sulfate and was then concentrated under the reduced pressure. The residue was purified by column chromatography on silica gel (hexane:ethyl acetate=2:1 to 1:3, chloroform:methanol=9:1) to give the title compound (1.75 g, 1.89 mmol, yield 80%).

Process B: The compound (150 g, 178 mmol) produced in production step 3-1 was suspended in 1,2-dimethoxyethane (3.0 L). 1,1-Dimethoxycyclohexane (38.5 g, 267 mmol, 1.5 eq.) and pyridinium p-toluenesulfonate (4.47 g, 17.8 mmol, 0.1 eq.) were added, and the mixture was heated and was refluxed while passing through 1.5 kg of molecular sieves 5 A (1/16) for 4 hr. The reaction mixture was diluted with ethyl acetate (3 L) and was washed once with a 5% aqueous sodium hydrogencarbonate solution (4.6 L) and once with a 10% aqueous sodium thiosulfate solution (3 L). The organic layer was dried over anhydrous magnesium sulfate, and the solvent was then removed by distillation under the reduced pressure. The same reaction was further carried out three more times. The residues were combined and were purified by chromatography on silica gel to give the title compound. Developing solvent=hexane:ethyl acetate=2:1→1:1→1:2→1:3. (557.93 g, 604 mmol, yield 85%).

APIMS: m/z 923 [M+H]$^+$ $^1$H-NMR (Pyridine-d5): δ 7.96 (d, 1H, J=6.2 Hz), 7.68 (d, 1H, J=6.8 Hz), 7.22-7.57 (m, 20H), 6.75-7.05 (m, 2H), 5.57 (s, 1H), 5.12-5.35 (m, 8H), 3.96-4.45 (m, 6H), 3.92 (t, 1H, J=10, 10 Hz), 3.79 (t, 1H, J=10, 10 Hz), 3.30-3.47 (m, 2H), 1.77-2.00 (m, 2H), 1.45-1.70 (m, 10H), 1.16-1.35 (m, 2H).

Production Step 3-3

2-Benzyloxy-1,3,2',6'-tetra-N-benzyloxycarbonyl-5, 6-O-cyclohexylidene-3',4'-dideoxyneamine

[Chemical formula 63]

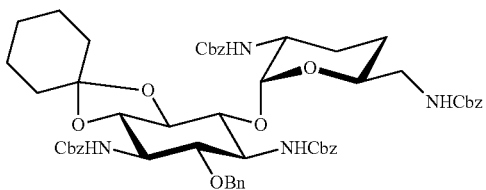

Process A: Tetrahydrofuran (99 mL) was added to the compound (4.970 g, 5.38 mmol) produced in production step 3-2. A 60% sodium hydride (0.26 g, 6.50 mmol) dispersion in paraffin liquid and benzyl bromide (1.15 mL, 9.67 mmol) were added at an internal temperature of 4° C., and the mixture was stirred at an internal temperature of 7 to 8° C. for 21 hr. A saturated aqueous ammonium chloride solution (10 mL) was added thereto at an internal temperature of 4° C., and the mixture was adjusted to pH 7, followed by separation with 100 mL of ethyl acetate and 50 mL of water. The organic layer was dried over magnesium sulfate, and the solvent was removed by distillation under the reduced pressure. The residue was purified by column chromatography on silica gel (toluene:ethyl acetate=3:1) to give the title compound (4.492 g, 4.43 mmol, yield 83%).

Process B: The compound (396 g, 429 mmol) produced in production step 3-2 was dissolved in a mixed solution composed of tetrahydrofuran (8 L) and N,N-dimethylformamide (158 mL), and the solution was cooled to 5° C. Sodium hydride (dispersion in paraffin liquid, 60%; 20.6 g, 515 mmol, 1.2 eq.) and benzyl bromide (91.8 mL, 772 mmol, 1.8 eq.) were added to the solution, and the mixture was stirred at the same temperature for 6 hr. A 10% aqueous ammonium chloride solution (8 L) was added thereto to stop the reaction, and the mixture was extracted with ethyl acetate (8 L). The organic layer was washed once with 20% brine (8 L) and once with a 10% aqueous sodium thiosulfate solution (8 L) and was dried over anhydrous magnesium sulfate. The solvent was then removed by distillation under the reduced pressure. The residue was purified by chromatography on silica gel to give the title compound. Developing solvent=hexane:ethyl acetate=1:1→1:3 (320.24 g, 316 mmol, yield 74%).

APIMS: m/z 1014 [M+H]$^+$ $^1$H-NMR (Pyridine-d5): δ 8.08-8.16 (m, 1H), 7.88-7.96 (m, 1H), 7.10-7.48 (m, 25H), 6.70-6.95 (m, 2H), 5.53 (s, 1H), 5.15-5.46 (m, 8H), 4.91 (AB, 2H, Jgem=11 Hz), 4.40-4.51 (m, 1H), 4.20-4.35 (m, 2H), 3.93-4.16 (m, 4H), 3.72 (t, 1H, J=10, 10 Hz), 3.32-3.50 (m, 2H), 1.77-2.00 (m, 2H), 1.45-1.72 (m, 10H), 1.15-1.35 (m, 2H).

Production Step 3-4

2-Benzyloxy-1,3,2',6'-tetra-N-benzyloxycarbonyl-3', 4'-dideoxyneamine

[Chemical formula 64]

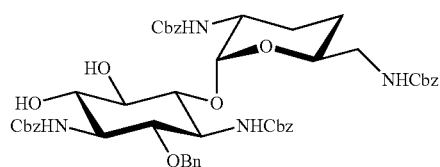

Process A: The compound (22.75 g, 22.5 mmol) produced in production step 3-3 was dissolved in a mixed solution composed of chloroform (460 mL) and methanol (46 mL), and the solution was cooled to 7° C. 90% trifluoroacetic acid (46 mL) was added to the cooled solution, and the mixture was stirred at room temperature for 2 hr. The solvent was removed by distillation under the reduced pressure. Methanol (460 mL) was added to the residue, and the mixture was subjected to slurry washing for 2 hr, followed by filtration to give the title compound (19.47 g, 0.9 mmol, yield 93%).

Process B: The compound (376 g, 371 mmol) produced in production step 3-3 was dissolved in a mixed solution composed of chloroform (7.5 L) and methanol (750 mL), and the mixture was cooled to 10° C. 90% trifluoroacetic acid (750 mL) was added to the cooled solution, and the mixture was stirred at 20° C. for 3 hr 20 min. The solvent was removed by distillation under the reduced pressure. Methanol (7.5 L) was added to the residue, and the slurry was stirred overnight and was filtered to give the title compound (313 g, 335 mmol, yield 90%).

APIMS: m/z 933 [M+H]$^+$ $^1$H-NMR (Pyridine-d5): δ 7.86 (d, 1H, J=6.6 Hz), 7.62-7.70 (m, 1H), 7.10-7.55 (m, 26H), 6.80-6.95 (m, 1H), 5.64 (d, 1H, J=2.9 Hz), 5.13-5.37 (m, 8H), 4.91 (ABq, 2H, Jgem=12 Hz); 4.29-4.37 (m, 3H), 3.90-4.17 (m, 3H), 4.02 (dd, 1H, J=9.1, 10 Hz), 3.94 (dd, 1H, J=8.8, 9.0 Hz), 3.92-3.52 (m, 2H), 1.86-2.04 (m, 2H), 1.47-1.66 (m, 2H).

Production Step 3-5

2-Benzyloxy-3,2',6'-tri-N-benzyloxycarbonyl-1,6-N,O-carbonyl-3',4'-dideoxyneamine

[Chemical formula 65]

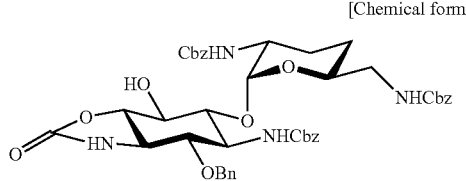

Process A: The compound (19.291 g, 20.7 mmol) produced in production step 3-4 was dissolved in N,N-dimethylformamide (390 mL), and the solution was cooled to 3° C. Sodium hydride (60%, in oil; 4.968 g, 0.124 mol) was added to the cooled solution, and the mixture was stirred at the same temperature for 1.5 hr. The reaction mixture was adjusted to pH about 7 under ice cooling by the addition of a saturated aqueous ammonium chloride solution (400 mL). Ethyl acetate (800 mL) and a saturated aqueous ammonium chloride solution (400 mL) were added thereto, and the mixture was stirred, followed by separation. The organic layer was washed twice with a 5% aqueous ammonium chloride solution (800 mL) and was then dried over magnesium sulfate. The solvent was removed by distillation under the reduced pressure. Methanol (400 mL) was added to the residue. A seed crystal was added thereto, and a contemplated product was crystallized with gentle stirring. The crystals were collected by filtration to give the title compound. The mother liquor was concentrated under the reduced pressure, and the residue was subjected to slurry washing with methanol/diisopropyl ether (1/1; 100 mL) to further give the title compound (15.70 g, 19.0 mmol, yield 92%).

Process B: The compound (293 g, 314 mmol) produced in production step 3-4 was cooled in N,N-dimethylformamide (5.9 L), and the solution was cooled to 3° C. Sodium hydride (dispersion in paraffin liquid, 60%; 75.4 g, 1.88 mol, 6.0 eq.) was added to the cooled solution, and the mixture was stirred at the same temperature for one hr. The reaction mixture was poured into a two-layer solution of a 20% aqueous ammonium chloride solution (12 L) and ethyl acetate (5 L) with vigorous stirring under ice cooling. Further, ethyl acetate (7 L) was added thereto, and the mixture was stirred, followed by separation. The organic layer was washed twice with a 5% aqueous ammonium chloride solution (12 L) and was dried over anhydrous magnesium sulfate. The solvent was removed by distillation under the reduced pressure. Methanol (5.9 L) was added to the residue, and the mixture slurry was stirred overnight and was then filtered to give the title compound (248 g, 301 mmol, yield 95%).

APIMS: m/z 825 [M+H]$^+$ $^1$H-NMR (Pyridine-d5): δ 8.80 (s, 1H), 8.67 (s, 1H), 8.17-8.24 (m, 1H), 7.75-7.53 (m, 1H), 7.12-7.53 (m, 20H), 6.93-7.10 (m, 1H), 5.22 (d, 1H, J=3.1 Hz), 5.11-5.39 (m, 6H), 4.88 (ABq, 2H, Jgem=12 Hz), 3.95-4.38 (m, 7H), 3.73 (t, 1H, J=10, 10 Hz), 3.38-3.53 (m, 2H), 1.77-1.95 (m, 2H), 1.45-1.72 (m, 2H).

Production Step 3-6

2-Benzyloxy-3,2',6'-tri-N-benzyloxycarbonyl-3',4'-dideoxyneamine

[Chemical formula 66]

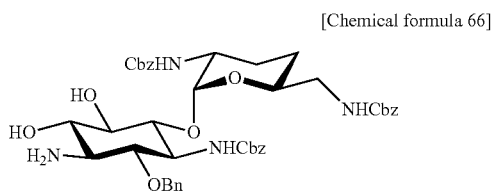

Process A: The compound (822 mg, 0.997 mmol) produced in production step 3-5 was dissolved in a mixed liquid composed of 1,4-dioxane (25 mL) and water (25 mL). Sodium carbonate (127 mg, 1.20 mmol) was added to the solution, and the mixture was stirred at 80° C. for 5 hr. The reaction mixture was cooled and was extracted once with chloroform (50 mL) and once with a mixed liquid composed of chloroform (25 mL) and methanol (25 mL). The extract was dried over magnesium sulfate. The solvent was removed by distillation under the reduced pressure. The residue was dissolved in ethyl acetate (16 mL). A seed crystal was added to the solution, and a contemplated product was crystallized with gentle stirring, followed by filtration to give compound 7. The mother liquor was concentrated under the reduced pressure, and the residue was subjected to slurry washing with ethyl acetate/diisopropyl ether (1/1; 4 mL) to further give the title compound (617 mg, 0.772 mmol, yield 77%).

Process B: The compound (228 g, 276 mmol) produced in production step 3-5 was dissolved in a mixed liquid composed of 1,4-dioxane (6.8 L) and water (6.8 L). Sodium carbonate (29.30 g, 276 mmol, 1.0 eq.) was added the solution, and the mixture was stirred at 80° C. for 6 hr. The reaction mixture was cooled, and sodium chloride (1.37 kg) was dissolved therein, and the mixture was extracted with chloroform (13.7 L). The extract was dried over anhydrous magnesium sulfate. The solvent was then removed by distillation under the reduced pressure to give the title compound (157.87 g, 198 mmol, yield 71%).

FABMS: m/z 799 [M+H]$^+$ $^1$H-NMR (Pyridine-d5): δ 7.10-7.60 (m, 22H), 6.65-6.90 (m, 1H), 5.66 (d, 1H, J=2.9 Hz), 5.34 (s, 2H), 5.24 (ABq, 2H, Jgem=13 Hz), 5.21 (ABq, 2H, Jgem=13 Hz), 4.97 (ABq, 2H, Jgem=11 Hz), 3.64-4.36 (m, 5H), 3.89 (t, 1H, J=9.0, 9.0 Hz), 3.54 (t, 1H, J=10, 10 Hz), 3.39-3.50 (m, 2H), 3.07 (t, 1H, J=10, 10 Hz), 1.87-2.02 (m, 2H), 1.45-1.65 (m, 2H).

Production Step 3-7

1-N—[(S)-4-Benzyloxycarbonylamino-2-benzyloxy-butyryl]-2-benzyloxy-3,2',6'-tri-N-benzyloxycarbonyl-3',4'-dideoxyneamine

[Chemical formula 67]

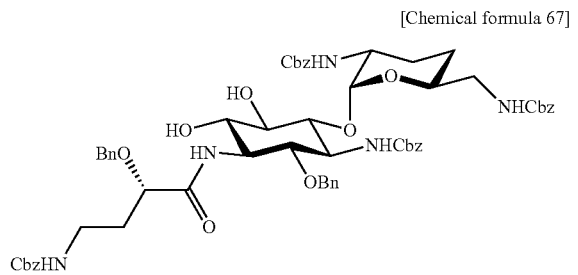

Process A: (S)-2-Benzyloxy-4-benzyloxycarbonylaminobutyric acid (9.065 g, 26.4 mmol) synthesized in Reference Example 1 was dissolved in tetrahydrofuran, and the solution was cooled to 2° C. N-Hydroxysuccinimide (3.038 g, 26.4 mmol) and dicyclohexylcarbodiimide (5.447 g, 26.4 mmol) were added to the solution, and the mixture was stirred at room temperature for 2 hr. The insolubles were filtered to give an active ester solution. The compound (10.552 g, 13.2 mmol) produced in production step 3-6 was dissolved in tetrahydrofuran (210 mL). Triethylamine (3.7 mL, 27 mmol) and the active ester solution were added to the solution, and the mixture was stirred at 50° C. for 3.5 hr. The reaction mixture was diluted with chloroform (800 mL), washed with a saturated sodium hydrogencarbonate solution (800 mL) and was then dried over magnesium sulfate. The solvent was removed by distillation under the reduced pressure. The residue was purified by column chromatography on silica gel (chloroform:ethyl acetate=1:1→chloroform:methanol=30:1→20:1) to give the title compound (11.352 g, 10.1 mmol, yield 76%).

Process B: (S)-2-Benzyloxy-4-benzyloxycarbonylaminobutyric acid (101.78 g, 296 mmol, 1.5 eq.) synthesized in Reference Example 1 was dissolved in tetrahydrofuran (2.04 L), and the solution was cooled to 3.4° C. N-Hydroxysuccinimide (37.53 g, 326 mmol, 1.65 eq.) and dicyclohexylcarbodiimide (67.28 g, 326 mmol, 1.65 eq.) were added to the cooled solution, and the mixture was stirred at 25° C. for 3 hr. The insolubles were filtered to give an active ester solution. The compound (157.87 g, 198 mmol) produced in production step 3-6 was dissolved in tetrahydrofuran (3.16 L). Triethylamine (41.34 mL, 296 mmol, 1.5 eq.) and the active ester solution were added to the solution, and the mixture was stirred at 53° C. for 4.5 hr. The stirred mixture was then diluted with chloroform (12.63 L), and the diluted solution was washed with a 5% aqueous sodium hydrogencarbonate solution (12.63 L) and was then dried over anhydrous magnesium sulfate. The solvent was removed by distillation under the reduced pressure. The residue was purified by column chromatography on silica gel to give the title compound. Developing solvent=chloroform:acetone=3.5:1→3:1→chloroform:methanol=30:1→20:1. (158.45 g, 140 mmol, yield 71%).

LCMS: m/z 1124 [M+H]$^+$ $^1$H-NMR (Pyridine-d5): δ 8.15 (d, 1H, J=8.3 Hz), 7.60-7.72 (m, 1H), 7.10-7.55 (m, 32H), 6.83-7.00 (m, 1H), 5.65 (d, 1H, J=2.9 Hz), 5.12-5.36 (m, 8H), 4.98 (ABq, 2H, Jgem=11, 11 Hz), 4.60 (ABq, 2H, Jgem=12, 12 Hz), 3.90-4.49 (m, 8H), 4.08 (t, 1H, J=9.8, 9.8 Hz), 3.38-3.70 (m, 4H), 2.20-2.36 (m, 2H), 1.85-2.01 (m, 2H), 1.45-1.65 (m, 2H).

Production Step 3-8

4'',6''-Di-O-acetyl-3''-azido-2'',2'-di-O-benzyl-1,3,2',6'-tetra-N-benzyloxycarbonyl-3''-deoxy-2-hydroxy-larbekacin

[Chemical formula 68]

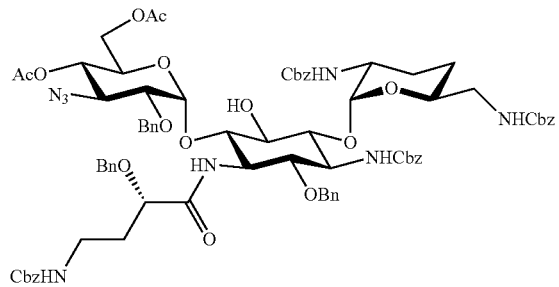

The compound (11.249 g, 10.0 mmol) produced in production step 3-7 and 4,6-di-O-acetyl-3-azido-2-O-benzyl-1,3-dideoxy-1-phenylthio-α-D-glucopyranose (9.440 g, 20.0 mmol), which had been dried under the reduced pressure for 2 hr, were dissolved in methylene chloride (225 mL). Molecular sieves 4 A (powder, 33.7 g), which had been dried under the reduced pressure for 2 hr, was added to the solution, and the mixture was stirred at room temperature under an argon atmosphere for one hr. The reaction vessel was brought to a light shielded state and was cooled to −20° C. N-Iodosuccinimide (10.811 g, 48.1 mmol) and trifluoromethanesulfonic acid (178 mL, 2.01 mmol) were added thereto, and the mixture was stirred at room temperature for 2 hr. N-Iodosuccinimide (5.405 g, 24.0 mmol) and trifluoromethanesulfonic acid (88 mL, 0.99 mmol) were added, and the mixture was stirred at room temperature for additional two hr. Triethylamine (431 mL, 3.09 mmol) was added under ice cooling to stop the reaction. The insolubles were filtered, and the organic layer was washed once with a saturated aqueous sodium hydrogencarbonate solution (500 mL) and twice with a 10% aqueous sodium thiosulfate solution and was dried over magnesium sulfate. The solvent was removed by distillation under the reduced pressure. The residue was purified by column chromatography on silica gel (chloroform:acetone=10:1→:/1→chloroform:methanol=10:1) to give the title compound (9.388 g, 6.32 mmol, yield 63%). The compound (3.16 g, 2.81 mmol) produced in production step 3-7 remaining unreacted was recovered.

LCMS: m/z 1485 [M+H]$^+$ $^1$H-NMR (Pyridine-d5): δ 8.30 (d, 1H, J=8.5 Hz), 7.75-7.83 (m, 1H), 7.20-7.67 (m, 36H), 6.92-7.05 (m, 1H), 6.75-6.90 (m, 1H), 5.92 (d, 1H, J=3.4 Hz), 5.65 (d, 1H, J=2.9 Hz), 4.94-5.35 (m, 12H), 4.62-4.76 (m, 4H), 4.35-4.50 (m, 3H), 3.92-4.35 (m, 9H), 3.71 (dd, 1H, J=3.4, 10 Hz), 3.34-3.62 (m, 4H), 2.18-2.43 (m, 2H), 2.00 (s, 3H), 1.99 (s, 3H), 1.80-1.93 (m, 2H), 1.43-1.65 (m, 2H).

Production Step 3-9

3"-Azido-2",2'"-di-O-benzyl-1,3,2',6'-tetra-N-benzyloxycarbonyl-3"-deoxy-2-hydroxylarbekacin

[Chemical formula 69]

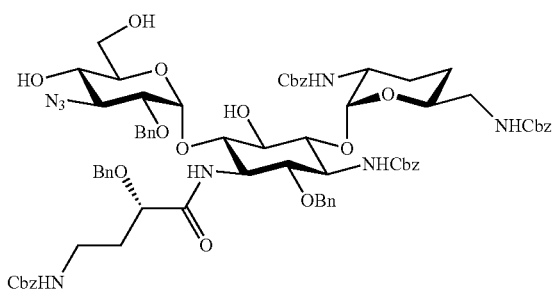

The compound (8.819 g, 5.94 mmol) produced in production step 3-8 was dissolved in a mixed liquid composed of chloroform (180 mL) and methanol (90 mL). 0.5 M sodium methoxide (a methanol solution, 3.6 mL, 1.8 mmol) was added to the solution, and the mixture was stirred at room temperature for 2 hr. Acetic acid (0.14 mL, 2.4 mmol) was added thereto, and the mixture was washed with a saturated aqueous sodium carbonate solution (250 mL). The water layer was again extracted with chloroform (200 mL). The combined organic layers were dried over magnesium sulfate, and the solvent was removed by distillation under the reduced pressure. The residue was purified by column chromatography on silica gel (chloroform:methanol=30:1) to give the title compound (7.263 g, 5.18 mmol, yield 87%).

LCMS: m/z 1401 [M+H]$^+$
$^1$H-NMR (Pyridine-d5): δ 8.11 (d, 1H, J=8.3 Hz), 7.50-7.62 (m, 1H), 7.10-7.58 (m, 35H), 6.96-7.10 (m, 1H), 6.80-6.96 (m, 1H), 6.14-6.23 (m, 1H), 5.50-5.65 (m, 3H), 5.12-5.33 (m, 8H), 4.91 (ABq, 2H, Jgem=11, 11 Hz), 4.83 (ABq, 2H, Jgem=12, 12 Hz), 4.58 (ABq, 2H, Jgem=12, 12 Hz), 3.85-4.51 (m, 14H), 3.37-3.64 (m, 5H), 2.20-2.42 (m, 2H), 1.80-1.95 (m, 2H) 1.45-1.65 (m, 2H).

Production Step 3-10

2-Hydroxyarbekacin

[Chemical formula 70]

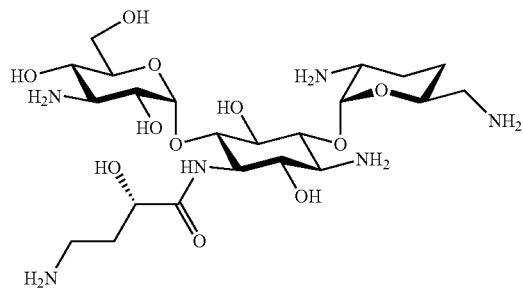

The compound (154 mg, 0.110 mmol) produced in production step 3-9 was dissolved in 3 mL of a solution of 1,4-dioxane:water:1 N hydrochloric acid=40:19:1. The solution was adjusted to pH 1.53, a palladium black powder (154 mg) was added thereto, and the mixture was vigorously stirred under a hydrogen atmosphere. The pH value of the reaction system reached 8.50 three hr after the start of vigorous stirring. The reaction mixture was adjusted to pH 1.68 by the addition of 1 N hydrochloric acid (500 μl) and was vigorously stirred under a H$_2$ atmosphere for 15 hr. The palladium black powder was removed by filtration through a cotton, and the catalyst was washed with water. The filtrate and the wash liquid were combined and were concentrated to dryness. The concentrate was dissolved in water to give a 10-mL solution which was then purified by a Bio Rex 70 column (equilibrated with 0.005 M aqueous ammonia) to give the title compound (51.1 mg, 0.079 mmol, yield 72%).

LCMS: m/z 569 [M+H]$^+$
$^1$H-NMR (26% ND$_3$-D$_2$O): δ5.13 (d, 1H, J=3.5 Hz), 5.03 (d, 1H, J=4 Hz), 4.16 (dd, 1H, J=4, 9.5 Hz), 3.98 (m, 1H), 3.83-3.90 (m, 2H), 3.65-3.77 (m, 4H), 3.37 (t, 1H, J=10, 10 Hz), 3.34 (t, 1H, J=10, 10 Hz), 3.32 (dd, 1H, J=4, 10 Hz), 3.25 (t, 1H, J=10, 10 Hz), 2.97 (t, 1H, J=10, 10 Hz), 2.86 (t, 1H, J=10, 10 Hz), 2.82 (m, 1H), 2.70-2.78 (m, 2H), 2.65 (dd, 1H, J=5, 13 Hz), 2.62 (dd, 1H, J=7, 13 Hz), 1.86-1.96 (m, 1H), 1.69-1.80 (m, 3H), 1.61 (dq, 1H, J=4, 13, 13, 13 Hz), 1.37 (dq, 1H, J=4, 13, 13, 13 Hz).

Example 4

Production of 2-hydroxyarbekacin

[Chemical formula 71]

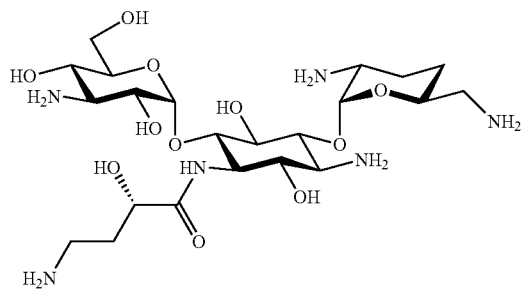

Production Step 4-1

3-Azido-2-O-benzyl-3-deoxy-1-thiophenyl-α-D-glucopyranose

[Chemical formula 72]

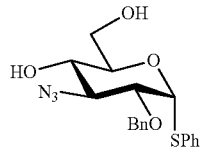

Process A: A 0.13% sodium methoxide/methanol solution (40.5 mL) and 13.5 mL of chloroform were added to the compound (2.67 g) of production step 1-5b, and the mixture was allowed to react at room temperature for 1.5 hr. The reaction mixture was neutralized (pH 6 to 7) by the addition of Dowex 50 W×2 (H$^+$ form, substituted by methanol). The resin was removed by filtration followed by washing with methanol (4 mL×5). The filtrate and the wash liquid were combined and were concentrated to dryness to give a crude product (2.193 g, quantitative).

Process B: The compound (26.0 g) produced in production step 1-5b was suspended in 260 mL of methanol, and 33.3 mL of a 0.5 M sodium methoxide/methanol solution was added. The mixture was allowed to react at room temperature for 30 min, and 1 mL of acetic acid was added dropwise. The reaction solution was concentrated to dryness to give a crude product which as such was used in a next reaction.

ESIMS: m/z 388 [M+H]$^+$ $^1$H-NMR (CDCl$_3$): δ 7.28-7.47 (m, 10H), 5.56 (d, 1H, J=4.6 Hz), 4.68-4.79 (ABq, 2H, Jgem=11.7, 12.3 Hz), 4.21 (dt, 1H, J=3.9, 9.7 Hz), 3.70-3.81 (m, 4H), 3.45 (t, 1H, J=9.3, 9.5 Hz).

Production Step 4-2

2-O-Benzyl-3-benzyloxycarbonylamino-1,3-dideoxy-1-phenylthio-α-D-glucopyranose

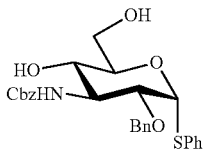

[Chemical formula 73]

Process A: The compound (2.19 g) produced by process A in production step 4-1 was dissolved in 44 mL (20 v/w) of anhydrous tetrahydrofuran. Triphenylphosphine (7.43 g, 5 folds by mol) was added to the solution, and the mixture was allowed to react at room temperature. Water (0.71 mL, 7 folds by mol), N-benzyloxycarbonyloxysuccinimide (1.83 g, 1.3 folds by mol), and triethylamine (2.37 mL, 3 folds by mol) were added thereto 18.5 hr after the start of the reaction, and the mixture was stirred at room temperature. The reaction mixture was concentrated to dryness 2.5 hr after the start of the stirring at room temperature to give 12.6 g of a crude product.

Process B: The compound (about 22.0 g) produced by process B in production step 4-1 was dissolved in a mixed liquid (550 mL, 10 v/mol) of tetrahydrofuran/water (1:1). Triphenylphosphine (36.1 g, 2.5 folds by mol) was added to the solution, and the mixture was allowed to react at room temperature. N-Benzyloxycarbonyloxysuccinimide (17.84 g, 1.3 folds by mol) and 10 mL (1.3 folds by mol) of triethylamine were added thereto 2 hr after the start of the reaction, and the mixture was stirred at room temperature. The reaction mixture was concentrated to dryness 2.5 hr after the start of the stirring and was washed with ethyl acetate/hexane to give 23.7 g of a crude product (yield in three steps 87%).

APIMS: m/z 496 [M+H]$^+$ $^1$H-NMR (DMSO): δ 7.52 (dt, 2H, J=1.5, 7.0 Hz), 7.23-7.36 (m, 13H), 5.78 (d, 1H, J=4.9 Hz), 5.18 (d, 1H, J=6.8 Hz), 4.97-5.12 (ABq, 2H, Jgem=12.7, 12.9 Hz), 4.48-4.71 (ABq, 2H, Jgem=12.2 Hz), 4.55 (t, 1H, J=5.8 Hz), 3.91 (m, 1H), 3.71 (dd, 1H, J=5.1, 10.7 Hz), 3.53 (m, 2H).

Production Step 4-3

4,6-Di-O-acetyl-2-O-benzyl-3-benzyloxycarbonylamino-1,3-dideoxy-1-phenylthio-α-D-glucopyranose

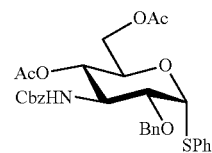

[Chemical formula 74]

Process A: The crude product (12.61 g) produced by process A in production step 4-2 was rendered anhydrous and was dissolved in 56 mL of anhydrous pyridine. Acetic anhydride (5.3 mL, 10 folds by mol) was added to the solution under ice cooling, and the mixture was allowed to react at room temperature for 16 hr. Methanol (4.5 mL) (2 folds by mol as compared with acetic anhydride) was added thereto, and the mixture was allowed to stand at room temperature for 30 min and was concentrated to dryness (azeotropic distillation with toluene: three times). Further, 330 mL of chloroform was added to the residue, and the mixture was washed with a saturated aqueous sodium bicarbonate solution (160 mL×3), a 5% aqueous KHSO$_4$ solution (160 mL×3), and distilled water (160 mL×1) in that order, was dried over a Glauber's salt, and was concentrated to dryness to give 13.3 g of a crude product. The crude product was purified by column chromatography on silica gel and was then crystallized from chloroform/hexane to give 3.19 g of a contemplated product as a crystal (yield 97%).

Process B: A part (4.93 g) of a crude product produced by process B in production step 4-2 was rendered anhydrous and was dissolved in 50 mL (10 v/w) of pyridine. Acetic anhydride (25 mL, 5 v/w) was added to the solution, and the mixture was allowed to react at room temperature for 3 hr. Methanol (25 mL, 5 v/w) was added thereto under ice cooling, and the mixture was allowed to stand at room temperature for 30 min. Next, 150 mL of chloroform was added, and the mixture was washed with water (150 mL×1), 2.5 N hydrochloric acid (150 mL×1), 0.5 N hydrochloric acid (150 mL×1), and a saturated aqueous sodium bicarbonate solution (150 mL×1) in that order, was dried over magnesium sulfate, was concentrated to dryness, and was crystallized from ethyl acetate/hexane to give 5.39 g of a contemplated product (yield 94%).

FABMS: m/z 580 [M+H]$^+$ $^1$H-NMR (CDCl$_3$): δ 7.46-7.49 (m, 2H), 7.26-7.36 (m, 13H), 5.67 (d, 1H, J=5.4 Hz), 5.12 (bs, 2H), 4.89 (t, 1H, J=9.9, 10.3 Hz), 4.74-4.50 (ABq, 2H, Jgem=12.2 Hz), 4.50-4.56 (m, 2H), 4.26 (dd, 1H, J=5.4, 12.2 Hz), 4.07 (dd, 1H, J=9.7, 10.3 Hz), 3.96 (dd, 1H, J=2.2, 12.2 Hz), 3.77 (bs, 1H), 1.98 (s, 3H), 1.94 (s, 3H).

Production Step 4-4

4",6"-Di-O-acetyl-2",2'"-di-O-benzyl-2-hydroxyl-3, 2',6',3"-tetra-N-benzyloxycarbonylarbekacin

[Chemical formula 75]

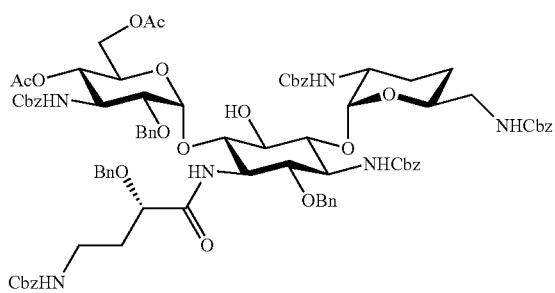

Process A: The compound (2.401 g, 2.14 mmol) produced in production step 3-7 and 4,6-di-O-acetyl-2-O-benzyl-3-benzyloxycarbonylamino-1,3-dideoxy-1-phenylthio-α-D-glucopyranose (1.490 g, 2.57 mmol), which had been dried under the reduced pressure for 2 hr, were dissolved in methylene chloride (48 mL). Molecular sieves 4 A (powder, 7.20 g) dried under the reduced pressure for 2 hr was added to the solution, and the mixture was stirred under an argon atmosphere at room temperature for one hr. The reaction vessel was brought to a light shielded state and was cooled to −20° C. N-Iodosuccinimide (1.390 g, 6.18 mmol) and trifluoromethanesulfonic acid (38 mL, 0.43 mmol) were added thereto, and the mixture was stirred at room temperature for 2 hr. N-Iodosuccinimide (0.700 g, 3.09 mmol) and trifluoromethanesulfonic acid (19 mL, 0.22 mmol) were added to the reaction mixture, and the mixture was stirred at room temperature for additional 2 hr. Triethylamine (90 mL, 0.65 mmol) was added under ice cooling to stop the reaction. The insolubles were filtered, and the organic layer was washed once with a saturated aqueous sodium hydrogencarbonate solution (120 mL) and twice with a 10% aqueous sodium thiosulfate solution, and was dried over magnesium sulfate. The solvent was removed by distillation under the reduced pressure, and the residue was purified by column chromatography on silica gel (chloroform:acetone=10:1→7:1→chloroform:methanol=10:1) to give the title compound (2.350 g, 1.47 mmol, yield 69%).

Process B: Dichloromethane (1.4 L) was added to the compound (70.0 g, 62.3 mmol) produced in production step 3-7 and 4,6-di-O-acetyl-2-O-benzyl-3-benzyloxycarbonylamino-1,3-dideoxy-1-phenylthio-α-D-glucopyranose (43.3 g, 74.7 mmol, 1.2 eq.), which had been dried under the reduced pressure overnight and molecular sieves 4 A (powder, 210 g), which had been dried under the reduced pressure overnight. The mixture was stirred at room temperature under a nitrogen atmosphere for one hr. The reaction mixture was cooled to −15° C. N-Iodosuccinimide (67.2 g, 299 mmol, 4.8 eq.) and trifluoromethanesulfonic acid (1.1 mL, 12.5 mmol, 0.2 eq.) were added thereto, and the mixture was stirred under light shielding at −10° C. for 50 min. N-Iodosuccinimide (33.6 g, 149 mmol, 2.4 eq.) and trifluoromethanesulfonic acid (0.55 mL, 6.23 mmol, 0.1 eq.) were added thereto, and the mixture was stirred at −10° C. for additional 50 min. Triethylamine (3.47 mL, 24.9 mmol, 0.4 eq.) was then added to the reaction mixture to stop the reaction. The insolubles were filtered (washed with 1.4 L of chloroform), and the organic layer was washed once with a 10% aqueous sodium thiosulfate solution (2.8 L) and once with a 5% aqueous sodium hydrogencarbonate solution (2.8 L) and was dried over anhydrous magnesium sulfate. The residue was purified by chromatography on silica gel to give the title compound. Developing solvent=chloroform:acetone=7/1→5/1 (134.11 g, 84.2 mmol, yield 68%).

LCMS: m/z 1593 [M+H]$^+$ $^1$H-NMR (Pyridine-d5): δ 8.22 (d, 1H, J=3.9 Hz), 7.85 (d, 1H, J=7.6 Hz), 7.67-7.77 (m, 1H), 7.13-7.56 (m, 40H), 7.05-7.15 (m, 1H), 6.92-7.03 (m, 2H), 6.23-6.38 (m, 1H), 5.82 (d, 1H, J=3.2 Hz), 5.62 (s, 1H), 5.40 (t, 1H, J=10, 10 Hz), 5.12-5.35 (m, 10H), 4.87 (ABq, 2H, J=12, 12 Hz), 4.95 (ABq, 2H, J=11 Hz), 4.67 (q, 1H, J=10, 10, 10 Hz), 4.60 (ABq, 2H, J=12, 12 Hz), 3.92-4.58 (m, 13H), 3.37-3.61 (m, 4H), 2.18-2.45 (m, 2H), 2.00 (s, 3H), 1.87 (s, 3H), 1.82-1.96 (m, 2H), 1.45-1.68 (m, 2H).

Production Step 4-5

2'",2"-Di-O-benzyl-3"-deoxy-2-hydroxl-3,2',6'3"-tetra-N-benzyloxycarbonylarbekacin

[Chemical formula 76]

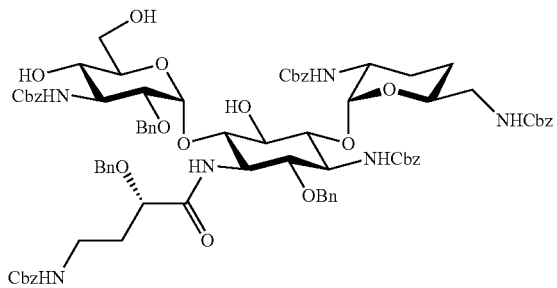

The compound (0.6422 g, 0.40 mmol) produced in production step 4-4 was dissolved in a mixed liquid composed of chloroform (12.8 mL) and methanol (6:4 mL). 0.5 M sodium methoxide (methanol solution, 0.26 mL, 0.13 mmol) was added to the solution, and the mixture was stirred at room temperature for 2 hr. Acetic acid (7.4 μL, 0.13 mmol) was added thereto, and the mixture was washed with a saturated aqueous sodium hydrogencarbonate solution (40 mL). The water layer was again extracted with chloroform (40 mL), and the combined organic layers were dried over magnesium sulfate. The solvent was removed by distillation under the reduced pressure, and the residue was purified by column chromatography on silica gel (chloroform:methanol=30:1) to give the title compound (0.5798 g, 0.38 mmol, yield 95%).

LCMS: m/z 1509 [M+H]$^+$ $^1$H-NMR (Pyridine-d5): δ 8.09 (d, 1H, J=7.8 Hz), 7.60-7.70 (m, 1H), 7.57 (d, 1H, J=8.8 Hz), 7.15-7.55 (m, 40H), 6.70-7.10 (m, 2H), 6.65-6.75 (m, 1H), 6.04 (s, 1H), 5.47-5.58 (m, 3H), 5.15-5.35 (m, 10H), 4.93 (ABq, 2H, Jgem=11, 11 Hz), 4.79 (ABq, 2H, Jgem=12, 12 Hz), 4.61 (ABq, 2H, Jgem=12, 12 Hz), 4.05-4.59 (m, 13H), 3.90-3.98 (m, 2H), 3.38-3.60 (m, 4H), 2.19-2.48 (m, 2H), 1.85-1.95 (m, 2H), 1.43-1.62 (m, 2H).

Production Step 4-6

2-Hydroxyarbekacin

[Chemical formula 77]

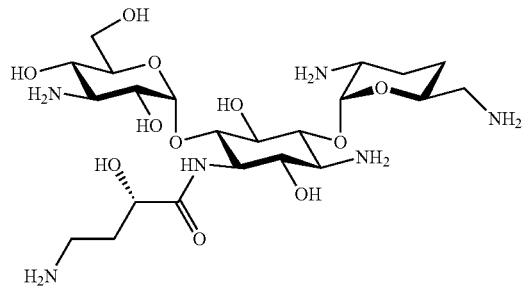

The compound (290.0 mg, 0.192 mmol) produced in production step 4-5 was dissolved in 6 mL of a solution of 1,4-dioxane/water/1 N hydrochloric acid=40/19/1. The solution was adjusted to pH 1.54, a palladium black powder (145 mg) was added thereto, and the mixture was vigorously stirred under a hydrogen atmosphere. The pH value of the reaction system reached 8.50 2 hr after the start of the vigorous stirring. The reaction system was adjusted to pH 1.68 by the addition of 1 N hydrochloric acid (860 μl) and was vigorously stirred under a hydrogen atmosphere for 39 hr. The palladium black powder was removed by filtration through a cotton, and the catalyst was washed with water. The filtrate and the wash liquid were combined and were concentrated to dryness. The residue was dissolved in 10 mL of water, and the solution was purified by an Amberlite CG-50 column (equilibrated with 0.005 M NH$_4$OH) to give the title compound (0.1165 g, yield 72%).

LCMS: m/z 569 [M+H]$^+$ $^1$H-NMR (26% ND$_3$-D$_2$O): δ 5.13 (d, 1H, J=3.5 Hz), 5.03 (d, 1H, J=4 Hz), 4.16 (dd, 1H, J=4, 9.5 Hz), 3.98 (m, 1H), 3.83-3.90 (m, 2H), 3.65-3.77 (m, 4H), 3.37 (t, 1H, J=10, 10 Hz), 3.34 (t, 1H, J=10, 10 Hz), 3.32 (dd, 1H, J=4, 10 Hz), 3.25 (t, 1H, J=10, 10 Hz), 2.97 (t, 1H, J=10, 10 Hz), 2.86 (t, 1H, J=10, 10 Hz), 2.82 (m, 1H), 2.70-2.78 (m, 2H), 2.65 (dd, 1H, J=5, 13 Hz), 2.62 (dd, 1H, J=7, 13 Hz), 1.86-1.96 (m, 1H), 1.69-1.80 (m, 3H), 1.61 (dq, 1H, J=4, 13, 13, 13 Hz), 1.37 (dq, 1H, J=4, 13, 13, 13 Hz).

Example 5

1-N—[(S)-3-Amino-2-hydroxypropionyl]-2-hydroxydibekacin

[Chemical formula 78]

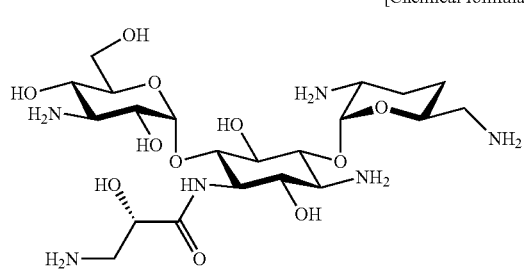

Production Step 5-1

1-N—[(S)-2-Acetoxy-3-amino-N-benzyloxycarbonylpropionyl]-2-benzyloxy-3,2',6'-tri-N-benzyloxycarbonyl-3',4'-dideoxyneamine

[Chemical formula 79]

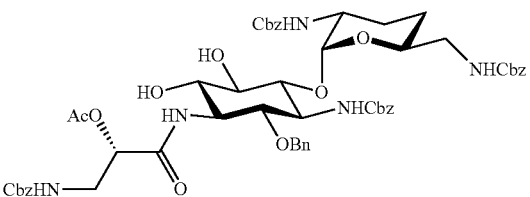

(S)-2-Acetoxy-3-amino-N-benzyloxycarbonylpropanoic acid (21.2 mg) produced in Reference Example 2 and 43.2 mg of 2-benzyloxy-3,2',6'-tri-N-benzyloxycarbonyl-3',4'-dideoxy-2-hydroxyneamine produced in production step 3-6 of Example 3 were dissolved in 0.6 mL of tetrahydrofuran. 2-Propanol (1.3 mL), 0.1 mL of water and 22.4 mg of 4-(4,6-dimethoxy-1,3,5-triazin-2-yl)-4-methylmorpholinium chloride (DMT-MM) were added to the solution, and the mixture was stirred at room temperature for one hr. The reaction solution was concentrated under the reduced pressure, 20 mL of chloroform was added to the residue, and the mixture was washed once with 15 mL of a saturated aqueous sodium bicarbonate solution and three times with 15 mL of water and was dried over a Glauber's salt and was concentrated to dryness. The residue was purified by column chromatography on silica gel (3 g, chloroform→chloroform:methanol=→100:1→100:5→10:1) to give title compound (43.0 mg, yield 75%).

Rf value: 0.57 (chloroform:methanol=10:1)

ESIMS: m/z 1084 [M+Na]$^+$ $^1$H-NMR (pyridine-d5): δ 9.53 (d, 1H, J=6.5 Hz), 8.08 (d, 1H, J=7.5 Hz), 7.68 (d, 1H, J=7.0 Hz), 7.49 (d, 1H, J=7.5 Hz), 7.21-7.45 (m, 26H), 5.72 (d, 1H, J=5.8 Hz), 5.44 (d, 1H, J=12.3 Hz), 5.39 (d, 1H, J=12.1 Hz), 5.22-5.37 (m, 7H), 5.17 (d, 1H, J=12.0 Hz), 5.02 (d, 1H, J=10.5 Hz), 4.59 (br, 1H), 4.43 (dd, 1H, J=8.9, 9.3 Hz), 4.29-4.39 (m, 3H), 4.19-4.22 (m, 2H), 4.08 (dd, 1H, J=7.9, 9.3 Hz), 4.00-4.06 (m, 2H), 3.58-3.62 (m, 1H), 3.50-3.53 (m, 1H), 2.01 (br, 2H), 1.75 (s, 3H), 1.62 (br, 2H).

Production Step 5-2

1-N—[(S)-3-Amino-N-benzyloxycarbonyl-2-hydroxypropionyl]-2,2"-di-O-benzyl-3,2',6',3"-tetra-N-benzyloxycarbonyl-2-hydroxydibekacin

[Chemical formula 80]

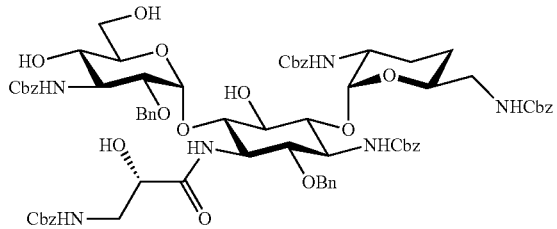

The compound (225 mg) produced in production step 5-1 was dissolved in 7.0 mL of methylene chloride. The compound (246 mg) produced in production step 4-3 of Example 4 and 675 mg of a molecular sieves 4 A powder were added to the solution, and the mixture was stirred at room temperature for one hr. The stirred mixture was cooled to −20° C., 238 mg of N-iodosuccinimide and 5.5 μL of trifluoromethanesulfonic acid were added thereto, and the mixture was stirred under light shielded conditions at room temperature for 3 hr. Triethylamine (55 μL) was added thereto under ice cooling. The reaction solution was filtered through Celite, and the insolubles were washed with 30 mL of chloroform. The solution thus obtained was washed once with 20 mL of a saturated aqueous sodium bicarbonate solution and twice with 15 mL of a 10% aqueous sodium thiosulfate solution, was dried over a Glauber's salt, and was concentrated to dryness. The residue was purified by column chromatography on silica gel (16 g, chloroform:ethyl acetate=30:1→20:1→chloroform:methanol=20:1→10:1) to give 320 mg of a crude product containing 4",6"-di-O-acetyl-1-N—[(S)-2-acetoxy-3-amino-N-benzyloxycarbonylpropionyl]-2,2"-di-O-benzyl-3,2',6',3"-tetra-N-benzyloxycarbonyl-2-hydroxydibekacin as a contemplated product.

Rf value: 0.56 (chloroform:ethyl acetate=2:3): contemplated product

ESIMS: m/z 1553 [M+Na]⁺: contemplated product

The crude product (320 mg) was dissolved in 6.0 mL of methanol. Sodium borohydride (7.1 mg) was added to the solution under ice cooling, and the mixture was stirred at room temperature for 1 hr. Acetone (0.5 mL) was added thereto under ice cooling, and the mixture was stirred at room temperature for 15 min. The mixture was then diluted with 30 mL of chloroform, 20 mL of water was added to the diluted solution, followed by separation. The organic layer was dried over a Glauber's salt and was concentrated to dryness to give 272 mg of a crude product (4",6"-di-O-acetyl-1-N—[(S)-2-acetoxy-3-amino-N-benzyloxycarbonylpropionyl]-2,2"-di-O-benzyl-3,2',6',3"-tetra-N-benzyloxycarbonyl-2-hydroxydibekacin).

Rf value: 0.56 (chloroform:ethyl acetate=2:3)

ESIMS: m/z 1553 [M+Na]⁺

The crude product (272 mg) was dissolved in 5.4 mL of chloroform and 2.7 mL of methanol. A 28% solution (9 μL) of sodium methoxide in methanol was added to the solution under ice cooling, and the mixture was stirred at room temperature for 2 hr. Acetic acid (0.1 mL) was added thereto under ice cooling, the mixture was diluted with 20 mL of chloroform, and the dilution solution was washed with 10 mL of a saturated aqueous sodium bicarbonate solution, was dried over Glauber's salt, and was concentrated to dryness. The residue was purified by column chromatography on silica gel (20 g, chloroform→chloroform:methanol=99:1→97:3) to give the title compound (141 mg, yield 47%).

Rf value: 0.18 (chloroform:ethyl acetate=2:3)

¹H-NMR (pyridine-d5): δ 8.81 (d, 1H, J=6.6 Hz), 8.40 (d, 1H, J=7.5 Hz), 8.31 (d, 1H, J=7.4 Hz), 7.91 (br, 1H), 7.65 (d, 1H, J=7.5 Hz), 7.22-7.51 (m, 36H), 5.78 (d, 1H, J=5.8 Hz), 5.73 (d, 1H, J=6.1 Hz), 5.44 (d, 1H, J=12.1 Hz), 5.39 (d, 1H, J=12.1 Hz), 5.18-5.38 (m, 10H), 5.11 (m, 1H), 5.07 (d, 1H, J=10.5 Hz), 5.01 (d, 1H, J=11.8 Hz), 4.94 (d, 1H, J=10.5 Hz), 4.78 (br, 1H), 4.69-4.75 (m, 4H), 4.45 (br, 1H), 4.42 (dd, 1H, J=8.5, 9.2 Hz), 4.37 (m, 1H), 4.33 (m, 1H), 4.29 (dd, 1H, J=7.7, 8.9 Hz), 4.26 (dd, 1H, J=7.9, 9.5 Hz), 4.00-4.05 (m, 2H), 3.82-3.89 (m, 2H), 3.58-3.62 (m, 1H), 3.49-3.53 (m, 1H), 1.93-2.00 (m, 2H), 1.58 (br, 2H).

ESIMS: m/z 1427 [M+Na]⁺

Production Step 5-3

1-N—[(S)-3-Amino-2-hydroxypropionyl]-2-hydroxydibekacin

[Chemical formula 81]

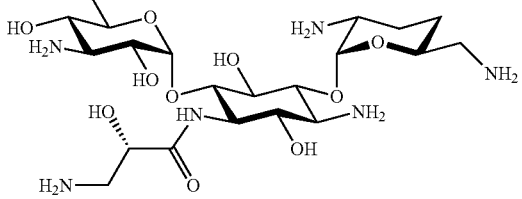

The compound (141 mg) produced in production step 5-2 was dissolved in 7 mL of tetrahydrofuran:water:acetic acid (4:1:1). Thereafter, seven drops of palladium black/water were added as a catalyst, and the mixture was vigorously stirred at room temperature under a hydrogen atmosphere for 13 hr in which the catalyst was replaced once in the 13-hr period. The reaction solution was filtered through a cotton, and the mother liquor was concentrated under the reduced pressure. Water was added to the residue, and the solution was again concentrated to dryness under the reduced pressure. The residue was dissolved in 5 mL of water. The solution was neutralized with 0.1 M aqueous ammonia and was charged into an Amberlite CG-50 column (equilibrated with 0.005 M aqueous ammonia, 5 mL), and the column was washed with 0.005 M aqueous ammonia (5 mL). Elution was carried out with 0.10 M→0.25 M→0.50 M→0.75 M aqueous ammonia (each 10 mL). The corresponding fractions were concentrated to dryness to give the title compound (1.5 carbonate 0.75 hydrate, 47 mg (71%)).

Rf value: 0.18 (chloroform:methanol: 28% aqueous ammonia:ethanol=4:6:7:2)

¹H-NMR (Dcl-D₂O, pD ~3): δ 5.86 (d, 1H, J=3.4 Hz), 5.17 (d, 1H, J=3.8 Hz), 4.56 (dd, 1H, J=4.4, 7.8 Hz), 4.25 (dt, 1H, 4.0, 12.5), 4.16 (t, 1H, J=10.1 Hz), 4.13 (t, 1H, J=10.0 Hz), 4.05 (m, 1H), 3.97 (dd, 1H, J=1.9, 8.9 Hz), 3.94 (dd, 1H, J=1.8, 9.6 Hz), 3.88 (dd, 1H, J=3.1, 8.9 Hz), 3.77-3.84 (m, 3H), 3.72 (t, 1H, J=10.1 Hz), 3.60-3.64 (m, 1H), 3.49 (t, 1H, J=10.5 Hz), 3.37-3.45 (m, 2H), 3.33 (dd, 1H, J=2.1, 8.0 Hz), 3.27 (dd, 1H, J=1.9, 6.5 Hz), 3.16 (dd, 1H, J=6.9, 13.4 Hz), 2.07-2.13 (m, 2H), 1.92-1.98 (m, 1H), 1.60-1.66 (m, 1H).

¹³C-NMR (DCl-D₂O, pD ~3): δ 174.06, 98.72, 95.19, 78.33, 74.95, 74.57, 72.41, 68.23, 68.06, 67.55, 66.38, 65.89, 60.10, 55.83, 55.50, 55.19, 49.07, 42.92, 42.22, 25.65, 20.84

Calcd. for C₂₁H₄₂N₆O₁₁.1.5H₂CO₃.0.75H₂O: C, 40.87; H, 7.09; N, 12.71. Found C, 40.99; H, 7.07; N, 12.65.

Example 6

1-N—[(S)-5-Amino-2-hydroxypentanoyl]-2-hydroxydibekacin

[Chemical formula 82]

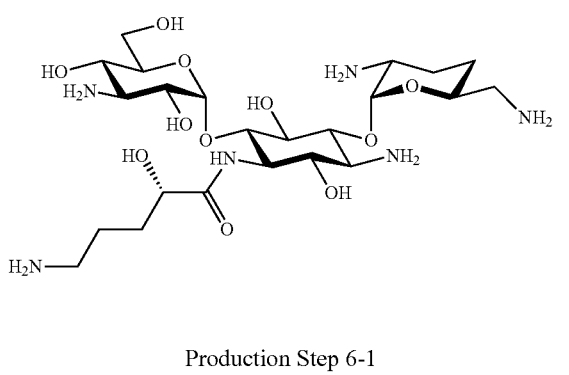

Production Step 6-1

1-N—[(S)-5-Amino-2-benzyloxy-N-benzyloxycarbonylpentanoyl]-2-benzyloxy-3,2',6'-tri-N-benzyloxycarbonyl-3',4'-dideoxyneamine

[Chemical formula 83]

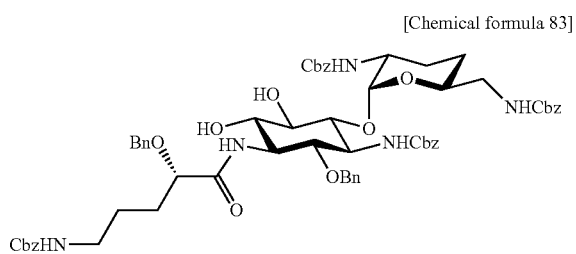

(S)-5-Amino-2-benzyloxy-N-benzyloxycarbonylpentanoic acid (10 mg) produced in Reference Example 3 and 22 mg of 2-benzyloxy-3,2',6'-tri-N-benzyloxycarbonyl-3',4'-dideoxy-2-hydroxyneamine produced in production step 3-6 of Example 3 were dissolved in 0.33 mL of tetrahydrofuran. 2-Propanol (0.70 mL, water 40 μL) and 9 mg of 4-(4,6-dimethoxy-1,3,5-triazin-2-yl)-4-methylmorpholinium chloride (DMT-MM) were added to the solution, and the mixture was stirred at room temperature for 2 hr. The reaction solution was concentrated under the reduced pressure. Chloroform (20 mL) was added to the residue, and the solution was washed once with 10 mL of a saturated aqueous sodium bicarbonate solution and three times with 10 mL of water, was dried over a Glauber's salt and was concentrated to dryness. The residue was purified by column chromatography on silica gel (5 g, chloroform→chloroform:methanol=99:1→97:3→10:1) to give the title compound (22 mg, yield 72%).

Rf value: 0.60 (chloroform:methanol=10:1)

ESIMS: m/z 1160 [M+Na]$^+$ $^1$H-NMR (pyridine-d5): δ 8.66 (d, 1H, J=8.0 Hz), 8.43 (d, 1H, J=7.2 Hz), 8.11 (d, 1H, J=7.8 Hz), 7.87 (br, 1H), 7.70 (br, 1H), 7.60 (d, 2H, J=7.4 Hz), 7.39-7.51 (m, 8H), 7.21-7.31 (m, 20H), 5.79 (d, 1H, J=5.8 Hz), 5.41 (d, 1H, J=12.5 Hz), 5.38 (d, 1H, J=9.9 Hz), 5.31-5.35 (m, 2H), 5.28 (br, 2H), 5.21 (d, 1H, J=12.5 Hz), 5.03-5.19 (m, 4H), 4.78 (d, 1H, J=11.8 Hz), 4.65 (q, 1H, J=9.4 Hz), 4.52 (t, 1H, J=9.5 Hz), 4.49 (d, 1H, J=11.8 Hz), 4.37 (br, 2H), 4.19-4.22 (m, 1H), 4.17 (t, 1H, J=7.3 Hz), 4.10 (t, 1H, J=7.7 Hz), 4.06 (dd, 1H, J=7.7, 9.6 Hz), 3.60-3.67 (m, 1H), 3.52-3.55 (m, 1H), 3.34 (m, 2H), 2.13 (br, 2H), 1.99-2.09 (m, 3H), 1.90 (dt, 1H, J=5.9, 8.0 Hz), 1.62 (br, 2H).

Production Step 6-2

1-N—[(S)-5-Amino-2-benzyloxy-N-benzyloxycarbonylpentanoyl]-2,2"-di-O-benzyl-3,2',6',3"-tetra-N-benzyloxycarbonyl-2-hydroxydibekacin

[Chemical formula 84]

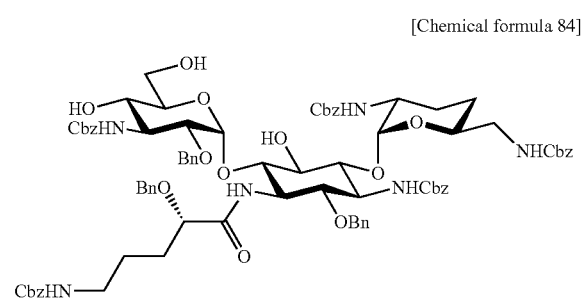

The compound (350 mg) produced in production step 6-1 was dissolved in 8.8 mL of methylene chloride. The compound (364 mg) produced in production step 4-3 of Example 4 and 1000 mg of a molecular sieves 4 A powder were added to the solution, and the mixture was stirred at room temperature for one hr. The reaction solution was cooled to −20° C., 350 mg of N-iodosuccinimide and 8.1 μL of trifluoromethanesulfonic acid were added to the cooled solution, and the mixture was stirred under light shielded conditions at room temperature for 5 hr. Triethylamine (81 μL) was added thereto under ice cooling, and the reaction mixture was filtered through Celite. The insolubles were washed with 20 mL of chloroform. The solution thus obtained was washed once with 15 mL of a saturated aqueous sodium bicarbonate solution and twice with 15 mL of a 10% aqueous sodium thiosulfate solution, was dried over a Glauber's salt and was concentrated to dryness. The residue was purified by column chromatography on silica gel (25 g, chloroform:ethyl acetate=4:1→chloroform:methanol=20:1→10:1) to give a 467 mg of a crude product containing 4",6"-di-O-acetyl-1-N—[(S)-5-amino-2-benzyloxy-N-benzyloxycarbonylpentanoyl]-2,2"-di-O-benzyl-3,2',6',3"-tetra-N-benzyloxycarbonyl-2-hydroxydibekacin as a contemplated product.

Rf value: 0.51 (chloroform:ethyl acetate=2:3): contemplated product

ESIMS: m/z 1630 [M+Na]$^+$ contemplated product

The crude product (467 mg) was dissolved in 9.3 mL of methanol, 20 mg of sodium borohydride was added under ice cooling at room temperature for 1.5 hr. Acetone (1.0 mL) was added thereto under ice cooling, the mixture was stirred at room temperature for 15 min, and the mixture was diluted with 50 mL of chloroform. Water (25 mL) was added thereto followed by separation. The organic layer was dried over a Glauber's salt and was then concentrated to dryness to give 381 mg of a crude product (4",6"-di-O-acetyl-1-N—[(S)-5-amino-2-benzyloxy-N-benzyloxycarbonylpentanoyl]-2,2"-di-O-benzyl-3,2',6',3"-tetra-N-benzyloxy carbonyl-2-hydroxydibekacin).

Rf value: 0.51 (chloroform:ethyl acetate=2:3)

ESIMS: m/z 1630 [M+Na]$^+$

The crude product (381 mg) was dissolved in 7.6 mL of chloroform and 3.8 mL of methanol. A 28% solution (13 μL)

of sodium methoxide in methanol was added to the solution under ice cooling, and the reaction was allowed to react at room temperature for 2 hr. Acetic acid (0.1 mL) was added thereto under ice cooling, and the mixture was diluted with 25 mL of chloroform. Thereafter, the diluted solution was washed with 15 mL of a saturated aqueous sodium bicarbonate solution, was dried over a Glauber's salt and was concentrated to dryness. The residue was purified by column chromatography on silica gel (30 g, chloroform chloroform:methanol=99:1→97:3) to give the title compound 229 mg (yield 49%).

Rf value: 0.22 (chloroform:ethyl acetate=2:3)
ESIMS: m/z 1545 [M+Na]$^+$
$^1$H-NMR (pyridine-d5): δ 8.69 (br, 1H), 8.38 (d, 1H, J=7.9 Hz), 7.65-7.72 (m, 2H), 7.60 (br, 4H), 7.20-7.52 (m, 38H), 5.78 (br, 1H), 5.72 (d, 1H, J=6.1 Hz), 5.20-5.39 (m, 13H), 5.09-5.11 (m, 1H), 5.05 (d, 1H, J=9.0 Hz), 5.01 (t, 1H, J=8.0 Hz), 4.89 (d, 1H, J=12.1 Hz), 4.68-4.80 (m, 6H), 4.48 (d, 1H, J=12.1 Hz), 4.15-4.34 (m, 5H), 4.06 (br, 2H), 3.93 (br, 1H), 3.88 (t, 1H, J=8.1 Hz), 3.52-3.59 (m, 1H), 3.31-3.37 (m, 1H), 1.87-2.20 (m, 5H), 1.78 (br, 1H), 1.62 (br, 2H).

Production Step 6-3

1-N—[(S)-5-Amino-2-hydroxypentanoyl]-2-hydroxydibekacin

[Chemical formula 85]

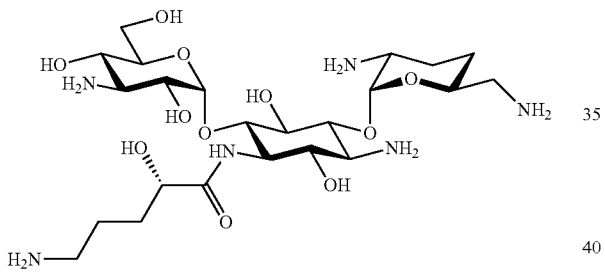

The compound (229 mg) produced in production step 6-2 was dissolved in 9.2 mL of 1,4-dioxane:water:1 N hydrochloric acid (40:19:1), and six drops of palladium black/water were added as a catalyst. The mixture was vigorously stirred at room temperature under a hydrogen gas atmosphere for 14 hr. In this case, the catalyst was replaced once in the 14-hr period. Since the progress of the reaction stopped, the reaction solution was filtered through a cotton, 6 mL of a saturated aqueous sodium bicarbonate solution was added followed by separation with 9 mL of ethyl acetate. The water layer was again extracted with 9 mL of ethyl acetate. The organic layers were combined, were dried over a Glauber's salt and were concentrated to dryness. The residue (161 mg) was dissolved in 8 mL of tetrahydrofuran:water:acetic acid (4:1:1). Palladium black/water (nine drops) was added as a catalyst, and the mixture was vigorously stirred under a hydrogen gas atmosphere at room temperature for 19 hr. In this case, the catalyst was replaced three times in the 19-hr period. The reaction solution was filtered through a cotton, and the mother liquor was concentrated under the reduced pressure. Thereafter, water was again added, and the mixture was again concentrated under the reduced pressure. The residue was dissolved in 5 mL of water. The solution was neutralized with 0.1 M aqueous ammonia and was charged into an Amberlite CG-50 column (equilibrated with 0.005 M aqueous ammonia, 5 mL), and the column was washed with 0.005 M aqueous ammonia (5 mL). Elution was carried out with 0.10 M→0.25 M→0.50 M→0.75 M aqueous ammonia (each 10 mL). The corresponding fractions were concentrated to dryness to give 48 mg (41%) of the title compound (2.25 carbonate 2.75 hydrate).

Rf value: 0.20 (chloroform:methanol: 28% aqueous ammonia:ethanol=4:6:7:2)
$^1$H-NMR (26% ND$_3$-D$_2$O): δ 5.05 (d, 1H, J=3.3 Hz), 4.95 (d, 1H, J=3.7 Hz), 4.02 (dd, 1H, J=3.3, 8.0 Hz), 3.89 (dt, 1H, 2.0, 8.1), 3.81 (t, 1H, J=10.1 Hz), 3.75-3.79 (m, 1H), 3.61-3.70 (m, 4H), 3.29 (t, 1H, J=10.2 Hz), 3.24 (t, 1H, J=10.2 Hz), 3.21 (t, 1H, J=10.4 Hz), 3.17 (t, 1H, J=9.8 Hz), 2.88 (t, 1H, J=10.0 Hz), 2.78 (t, 1H, J=10.0 Hz), 2.75 (dt, 1H, J=1.7, 12.0 Hz), 2.51-2.59 (m, 4H), 1.70-1.79 (m, 1H), 1.59-1.66 (m, 2H), 1.42-1.57 (m, 4H), 1.25-1.32 (m, 1H).
$^{13}$C-NMR (26% ND$_3$-D$_2$O): δ 178.16, 102.70, 99.16, 83.44, 78.36, 75.58, 72.92, 72.59, 72.26, 72.11, 71.48, 70.07, 61.08, 57.19, 56.63, 56.27, 54.97, 50.89, 45.99, 41.06, 32.03, 28.42, 26.94

Calcd. for C$_{23}$H$_{46}$N$_6$O$_{11}$.2.25H$_2$CO$_3$.2.75H$_2$O: C, 39.30; H, 7.31; N, 10.89. Found C, 39.08; H, 7.14; N, 11.05.

Example 7

1-N—[(S)-6-Amino-2-hydroxyhexanoyl]-2-hydroxydibekacin

[Chemical formula 86]

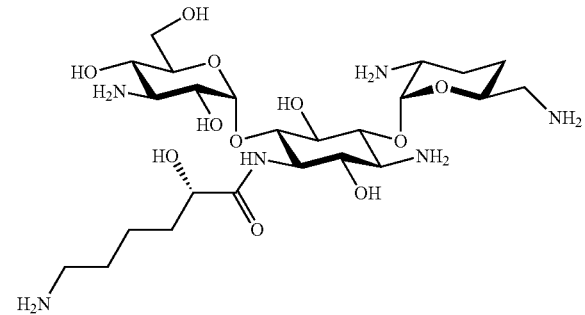

Production Step 7-1

1-N—[(S)-6-Amino-2-benzyloxy-N-benzyloxycarbonylhexanoyl]-2-benzyloxy-3,2',6'-tri-N-benzyloxycarbonyl-3',4'-dideoxyneamine

[Chemical formula 87]

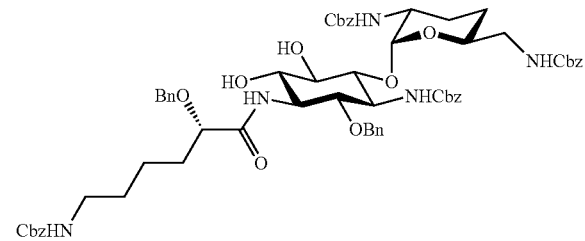

(S)-6-Amino-2-benzyloxy-N-benzyloxycarbonylhexanoic acid (160 mg) produced in Reference Example 4 and 344 mg of 2-benzyloxy-3,2',6'-tri-N-benzyloxycarbonyl-3',4'-dideoxy-2-hydroxyneamine produced in production step 3-6 of Example 3 were dissolved in 5.2 mL of tetrahydrofuran. 2-Propanol (10.3 mL), 0.7 mL of water, and 155 mg of 4-(4,6-dimethoxy-1,3,5-triazin-2-yl)-4-methylmorpholinium chloride (DMT-MM) were added to the solution, and the mixture was stirred at room temperature for 2 hr. The reaction solution was concentrated under the reduced pressure. Chloroform (50 mL) was added to the residue, and the mixture was washed once with 25 mL of a saturated aqueous sodium bicarbonate solution and three times with 20 mL of water, was dried over a Glauber's salt and was concentrated to dryness. The residue was purified by column chromatography on silica gel (25 g, hexane:ethyl acetate=3:1) to give the title compound (355 mg, yield 72%).

Rf value: 0.62 (chloroform:methanol=10:1)

ESIMS: m/z 1174 [M+Na]$^+$

Production Step 7-2

1-N—[(S)-6-Amino-2-benzyloxy-N-benzyloxycarbonylhexanoyl]-2,2"-O-benzyl-3,2',6',3"-tetra-N-benzyloxycarbonyl-2-hydroxydibekacin

[Chemical formula 88]

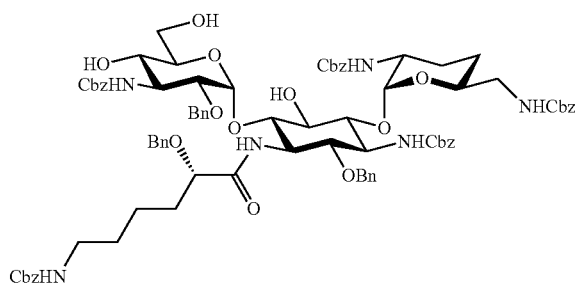

The compound (350 mg) produced in production step 7-1 was dissolved in 8.8 mL of methylene chloride. The compound (352 mg) produced in production step 4-3 of Example 4 and 1000 mg of a molecular sieves 4 A powder were added to the solution, and the mixture was stirred at room temperature for one hr. The reaction solution was cooled to −20° C. N-Iodosuccinimide (341 mg) and 7.9 μL of trifluoromethanesulfonic acid were added to the cooled solution. The mixture was stirred under light shielded conditions at room temperature for 3 hr. Triethylamine (79 μL) was added thereto under ice cooling. The reaction mixture was filtered through Celite, and the insolubles were washed with 20 mL of chloroform. The solution thus obtained was washed once with 15 mL of a saturated aqueous sodium bicarbonate solution and twice with 15 mL of a 10% aqueous sodium thiosulfate solution, was dried over a Glauber's salt and was concentrated to dryness. The residue was purified by column chromatography on silica gel (25 mg, chloroform:ethyl acetate=4:1→chloroform:methanol=20:1→10:1) to give 433 mg of a crude product containing 4",6"-O-acetyl-1-N—[(S)-6-amino-2-benzyloxy-N-benzyloxycarbonylhexanoyl]-2,2"-O-benzyl-3,2',6',3"-tetra-N-benzyloxycarbonyl-2-hydroxydibekacin as a contemplated product.

Rf value: 0.51 (chloroform:ethyl acetate=2:3): contemplated product

ESIMS: m/z 1643 [M+Na]$^+$: contemplated product

The crude product (433 mg) was dissolved in 8.7 mL of methanol. Sodium borohydride (19 mg) was added to the solution under ice cooling, and the mixture was stirred at room temperature for 1.5 hr. Acetone (1.0 mL) was added thereto under ice cooling, and the mixture was stirred at room temperature for 15 min. Thereafter, the reaction mixture was diluted with 50 mL of chloroform. Water (25 mL) was added thereto followed by separation. The organic layer was dried over a Glauber's salt and was then concentrated to dryness to give 357 mg of a crude product (4",6"-O-acetyl-1-N—[(S)-6-amino-2-benzyloxy-N-benzyloxy-carbonylhexanoyl]-2,2"-O-benzyl-3,2',6',3"-tetra-N-benzyloxycarbonyl-2-hydroxydibekacin).

ESIMS: m/z 1643 [M+Na]$^+$

The crude product (357 mg) was dissolved in 7.2 mL of chloroform and 3.6 mL of methanol. A 28% sodium methoxide-methanol solution (13 μL) was added to the solution under ice cooling, and the mixture was stirred at room temperature for 2 hr. Acetic acid (0.5 mL) was added thereto under ice cooling, and the mixture was diluted with 25 mL of chloroform. The diluted solution was washed with 15 mL of a saturated aqueous sodium bicarbonate solution and was dried over a Glauber's salt and was concentrated to dryness. The residue was purified by column chromatography on silica gel (28 g, chloroform→chloroform:methanol=99:1→97:3) to give the title compound (207 mg, yield 44%).

Rf value: 0.22 (chloroform:ethyl acetate=2:3)

ESIMS: m/z 1560 [M+Na]$^+$ $^1$H-NMR (pyridine-d5): δ 8.39 (d, 1H, J=7.9 Hz), 7.76 (d, 1H, J=8.9 Hz), 7.63 (br, 2H), 7.21-7.55 (m, 42H), 5.81 (br, 1H), 5.74 (br, 1H), 5.40 (br, 1H), 5.33-5.38 (m, 3H), 5.36 (t, 1H, J=6.4 Hz), 5.21-5.27 (m, 3H), 5.19 (d, 1H, J=11.9 Hz), 4.79-5.08 (m, 8H), 4.75 (d, 1H, J=11.9 Hz), 4.69 (d, 1H, J=11.9 Hz), 4.22-4.51 (m, 8H), 3.95-4.13 (m, 4H), 3.50-3.61 (m, 2H), 3.27 (br, 2H), 2.02 (br, 2H), 1.94 (br, 2H), 1.42-1.64 (m, 6H).

Production Step 7-3

1-N—[(S)-6-Amino-2-hydroxyhexanoyl]-2-hydroxydibekacin

[Chemical formula 89]

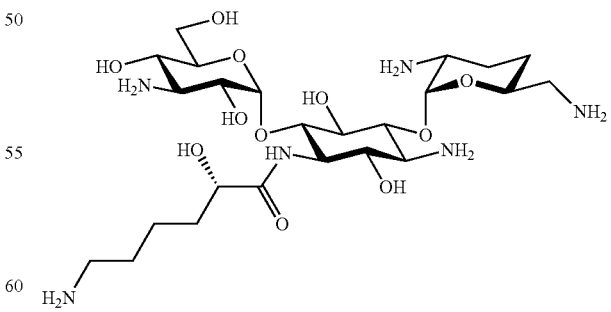

The compound (180 mg) produced in production step 7-2 was dissolved in 9.0 mL of tetrahydrofuran:water:acetic acid (4:1:1). Palladium black/water (nine drops) was added as a catalyst to the solution, and the mixture was vigorously stirred under a hydrogen gas atmosphere at room temperature for 33 hr. In this case, the catalyst was replaced six times in the 33-hr period. The reaction solution was filtered through a cotton, and the mother liquor was concentrated under the reduced pressure. Thereafter, water was again added to the residue, and the solution was again concentrated under the reduced pressure. The residue was dissolved in 5 mL of water. The solution was neutralized with 0.1 M aqueous ammonia and was charged into an Amberlite CG-50 column (equilibrated with 0.005 M aqueous ammonia, 5 mL), and the column was washed with 0.005 M aqueous ammonia (5 mL). Elution was carried out with 0.10 M→0.25 M→0.50 M→0.75 M aqueous ammonia (each 10 mL), and the corresponding fractions were concentrated to dryness to give the title compound (1.5 carbonate trihydrate, 52 mg, yield 60%).

$^1$H-NMR (26% $ND_3$-$D_2O$): δ 5.16 (d, 1H, J=3.2 Hz), 5.05 (d, 1H, J=3.3 Hz), 4.05 (dd, 1H, J=3.5, 8.8 Hz), 4.00 (d, 1H, 9.8), 3.90 (t, 1H, J=9.8 Hz), 3.82-3.87 (m, 1H), 3.69-3.79 (m, 4H), 3.40 (t, 1H, J=9.2 Hz), 3.29-3.37 (m, 2H), 3.27 (t, 1H, J=9.8 Hz), 2.98 (t, 1H, J=10.0 Hz), 2.88 (t, 1H, J=9.8 Hz), 2.85 (dt, 1H, J=4.0, 12.1 Hz), 2.61-2.70 (m, 4H), 1.71-1.83 (m, 3H), 1.59-1.69 (m, 2H), 1.33-1.56 (m, 5H).

$^{13}$C-NMR (26% $ND_3$-$D_2O$): δ 178.24, 102.02, 99.07, 83.37, 78.30, 76.65, 75.43, 73.62, 72.90, 72.39, 72.07, 71.41, 70.04, 61.06, 56.65, 56.16, 54.96, 50.76, 45.95, 41.06, 34.20, 28.40, 26.98, 23.09

Calcd. for $C_{24}H_{48}N_6O_{11}$·1.5$H_2CO_3$·3$H_2O$: C, 41.18; H, 7.72; N, 11.30.

Found C, 41.20; H, 7.73; N, 11.43.

Example 8

1-N—[(R)-4-Amino-2-hydroxybutyryl]-2-hydroxydibekacin

[Chemical formula 90]

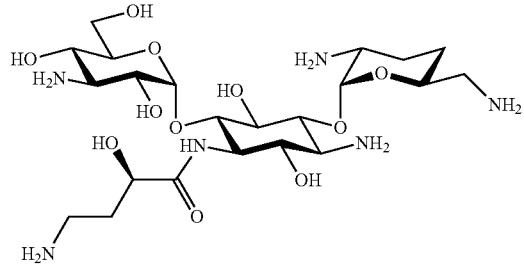

Production Step 8-1

2-O-Benzyl-1-N-[2-(R)—O-benzyl-4-benzyloxycarbonylaminobutyryl]-3,2',6'-tri-N-benzyloxycarbonyl-3',4'-dideoxy-2-hydroxyneamine

[Chemical formula 91]

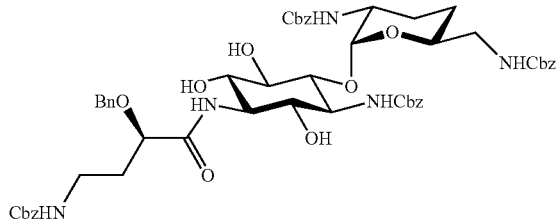

2-Benzyloxy-3,2',6'-tri-N-benzyloxycarbonyl-3',4'-dideoxy-2-hydroxyneamine (420 mg) produced in production step 3-6 of Example 3 and 216 mg of (R)-2-benzyloxy-4-benzyloxycarbonylaminobutyric acid produced in Reference Example 5 were dissolved in 18 mL of a solvent (2-propanol:tetrahydrofuran:water=30:10:3). 4-(4,6-Dimethoxy-1,3,5-triazin-2-yl)-4-methylmorpholinium chloride (hereinafter referred to as "DMT-MM") (218 mg) was added to the solution, and the mixture was stirred at room temperature. DMT-MM (146 mg) was added two hr after the start of stirring, and the mixture was stirred, and, after 3.5 hr, the reaction mixture was concentrated to dryness. Chloroform (50 mL) was added to the residue, and the solution was washed once with 25 mL of a saturated aqueous sodium bicarbonate solution and twice with water. The washed solution was dried over magnesium sulfate and was concentrated to dryness to give 686 mg of a crude product. The crude product was purified by column chromatography on silica gel (50 g, chloroform→chloroform:methanol=99:1→97:3→95:5→10:1) to give the title compound (528 mg, 85%).

Rf value: 0.71 (chloroform:methanol=10:1)

ESIMS: m/z 1146 [M+Na]$^+$ $^1$H-NMR (pyridine-d5 at 80° C.): δ 8.04 (d, 1H, J=7 Hz), 7.55 (br. d, 1H, J=6 Hz), 7.12-7.50 (31H), 7.00 (br. s, 1H), 6.82 (br. s, 1H), 5.64 (d, 1H, J=3 Hz), 5.29 (s, 2H), 5.10-5.27 (4H), 4.95 (s, 2H), 4.50-4.80 (ABq, 2H, Jgem=11.5 Hz), 4.36 (t, 1H, J=8, 8 Hz), 4.28 (m, 1H), 4.20-4.25 (3H), 4.16 (t, 1H, J=9, 9 Hz), 4.08 (t, 1H, J=9, 9 Hz), 3.98 (m, 1H), 3.91 (t, 1H, J=11, 11 Hz), 3.37-3.60 (m, 4H), 2.12-2.30 (m, 2H), 1.85-2.00 (m, 2H), 1.43-1.68 (m, 2H).

Production Step 8-2

2,2''-Di-O-benzyl-1-N-[2-(R)—O-benzyl-4-benzyloxycarbonylaminobutyryl]-3,2',6',3''-tetra-N-benzyloxycarbonyl-2-hydroxydibekacin

[Chemical formula 92]

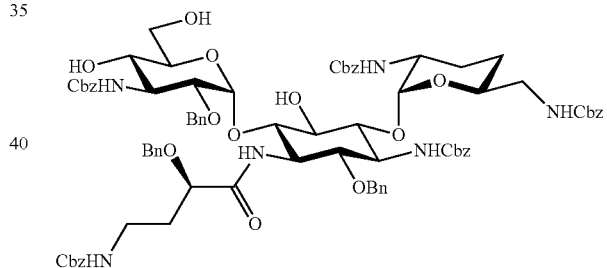

The compound (497 mg) produced in production step 4-3 of Example 4 and 482 mg of the compound produced in production step 8-1 were dissolved in 20 mL of methylene chloride. A molecular sieves 4 A powder (1.445 g) was added to the solution, and the mixture was stirred under an argon atmosphere at room temperature for 2 hr. N-Iodosuccinimide (482 mg) and 7.6 μL of trifluoromethanesulfonic acid were added to the stirred solution at −20° C. with stirring. The reaction mixture was returned to room temperature and was stirred under light shielded conditions for 2 hr. The compound (248 mg) produced in production step 4-3 of Example 4, 241 mg of N-iodosuccinimide, and 3.8 μL of trifluoromethanesulfonic acid were added to the reaction solution three hr after the start of stirring, and, after 4 hr, 27 μL of triethylamine was added thereto under ice cooling. The mixture was filtered through Celite to remove the insolubles. The insolubles were washed with 40 mL of chloroform. The combined organic layers were washed once with 50 mL of a saturated aqueous sodium bicarbonate solution, three times with 50 mL of a 10% aqueous sodium thiosulfate solution and twice with 50 mL of water, was dried over a Glauber's salt and was concentrated to dryness. The residue was purified by column chromatography on silica gel (130 g, chloroform:acetone=10:1→7:1→3:1) to give 530 mg of a crude product containing 4",6"-di-O-acetyl-2,2"-di-O-benzyl-1-N-[2-(R)—O-benzyl-4-benzyloxycarbonylaminobutyryl]-3,2',6',3"-tetra-N-benzyloxycarbonyl-2-hydroxydibekacin as a contemplated product.

Rf value: 0.42 (chloroform:ethyl acetate=2:3): contemplated product

ESIMS: m/z 1615 [M+Na]$^+$: contemplated product

The crude product (527 mg) was dissolved in 10.5 mL of methanol. Sodium borohydride (24.2 mg) was added to the solution with stirring under ice cooling, and the mixture was stirred at room temperature for one hr. Acetone (0.38 mL) was added thereto under ice cooling, and the mixture was stirred at room temperature for 30 min. The reaction mixture was concentrated under the reduced pressure. The residue was dissolved in 50 mL of chloroform, and the solution was washed three times with 25 mL of water, was dried over magnesium sulfate and was concentrated to dryness to give 524 mg of a crude product (4",6"-di-O-acetyl-2,2"-di-O-benzyl-1-N-[2-(R)—O-benzyl-4-benzyloxycarbonylaminobutyryl]-3,2',6',3"-tetra-N-benzyloxycarbonyl-2-hydroxydibekacin).

Rf value: 0.42 (chloroform:ethyl acetate=2:3)

ESIMS: m/z 1615 [M+Na]$^+$

Chloroform (10.5 mL), 5 mL of methanol, and a 28% sodium methoxide-methanol (21.2 mg)/methanol (0.24 mL) solution were added to the crude product, and the mixture was stirred at room temperature. Acetic acid (6.3 μL) was added thereto 2.5 hr after the start of stirring, and the mixture was washed with 30 mL of a saturated aqueous sodium bicarbonate solution. The water layer was again extracted with 30 mL of chloroform. The combined organic layers were dried over magnesium sulfate and was concentrated to dryness. The residue was purified by column chromatography on silica gel (50 g, chloroform:methanol=30:1) to give the title compound (337.5 mg, yield 50%).

Rf value: 0.56 (chloroform:methanol=10:1)

ESIMS: m/z 1531 [M+Na]$^+$ $^1$H-NMR (pyridine-d5 at 80° C.): δ 8.01 (d, 1H, J=8 Hz), 7.57 (br. s, 1H), 7.55 (br. s, 1H), 7.31-7.49 (m, 16H), 7.13-7.31 (m, 24H), 6.98 (br. s, 1H), 6.86 (br. s, 1H), 6.80 (br. s, 1H), 5.68 (d, 1H, J=3 Hz), 5.54 (d, 1H, J=2.5 Hz), 5.12-5.32 (m, 10H), 4.90 (s, 2H), 4.71-4.95 (ABq, 2H, Jgem=12 Hz), 4.57-4.70 (ABq, 2H, Jgem=12 Hz), 4.58 (t, 1H, J=10, 10 Hz), 4.47 (t, 1H, J=9, 9 Hz), 4.43-4.59 (m, 2H), 4.31 (m, 1H), 4.27 (dd, 1H, J=6, 7 Hz), 4.24-4.37 (m, 2H), 3.87-4.14 (m, 6H), 3.54 (m, 2H), 3.40 (m, 2H), 2.30 (m, 1H), 2.24 (m, 1H), 1.84-1.96 (m, 2H), 1.44-1.63 (m, 2H).

Production Step 8-3

1-N—[(R)-4-Amino-2-hydroxybutyryl]-2-hydroxydibekacin

[Chemical formula 93]

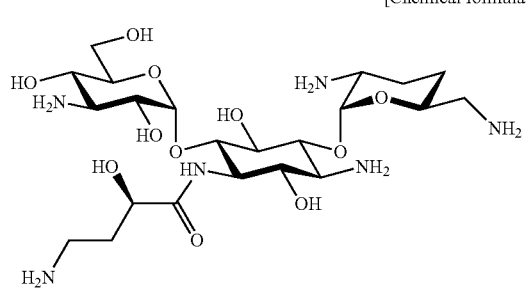

The compound (310 mg) produced in production step 8-2 was dissolved in 21.6 mL of tetrahydrofuran-acetic acid-water (4:1:1). Palladium black (20 drops) suspended in water was added to the solution, and the mixture was stirred at room temperature for 6.5 hr while blowing hydrogen into the system. The catalyst was removed by filtration, palladium black (20 drops) newly suspended in water was added thereto, and the mixture was stirred at room temperature for 12 hr while blowing hydrogen into the system. The catalyst was removed by filtration, palladium black (ten drops) newly suspended in water was added thereto, and the mixture was stirred at room temperature for 14.5 hr while blowing hydrogen into the system. The catalyst was removed by filtration and was washed with water. The filtrate and the wash liquid were combined and were concentrated to dryness. The residue was dissolved in 30 mL of water. The solution was charged into an Amberlite CG-50 column (equilibrated with 0.005 M aqueous ammonia, 15 mL), and the column was washed with 30 mL of 0.005 M aqueous ammonia. Elution was carried out with 0.1 M (30 mL)→0.25 M (30 mL)→0.5 M (30 mL)→0.75 M (30 mL)→1.0 M aqueous ammonia (60 mL), and the corresponding fractions were concentrated to dryness to give the title compound (112 mg, 0.5 carbonate dihydrate, 86%).

Rf value: 0.13 (chloroform:methanol: 15 M aqueous ammonia (concentrated aqueous ammonia): ethanol=4:6:7:2)

$^1$H-NMR (26% ND$_3$-D$_2$O): δ 5.16 (d, 1H, J=3.5 Hz), 5.01 (d, 1H, J=4 Hz), 4.21 (dd, 1H, J=3.5, 9 Hz), 3.98 (m, 1H), 3.93 (t, 1H, J=10.5, 10.5 Hz), 3.87 (m, 1H), 3.75 (t, 1H, J=10, 10 Hz), 3.72-3.80 (m, 2H), 3.69 (t, 1H, J=10, 10 Hz), 3.40 (t, 1H, J=10, 10 Hz), 3.35 (t, 1H, J=10, 10 Hz), 3.32 (dd, 1H, J=4, 10.5 Hz), 3.28 (t, 1H, J=10, 10 Hz), 2.96 (t, 1H, J=10, 10 Hz), 2.88 (t, 1H, J=10, 10 Hz), 2.84 (dt, 1H, J=4, 4, 13 Hz), 2.76 (m, 2H), 2.66 (dd, 1H, J=5, 13.5 Hz), 2.64 (dd, 1H, J=7.5, 13.5 Hz), 1.92 (m, 1H), 1.70-1.84 (m, 3H), 1.64 (dq, 1H, J=3.5, 13, 13, 13 Hz), 1.39 (m, 1H).

$^{13}$C-NMR (26% ND$_3$-D$_2$O): δ 178.39, 102.05, 99.61, 83.52, 79.21, 75.49, 72.90, 72.38, 71.72, 71.47, 70.78, 70.02, 60.97, 56.33, 56.27, 54.97, 50.78, 45.98, 37.96, 37.08, 28.41, 26.94. Calcd. for C$_{22}$H$_{44}$N$_6$O$_{11}$·0.5H$_2$CO$_3$·2H$_2$O. C, 42.51; H, 7.77; N, 13.22. Found, C, 42.51; H, 7.74; N, 13.26.

Example 9

Production of 4"-epi-2-hydroxyarbekacin

[Chemical formula 94]

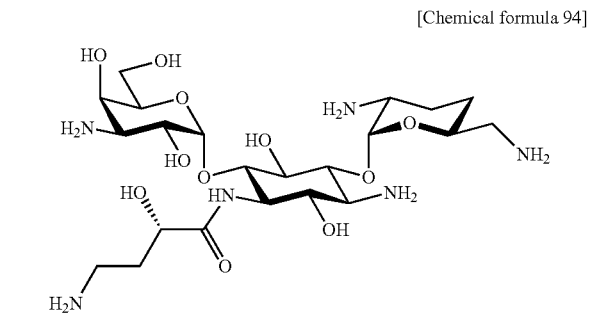

Production Step 9-1

3''-Azido-3,2',6',4'''-tetra-N-benzyloxycarbonyl-2,2'',2'''-tri-O-benzyl-3''-deoxy-4''-epi-2-hydroxyarbekacin

[Chemical formula 95]

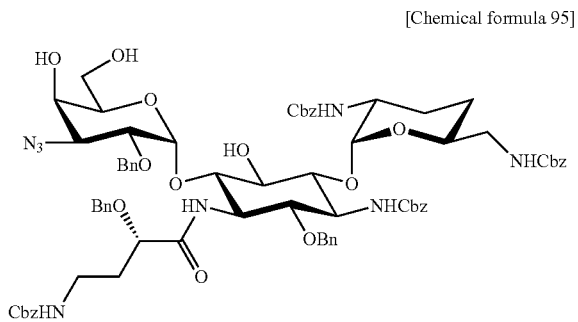

2-O-Benzyl-1-N-[2-(S)—O-benzyl-4-benzyloxycarbonylaminobutyryl]-3,2',6'-tri-N-benzyloxycarbonyl-3',4'-dideoxy-2-hydroxyneamine (39 mg) produced in production step 3-6 of Example 3 was dissolved in 1.2 mL of methylene chloride. The compound (50.3 mg) produced in production step 10-5b of Example 10 and 117 mg of a molecular sieves 4 A powder were added to the solution, and the mixture was stirred at room temperature for 30 min. N-Iodosuccinimide (39 mg) and 0.91 µL of trifluoromethanesulfonic acid were added thereto at −20° C. with stirring, and the mixture was stirred under light shielded conditions at −20° C. for 3 hr. Triethylamine (1.9 µL) was added thereto at −20° C., and the reaction mixture was filtered through Celite. The insolubles were washed with 10 mL of chloroform. The combined organic layers were washed once with 3 mL of a saturated aqueous sodium bicarbonate solution and twice with 3 mL of a 10% aqueous sodium thiosulfate solution, was dried over a Glauber's salt and was concentrated to dryness. The residue was purified by column chromatography on silica gel (4 g, chloroform:ethyl acetate=30:1→20:1, chloroform:methanol=20:1→10:1) to give 41 mg of a crude product.

Rf value: 0.65 (chloroform:ethyl acetate=2:3)

The crude product (41 mg) was dissolved in 1.2 mL of a mixed liquid composed of methylene chloride and a 0.1% solution of sodium methoxide in methanol (methylene chloride:solution=2:1) under ice cooling, and the solution was returned to room temperature, and a reaction was allowed to proceed for 2 hr. A 50% aqueous acetic acid solution (0.8 mL) was added thereto under ice cooling. The mixture was diluted with 10 mL of chloroform, and the diluted solution was washed with 3 mL of a saturated aqueous sodium bicarbonate solution, was dried over a Glauber's salt and was concentrated to dryness. The residue was purified by column chromatography on silica gel (4 g, chloroform→chloroform:methanol=99:1→97:3) to give the title compound (24.1 mg, yield 51%).

Rf value: 0.24 (chloroform:ethyl acetate=2:3)

ESIMS: m/z 1423 [M+Na]+

$^1$H-NMR (pyridine-d5): δ 8.79 (d, 1H, J=7 Hz), 8.43 (d, 1H, J=9 Hz), 7.90 (t, 1H, J=6, 6 Hz), 7.76 (m, 1H), 7.18-7.71 (m, 35H), 7.04 (br. s, 1H), 6.59 (br. s, 1H), 6.07 (d, 1H, J=3.5 Hz), 5.74 (d, 1H, J=3 Hz), 5.06-5.44 (ABq, 2H, Jgem=12 Hz), 5.24-5.41 (m, 4H), 5.04 (br. s, 1H), 4.70-4.80 (m, 3H), 4.57 (dd, 1H, J=4, 10 Hz), 4.36-4.51 (m, 4H), 4.18-4.35 (m, 2H), 4.00-4.15 (m, 2H), 3.68 (m, 1H), 3.60 (m, 2H), 3.51 (m, 1H), 2.48 (m, 1H), 2.34 (m, 1H), 1.95 (m, 2H), 1.61 (m, 2H).

Production Step 9-2

4''-Epi-2-hydroxyarbekacin

[Chemical formula 96]

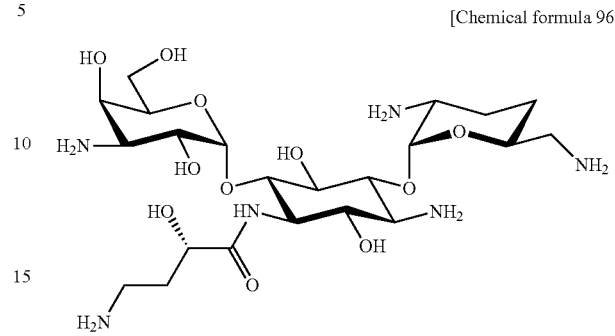

Liquid ammonia (about 5 mL) was reservoired at −50° C. in an egg-plant type flask containing 24 mg of the compound produced in production step 9-1. Metallic sodium (31 mg) was added thereto at −50° C., and the mixture was vigorously stirred with a glass stirrer bar for 2 hr. Solid ammonium chloride was gradually added until the color of radicals disappeared. The system was returned to room temperature to evaporate ammonia. Finally, the contents of the flask were concentrated to dryness by an evaporator. Water (2.4 mL) was added to the residue, and the solution was adjusted to pH 7 by the addition of 1 M aqueous ammonia. The neutralized solution was charged into an Amberlite CG-50 column (equilibrated with 0.005 M aqueous ammonia, 3 mL), and the column was washed with 0.005 M aqueous ammonia (6 mL). Elution was carried out with 0.1 M→0.2 M→0.3 M→0.5 M→0.8 M aqueous ammonia (each 6 mL). The corresponding fractions were concentrated to dryness to give 7.3 mg of the title compound (yield 53%, 2.5 carbonate 4.5 hydrate).

Rf value: 0.16 (chloroform:methanol: 15 M aqueous ammonia (concentrated aqueous ammonia): ethanol=4:6:7:2)

$^1$H-NMR (26% ND$_3$-D$_2$O): δ 5.08 (br. s, 1H), 5.00 (br. s, 1H), 4.13 (m, 2H), 3.75-3.90 (m, 3H), 3.50-3.75 (m, 4H), 3.47 (br. d, 1H, J=10 Hz), 3.20-3.40 (m, 2H), 2.72-2.86 (m, 3H), 2.68 (m, 2H), 2.58 (br. s, 2H), 1.83 (m, 1H), 1.48-1.75 (m, 3H), 1.31 (m, 1H).

Calcd. for $C_{22}H_{44}N_6O_{11} \cdot 2.5H_2CO_3 \cdot 4.5H_2O$. C, 36.57; H, 7.26; N, 10.44. Found, C, 36.65; H, 7.01; N, 10.57.

Example 10

5-Epi-2-hydroxyarbekacin

[Chemical formula 97]

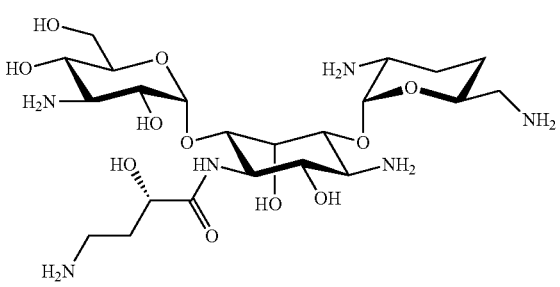

Production Step 10-1

Methyl 3-azido-6-O-benzoyl-2-O-benzyl-3-deoxy-D-glucopyranoside

[Chemical formula 98]

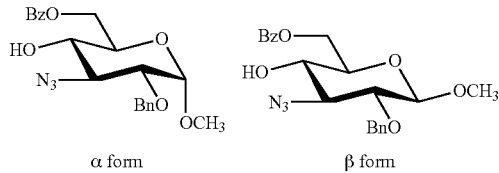

α form    β form

Methyl 3-azido-2-O-benzyl-3-deoxy-D-glucopyranoside (93 mg) was dissolved in 0.84 mL of pyridine. Benzoyl chloride (45 μL) was added to the solution at −20° C. with stirring, and the mixture was stirred at −20° C. for one hr. Water (14 μL) was added thereto, and the mixture was stirred at −20° C. for 30 min. The contents were concentrated to dryness. Chloroform (10 mL) was added thereto, and the mixture was washed three times with 5 mL of a saturated aqueous sodium bicarbonate solution, three times with 5 mL of a 5% aqueous potassium bisulfate solution and three times with 5 mL of water, was dried over a Glauber's salt and was concentrated under the reduced pressure. The residue was purified by column chromatography on silica gel (25 g, hexane:ethyl acetate=3:1) to give the title compound (97 mg, yield 78%).

Rf value: 0.72 (chloroform:methanol=20:1)

α Form $^1$H-NMR (CDCl$_3$): δ 7.30-8.10 (m, 10H), 4.62-4.79 (ABq, 2H, Jgem=12 Hz), 4.73 (dd, 1H, J=4, 12 Hz), 4.60 (d, 1H, J=4 Hz), 4.45 (dd, 1H, J=3, 12 Hz), 3.87 (ddd, 1H, J=3, 4, 10 Hz), 3.85 (t, 1H, J=10, 10 Hz), 3.39 (s, 3H), 3.38 (dd, 1H, J=4, 10 Hz), 3.31 (dt, 1H, J=4, 10 Hz), 2.95 (d, J=4 Hz).

β Form $^1$H-NMR (CDCl$_3$): δ 7.30-8.10 (m, 10H), 4.70-4.91 (ABq, 2H, Jgem=12 Hz), 4.74 (dd, 1H, J=4, 12 Hz), 4.53 (dd, 1H, J=4, 12 Hz), 4.38 (d, 1H, J=8 Hz), 3.59 (s, 3H), 3.57 (dt, 1H, J=4, 4, 12 Hz), 3.50 (t, 1H, J=10, 10 Hz), 3.37 (dt, 1H, J=4, 10 Hz), 3.26 (dd, 1H, J=8, 10 Hz).

Production Step 10-2

Methyl 3-azido-6-O-benzoyl-2-O-benzyl-3-deoxy-4-O-trifluoromethanesulfonyl-D-glucopyranoside

[Chemical formula 099]

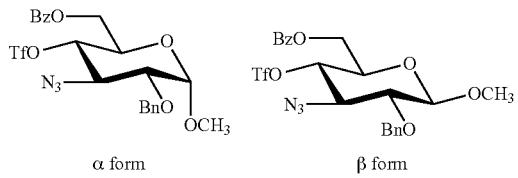

α form    β form

The compound (3.30 g) produced in production step 10-1 was dissolved in 40 mL of methylene chloride. Pyridine (4.8 mL) was added to the solution, 3.4 mL of anhydrous trifluoromethanesulfonic acid was added thereto at −20° C. with stirring, and the mixture was stirred at −20° C. for one hr. Methanol (0.81 mL) was added, and the mixture was stirred at −20° C. for 20 min. Chloroform (300 mL) was added thereto, and the mixture was washed three times with 170 mL of an ice cooled saturated aqueous sodium bicarbonate solution, three times with 170 mL of an ice cooled 5% aqueous potassium bisulfate solution and three times with 170 mL of ice cooled semisaturated brine. The washed solution was dried over a Glauber's salt under ice cooling and was concentrated to dryness under ice cooling to give the title compound (3.60 g, 99%). This compound was unstable and hence was immediately used in the next reaction.

Rf value: 0.45 (hexane:ethyl acetate=3:1)

Production Step 10-3

Methyl 3-azido-4-O-acetyl-6-O-benzoyl-2-O-benzyl-3-deoxy-D-galactopyranoside

[Chemical formula 100]

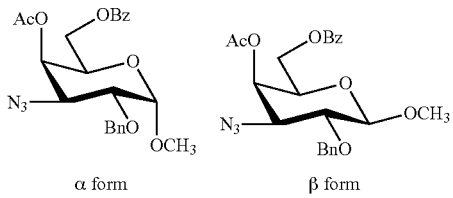

α form    β form

The compound (3.60 g) produced in production step 10-2 was dissolved in 33 mL of N,N-dimethylformamide. Cesium acetate (7.66 g) was added to the solution, and the mixture was allowed to react at room temperature for one hr. Ethyl acetate (330 mL) was added thereto, and the mixture was washed twice with 180 mL of water, twice with 180 mL of a saturated aqueous sodium bicarbonate solution and twice with semisaturated brine, was dried over a Glauber's salt and was concentrated to dryness to give the title compound (3.72 g, yield 99%).

Rf value: 0.40 (hexane:ethyl acetate=3:1)

α Form $^1$H-NMR (CDCl$_3$): δ 7.20-8.10 (m, 10H), 5.47 (d, 1H, J=4 Hz), 4.72-4.95 (ABq, 2H, Jgem=12 Hz), 4.25 (dd, 1H, J=7, 11 Hz), 4.69 (d, 1H, J=4 Hz), 4.38 (ddd, 1H), 4.21 (dd, 1H, J=3, 7 Hz), 3.82 (dd, 1H, J=4, 11 Hz), 4.01 (dd, 1H, J=5, 11 Hz), 3.65 (s, 3H), 2.38 (s, 3H).

β Form $^1$H-NMR (CDCl$_3$): δ 7.20-8.10 (m, 10H), 5.45 (d, 1H, J=4 Hz), 4.62-4.82 (ABq, 2H, Jgem=12 Hz), 4.50 (dd, 1H, J=7, 12 Hz), 4.39 (d, 1H, J=8 Hz), 4.21 (ddd, 1H), 3.94 (t, 1H, J=7, 7 Hz), 3.64 (dd, 1H, J=8, 10 Hz), 3.61 (dd, 1H, J=4, 10 Hz), 3.39 (s, 3H), 2.16 (s, 3H).

Production Step 10-4

3-Azido-1,4-di-O-acetyl-6-O-benzoyl-2-O-benzyl-3-deoxy-D-galactopyranose

[Chemical formula 101]

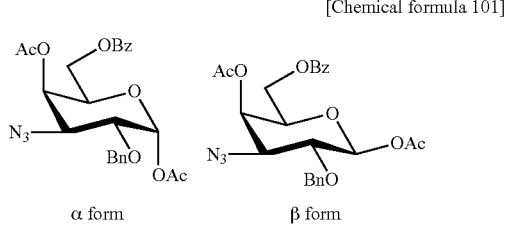

α form      β form

The compound (3.72 g) produced in production step 10-3 was dissolved in 74 mL of acetic acid:acetic anhydride:sulfuric acid (25:25:1), and the solution was stirred at room temperature for 3 hr. Chloroform (740 mL) was added thereto, and the mixture was washed three times with 350 mL of a saturated aqueous sodium bicarbonate solution and three times with 350 mL of water, was dried over a Glauber's salt and was concentrated to dryness to give the title compound (3.66 g, yield 93%).

Rf value: 0.32 (hexane:ethyl acetate=3:1)

α Form $^1$H-NMR (CDCl$_3$): δ 7.30-8.10 (m, 10H), 6.46 (d, 1H, J=4 Hz), 5.55 (dd, 1H), 4.64-4.73 (ABq, 2H, Jgem=12 Hz), 4.40 (dd, 1H, J=7, 11 Hz), 4.35 (m, 1H), 4.19 (dd, 1H, J=6, 11 Hz), 3.96 (m, 2H), 2.16 (s, 3H), 2.14 (s, 3H).

β Form $^1$H-NMR (CDCl$_3$): δ 7.30-8.10 (m, 10H), 5.69 (d, J=8 Hz), 5.51 (dd, 1H), 4.74-4.86 (ABq, 2H, Jgem=12 Hz), 4.42 (m, 1H, J=7, 11 Hz), 4.25 (dd, 1H, J=7, 11 Hz), 4.11 (m, 1H), 3.79 (dd, 1H, J=8, 10 Hz), 3.72 (dd, 1H, J=3, 10 Hz), 2.19 (s, 3H), 2.09 (s, 3H).

Production Step 10-5a

3-Azido-4-O-acetyl-6-O-benzoyl-2-O-benzyl-1-bromo-3-deoxy-α-D-galactopyranose

[Chemical formula 102]

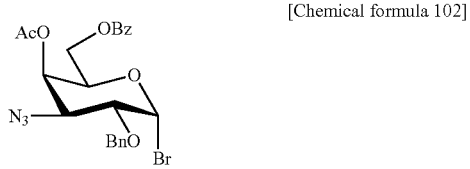

The compound (25 mg) produced in production step 10-4 was dissolved in 0.5 mL of a solvent (methylene chloride:ethyl acetate=9:1). Titanium tetrabromide (29 mg) was added under ice cooling with stirring. The mixture was returned to room temperature and was stirred for one hr. The reaction solution was ice cooled. Ice cooled methylene chloride (2 mL) was added to the cooled solution, and the mixture was washed six times with 2 mL of ice cooled water, was dried over a Glauber's salt and was concentrated to dryness to give the title compound (27 mg, yield 83%). This compound was unstable and, hence, was immediately used in the next reaction.

Rf value: 0.82 (hexane:ethyl acetate=3:2)

$^1$H-NMR (CDCl$_3$): δ 7.15-8.10 (m, 10H), 6.49 (d, 1H, J=4 Hz), 5.54 (dd, 1H, J=2, 4 Hz), 4.45 (dd, 1H, J=7, 11 Hz), 4.39-4.43 (ABq, 2H, Jgem=7 Hz), 4.33 (ddd, 1H), 4.27 (dd, 1H, J=6, 11 Hz), 4.06 (dd, 1H, J=4, 11 Hz), 3.74 (dd, 1H, J=4, 11 Hz), 2.16 (s, 3H).

Production Step 10-5b

3-Azido-4-O-acetyl-6-O-benzoyl-2-O-benzyl-1,3-dideoxy-1-thiophenyl-α-D-galactopyranose

[Chemical formula 103]

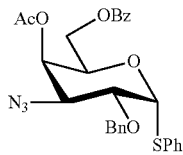

The compound (300 mg) produced in production step 10-4 was dissolved in 5 mL of methylene chloride. Phenylthiotrimethylsilane (353 μL) and 135 μL of trimethylsilyl trifluoromethanesulfonate were added to the solution, and the mixture was refluxed with stirring. The reaction solution was ice cooled six hr after the start of the reflux. Ice cooled methylene chloride (24 mL) was added to the cooled solution, and the mixture was washed twice with 10 mL of an ice cooled 5% aqueous sodium hydroxide solution and twice with 10 mL of ice cooled water, was dried over a Glauber's salt and was concentrated to dryness, followed by recrystallization with ethyl acetate/hexane to give the title compound (204 mg, yield 62%).

Rf value: 0.33 (hexane:ethyl acetate=4:1)

$^1$H-NMR (CDCl$_3$): δ 7.0-8.0 (m, 15H), 5.76 (d, 1H, J=5.5 Hz), 5.52 (d, 1H, J=3 Hz), 4.82 (br. t, 1H, J=6.5, 6.5 Hz), 4.69-4.80 (ABq, 2H, J=11 Hz), 4.36 (dd, 1H, J=7.5, 11.5 Hz), 4.25 (dd, 1H, J=5, 11.5 Hz), 4.17 (dd, 1H, J=5.5, 10.5 Hz), 3.92 (dd, 1H, J=3, 10.5 Hz), 2.16 (s, 3H).

Production Step 10-6

1,3,2',6',3''-Penta-N-tert-butoxycarbonyl-2-hydroxygentamicin C1a

[Chemical formula 104]

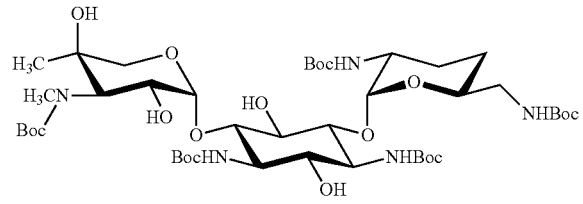

2-Hydroxygentamicin C1a (10.0 g) (2.5 sulfate) was dissolved in 140 mL of water. Triethylamine (30 mL) was added to the solution. A solution (180 mL) of 28.1 g of di-tert-butyl dicarbonate in 1,4-dioxane was added, and the mixture was stirred at 60° C. for 2 hr. Concentrated aqueous ammonia (17 mL) was added thereto, and the mixture was stirred at 60° C. for 30 min. The reaction mixture was returned to room temperature and was concentrated to dryness. Water (1 L) was added to the residue, and the solution was stirred overnight. The resultant precipitate was collected by filtration, was washed with water, and was dried under the reduced pressure to give the title compound (12.4 g, yield 91%).

Rf value: 0.73 (lower layer part of chloroform:methanol:15 M aqueous ammonia (concentrated aqueous ammonia)=1:1:1 was used)

ESIMS: m/z 988 [M+Na]$^+$

Production Step 10-7

2,2''-Di-O-acetyl-1,3,2',6',3''-penta-N-tert-butoxycarbonyl-2-hydroxygentamicin C1a

[Chemical formula 105]

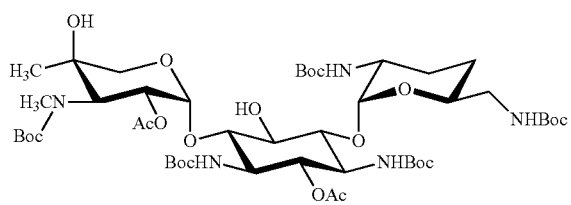

The compound (12.4 g) produced in production step 10-6 was dissolved in 250 mL of pyridine. Acetic anhydride (36.3 mL) was added to the solution under ice cooling, and the mixture was returned to room temperature and was allowed to react. After the elapse of 88 hr from the start of the reaction, 31.3 mL of methanol was added to the reaction mixture under ice cooling, and the mixture was stirred under ice cooling for 30 min. The reaction mixture was concentrated to dryness. Chloroform (1.2 L) was added to the residue, and the solution was washed three times with 600 mL of a saturated aqueous sodium bicarbonate solution, three times with 600 mL of a 5% aqueous potassium bisulfate solution and once with 600 mL of water, was dried over a Glauber's salt and was concentrated under the reduced pressure to give the title compound (13.8 g, quantitative).

Rf value: 0.81 (chloroform:methanol=10:1)
ESIMS: m/z 1072 [M+Na]+

Production Step 10-8

2,2''-Di-O-acetyl-1,3,2',6',3''-penta-N-tert-butoxycarbonyl-4''-eno-5-O-methanesulfonyl-2-hydroxygentamicin C1a

[Chemical formula 106]

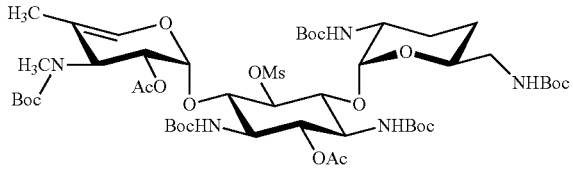

The compound (13.5 g) produced in production step 10-7 was dissolved in 270 mL of methylene chloride. 4-Dimethylaminopyridine (23.6 g) and 10.9 mL of methanesulfonyl chloride were added to the solution under ice cooling, and the mixture was returned to room temperature and was stirred for 45 hr. The reaction mixture was diluted with 1 L of chloroform, and the diluted solution was washed three times with 600 mL of a saturated aqueous sodium bicarbonate solution, three times with 600 mL of a 5% aqueous potassium bisulfate solution and twice with 600 mL of water, was dried over a Glauber's salt and was then concentrated under the reduced pressure to give 19.3 g of a crude product. The crude product was purified by column chromatography on silica gel (200 g, chloroform→chloroform:methanol=50:1) to give the title compound (10.8 g, yield 76%).

Rf value: 0.44 (chloroform:methanol=30:1)
ESIMS: m/z 1132 [M+Na]+

Production Step 10-9

2,5,2''-Tri-O-acetyl-1,3,2',6',3''-penta-N-tert-butoxycarbonyl-4''-eno-5-epi-2-hydroxygentamicin C1a

[Chemical formula 107]

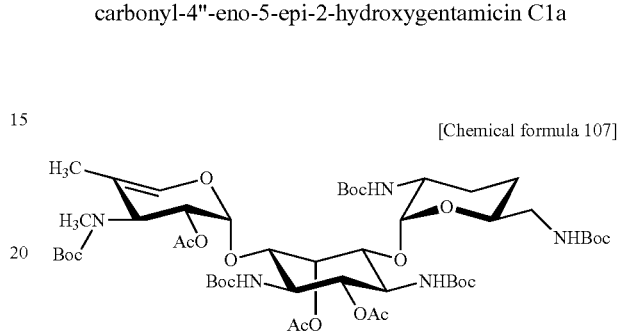

The compound (10.5 g) produced in production step 10-8 was dissolved in 105 mL of N,N-dimethylformamide. Cesium acetate (16.8 g, dried at 120° C. for 6 hr) was added to the solution, and the mixture was stirred at 100° C. for 16 hr. The reaction mixture was diluted with 1.1 L of ethyl acetate, was washed once with 300 mL of water, twice with 300 mL of saturated brine, was dried over a Glauber's salt and was concentrated to dryness to give the title compound (10.1 g, yield 99%).

Rf value: 0.36 (chloroform:methanol=30:1)
ESIMS: m/z 1096 [M+Na]+

Production Step 10-10

1,3,2',6',3''-Penta-N-tert-butoxycarbonyl-4''-eno-5-epi-2-hydroxygentamicin C1a

[Chemical formula 108]

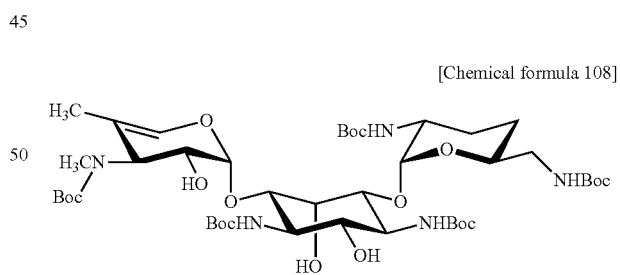

A 1% solution (240 mL) of sodium methoxide in methanol was added to the compound (10.1 g) produced in production step 10-9, and the mixture was allowed to react at room temperature for 41 hr. The reaction mixture was neutralized with Dowex 50 W×2 (H+ form, substituted with methanol). The resin was removed by filtration, and the filtrate was concentrated to dryness to give the title compound (8.2 g, yield 92%).

Rf value: 0.24 (chloroform:methanol=30:1)
ESIMS: m/z 970 [M+Na]+

Production Step 10-11

3',4'-Dideoxy-5-epi-2-hydroxyneamine

[Chemical formula 109]

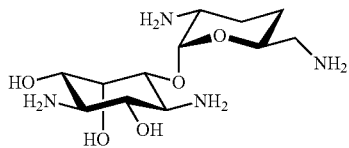

6 M hydrochloric acid-methanol (1:1) (164 mL) was added to the compound (8.2 g) produced in production step 10-10, and the mixture was allowed to react at room temperature for 7 hr. The reaction mixture was further allowed to react at 70° C. for 14 hr. The reaction solution was adjusted to pH 6.6 by the addition of 4 M sodium hydroxide under ice cooling. The solution was then diluted with 1.3 L of water, and the diluted solution was charged into an Amberlite CG-50 (equilibrated with 0.005 M aqueous ammonia) column (900 mL), and elution was successively carried out with 0.005 M→0.1 M→0.2 M→0.3 M→0.4 M→0.5 M aqueous ammonia to give the title compound (1.54 g, 41% as dicarbonate).

Rf value: 0.16 (chloroform:methanol: 15 M aqueous ammonia (concentrated aqueous ammonia): water=1:4:1:1).

$^1$H-NMR (26% $ND_3$-$D_2O$): δ 4.90 (d, 1H, J=3 Hz), 4.16 (s, 1H), 3.76 (m, 1H), 3.43 (d, 1H, J=10 Hz), 3.29 (d, 1H, J=10 Hz), 3.04 (t, 1H, J=10, 10 Hz), 3.00 (t, 1H, J=10, 10 Hz), 2.90 (t, 1H, J=10, 10 Hz), 2.76 (m, 1H), 2.61 (dd, 1H, J=4.5, 13.5 Hz), 2.57 (dd, 1H, J=7, 13.5 Hz), 1.6-1.75 (m, 3H), 1.35 (m, 1H).

$^{13}$C-NMR (26% $ND_3$-$D_2O$): δ 96.51, 75.99, 75.31, 72.47, 71.09, 68.40, 54.32, 53.38, 50.32, 45.84, 28.35, 27.01.

Production Step 10-12

3',4'-Dideoxy-5-epi-1,3,2',6'-tetra-N-tosyl-2-hydroxyneamine

[Chemical formula 110]

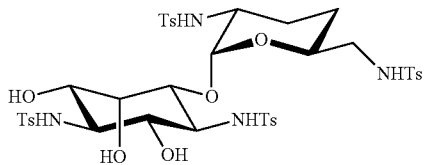

The compound (202 mg, 0.470 mmol, calculated as dicarbonate) produced in production step 10-11 was dissolved in 2.0 mL of water. Sodium carbonate (421 mg) was added to the solution under ice cooling. 1,4-Dioxane (4.0 mL) and 541 mg of tosyl chloride were added thereto, and the mixture was returned to room temperature and was allowed to react. After the elapse of 2 hr from the start of the reaction, 20 mL of water was added to the reaction mixture. The mixture was extracted three times with 10 mL of chloroform, was dried over a Glauber's salt and was concentrated to dryness. The residue was purified by column chromatography on silica gel (10 g, chloroform:methanol=29:1) to give the title compound (383 mg, 88%).

Rf value: 0.43 (chloroform:methanol=10:1)
ESIMS: m/z 945 [M+Na]$^+$ $^1$H-NMR (pyridine-d5): δ 9.41 (d, 1H, J=7 Hz), 8.88 (d, 1H, J=9 Hz), 8.57 (t, 1H, J=6, 6 Hz), 8.31 (br., 1H), 7.89-8.15 (m, 8H), 6.96-7.25 (m, 8H), 5.22 (d, 1H, J=3 Hz), 4.86 (m, 1H), 4.73 (q, 1H, J=10, 10, 10 Hz), 4.60 (br. s, 1H), 4.43 (dt, 1H, J=7, 10, 10 Hz), 4.00 (dd, 1H, J=2, 10.5 Hz), 3.86 (t, 1H, J=10, 10 Hz), 3.77 (dd, 1H, J=2, 10.5 Hz), 3.72 (m, 1H), 3.15-3.32 (m, 2H), 2.26 (m, 1H), 2.09, 2.13, 2.19, 2.21 (each s, each 3H), 1.51-1.69 (m, 3H).

Production Step 10-13

4",6"-Di-O-acetyl-3"-azido-2"-O-benzyl-3"-deoxy-5-epi-1,3,2',6'-tetra-N-tosyl-2-hydroxydibekacin

[Chemical formula 111]

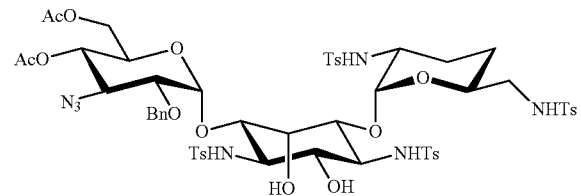

Process A: A solution of the compound (372 mg) produced in production step 1-5a of Example 1 in 21 mL of methylene chloride was added to the compound (711 mg) produced in production step 10-12. Drierite (2.16 g) was added thereto, and the mixture was stirred at room temperature for 3 hr. Mercuric cyanide (795 mg) was added thereto, and the mixture was stirred under light shielded conditions at room temperature for 104 hr. The reaction mixture was filtered through Celite to remove the insolubles. The insolubles were washed with 50 mL of chloroform. The combined organic layers were washed twice with 35 mL of a saturated aqueous sodium bicarbonate solution, twice with 35 mL of a 10% aqueous sodium iodide solution and once with 35 mL of water, were dried over a Glauber's salt and were then concentrated to dryness. The residue was purified by column chromatography on silica gel (10 g, chloroform→chloroform:ethyl acetate=9:1→1:1→2:3) to give the title compound (426 mg, yield 44%). In this case, 385 mg (54%) of the starting compound was recovered.

Process B: The compound (20.5 mg) produced in production step 10-12 and 11.4 mg of the compound produced in production step 1-5b of Example 1 were dissolved in 0.4 mL of methylene chloride. A molecular sieves 4 A powder (63 mg) was added to the solution, and the mixture was stirred at room temperature for one hr. N-Iodosuccinimide (5.9 mg) and a solution of 0.6 μL of trifluoromethanesulfonic acid in 0.1 mL of methylene chloride were added thereto at −20° C. with stirring, followed by stirring at −20° C. under light shielded conditions for 15 hr. The reaction mixture was filtered through Celite to remove the insolubles. The insolubles were washed with 2 mL of chloroform. The combined organic layers were washed twice with 2 mL of a saturated aqueous sodium bicarbonate solution, twice with 2 mL of a 10% aqueous sodium thiosulfate solution and twice with 2 mL of water, were dried over a Glauber's salt and were then concentrated to dryness. The residue was purified by column chromatography on silica gel (10 g, chloroform→chloroform:ethyl acetate=19:1→9:1→1:1→2:3) to give the title compound (7.7 mg, yield 27%). In this case, 7.9 mg (38%) of the starting compound was recovered.

Rf value: 0.19 (chloroform:ethyl acetate=5:2)
ESIMS: m/z 1306 [M+Na]$^+$

¹H-NMR (pyridine-d5): δ8.99 (d, 1H, J=9 Hz), 8.72 (m, 1H), 8.57 (t, 1H, J=6, 6 Hz), 8.53 (m, 1H), 7.05-8.05 (m, 21H), 5.70 (d, 1H, J=3.5 Hz), 5.49 (d, 1H, J=3 Hz), 5.29 (t, 1H, J=10, 10 Hz), 4.84-5.20 (ABq, 2H, Jgem=12 Hz), 5.13 (br. s, 1H), 4.86 (m, 1H), 4.73 (m, 1H), 4.65-4.77 (m, 3H), 4.55 (dd, 1H, J=4, 13.5 Hz), 4.12-4.21 (m, 2H), 4.16 (t, 1H, J=10, 10 Hz), 3.92 (t, 1H, J=10, 10 Hz), 3.79 (dd, 1H, J=3.5, 10 Hz), 3.63 (m, 1H), 3.27 (m, 2H), 2.20 (m, 1H), 2.14, 2.17, 2.21, 2.23 (each s, each 3H), 2.00, 2.05 (each s, each 3H), 1.49-1.57 (m, 3H).

Production Step 10-14

3"-Azido-2"-O-benzyl-3"-deoxy-5-epi-1,3,2',6'-tetra-N-tosyl-2-hydroxydibekacin

[Chemical formula 112]

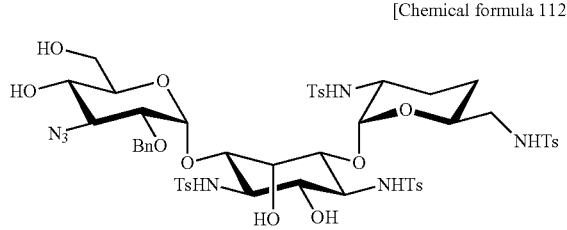

A 0.5% solution (13.4 mL) of sodium methoxide in methanol was added to the compound (673 mg) produced in production step 10-13, and the mixture was allowed to react at room temperature for one hr. The reaction mixture was neutralized with Dowex 50 W×2 (H⁺ form, substituted with methanol). The resin was removed by filtration, and the filtrate was concentrated to dryness to give the title compound (593 mg, 94%).

Rf value: 0.21 (chloroform:ethyl acetate=1:1)
ESIMS: m/z 1222 [M+Na]⁺

Production Step 10-15

5-Epi-hydroxydibekacin

[Chemical formula 113]

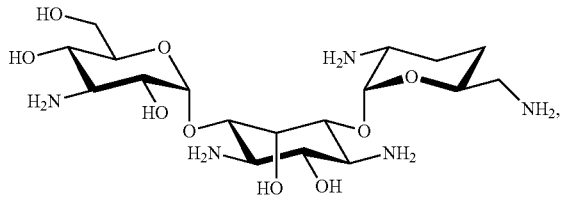

Liquid ammonia (120 mL) was reservoired at −50° C. in an egg-plant type flask containing 593 mg of the compound produced in production step 10-14. Metallic sodium (980 mg) was added at −50° C., and the mixture was vigorously stirred with a glass stirrer bar for 2 hr. Methanol was gradually added until the color of radicals disappeared. The mixture was returned to room temperature to evaporate ammonia and was finally concentrated to dryness by an evaporator. Water (43 mL) was added to the residue, and the solution was adjusted to pH 4 to 5 with Dowex 50 W×2 (H⁺ form). The contents of the flask including the resin as such were added to a column packed with 15 mL of the same resin. The column was washed with 160 mL of water, and elution was carried out with 1 M aqueous ammonia (cut 80 mL). A ninhydrin-positive fraction (Fr 2) was concentrated to dryness to give 299 mg of a crude product. The crude product was brought to an aqueous solution (60 mL). The aqueous solution was charged into a CM-Sephadex C-25 column (equilibrated with 0.005 M aqueous ammonia, 60 mL), and the column was washed with water (120 mL). Elution was carried out with 0.05 M (300 mL) 0.2 M aqueous ammonia (675 mL, cut 12 mL). The corresponding fraction (Fr 38-50) was concentrated to dryness to give the title compound (183 mg, yield 67.5%, as monocarbonate•monohydrate).

Rf value: 0.29 (1-butanol:ethanol:chloroform:17% aqueous ammonia=4:7:2:7)

¹H-NMR (26% ND₃-D₂O): δ 4.99 (d, 1H, J=4 Hz), 4.92 (d, 1H, J=3 Hz), 4.47 (br. s, 1H), 3.84 (br. d, 1H, J=12 Hz), 3.83 (m, 1H), 3.79 (m, 1H), 3.62 (dd, 1H, J=7.5, 12.5 Hz), 3.49 (dd, 1H, J=2, 10 Hz), 3.42 (dd, 1H, J=4, 10.5 Hz), 3.37 (dd, 1H, J=2, 10 Hz), 3.17 (t, 1H, J=10, 10 Hz), 3.15 (t, 1H, J=11, 11 Hz), 3.12 (t, 1H, J=10, 10 Hz), 3.10 (t, 1H, J=10, 10 Hz), 3.06 (t, 1H, J=10, 10 Hz), 2.79 (m, 1H), 2.65 (dd, 1H, J=4.5, 13.5 Hz), 2.60 (dd, 1H, J=7.5, 13.5 Hz), 1.64-1.78 (m, 3H), 1.37 (m, 1H).

¹³C-NMR (26% ND₃-D₂O): δ 102.43, 96.75, 83.11, 76.41, 75.21, 74.00, 72.95, 71.40, 71.06, 68.07, 62.13, 55.39, 54.37, 53.69, 50.84, 46.49, 28.92, 27.62.

Production Step 10-16

2',6'-Di-N-benzyloxycarbonyl-5-epi-2-hydroxy-dibekacin

[Chemical formula 114]

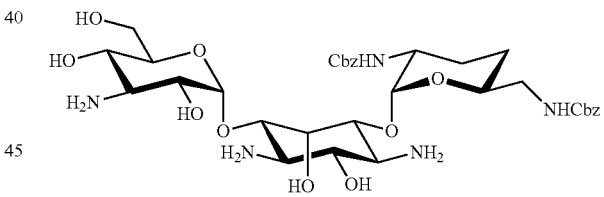

Nickel acetate tetrahydrate (478 mg) was added to 224 mg (calculated as monocarbonate monohydrate) of the compound produced in production step 10-15. Methanol (9.0 mL) was added thereto, and the mixture was brought to a homogeneous solution with an ultrasonic cleaner (2 to 3 min, green color). N-Benzyloxycarbonyloxysuccinimide (263 mg) was added by portions under ice cooling over a period of 2 min. The mixture was stirred under ice cooling for one hr. The mixture was returned to room temperature and was further stirred for 2.5 hr. The reaction mixture was concentrated to dryness. A sodium chloride saturated concentrated aqueous ammonia (15 mL) was added to the residue, and the mixture was extracted five times with 10 mL of 1-butanol. The extracted butanol layer was concentrated to dryness. N,N-Dimethylformamide was added to 1594 mg of the residue, and the mixture was filtered through Celite. The substance on the Celite was washed with N,N-dimethylformamide (4 mL×6). The filtrate and the wash liquid were concentrated to dryness to give 512 mg of a crude product.

Rf value: 0.41 (lower layer part of chloroform:methanol:15 M aqueous ammonia (concentrated aqueous ammonia)=1:1:1 was used)

Production Step 10-17

2',6'-Di-N-benzyloxycarbonyl-5-epi-2-hydroxy-3"-N-trifluoroacetyldibekacin

[Chemical formula 115]

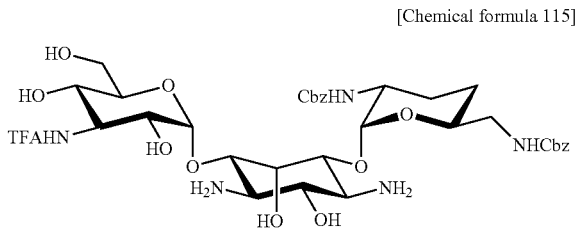

The crude product (512 mg) produced in production step 10-16 was dissolved in 7.1 mL of anhydrous N,N-dimethylformamide. Ethyl trifluoroacetate (74 µL) was added to the solution under ice cooling with stirring. The mixture was returned to room temperature and was stirred for 16.5 hr. The reaction solution was concentrated to dryness to give 609 mg of a product.

Rf value: 0.49 (lower layer part of chloroform:methanol:15 M aqueous ammonia (concentrated aqueous ammonia)=1:1:1 was used)

Production Step 10-18

1-N-(4-Benzyloxycarbonylamino-2-(s)-hydroxybutyryl)-2',6'-di-N-benzyloxycarbonyl-5-epi-2-hydroxy-3"-N-trifluoroacetyldibekacin

[Chemical formula 116]

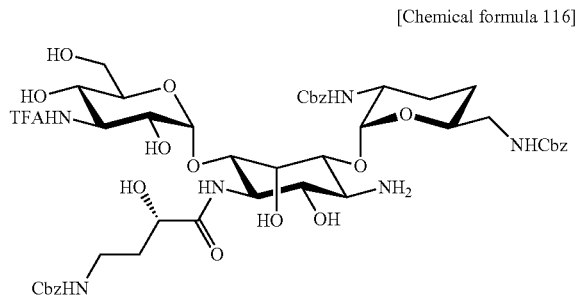

The crude product (609 mg) produced in production step 10-17 was dissolved in 12 mL of anhydrous tetrahydrofuran. Next, a solution (6 mL) of 219 mg of N-benzyloxycarbonyl-4-amino-2-(S)-hydroxybutyric acid succinimide ester in tetrahydrofuran synthesized according to the report of Kawaguchi et al. (Journal of Antibiotics, Vol. 25, pp. 695-708 (1972)) was added dropwise to the solution over a period of 3 min under ice cooling with stirring. The mixture was returned to room temperature and was stirred. After the elapse of 3.5 hr from the start of stirring, a solution (0.92 mL) of 34 mg of N-benzyloxycarbonyl-4-amino-2-(S)-hydroxybutyric acid succinimide ester in tetrahydrofuran was added to the reaction solution under ice cooling with stirring, and the mixture was returned to room temperature and was stirred. After the elapse of 18.5 hr from the start of stirring, the reaction solution was concentrated to dryness. Ethyl acetate (150 mL) was added to the residue, and the mixture was washed twice with 30 mL of a saturated aqueous sodium bicarbonate solution and twice with 30 mL of water and was concentrated to dryness to give 604 mg of the reaction mixture.

Rf value: 0.67 (lower layer part of chloroform:methanol:15 M aqueous ammonia (concentrated aqueous ammonia)=1:1:1 was used).

Production Step 10-19

5-Epi-2-hydroxyarbekacin

[Chemical formula 117]

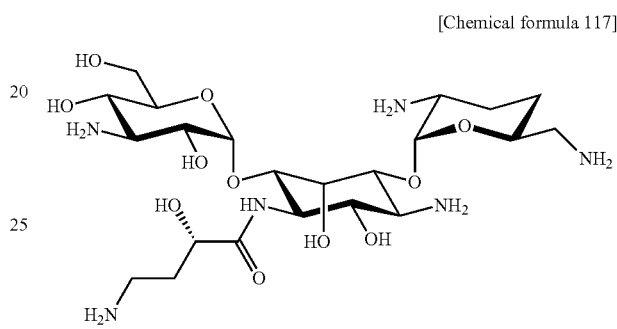

Tetrahydrofuran (20.5 mL) and 15.4 mL of 3.5 M aqueous ammonia were added to the reaction mixture (604 mg) produced in production step 10-18, and the mixture was stirred at room temperature for 44 hr. The reaction solution was concentrated to dryness. Tetrahydrofuran-acetic acid-water (4:1:1) (33 mL) was added to 656 mg of the residue. Further, 10 drops of a suspension of palladium black in water were added thereto, and the mixture was stirred at the atmospheric pressure for 5 hr while blowing hydrogen into the system. Next, palladium black was removed from the reaction solution by filtration. The palladium black was washed with water, and the filtrate and the wash liquid were combined and were concentrated to dryness. 2 M aqueous ammonia was added to the residue, and the mixture was allowed to stand at room temperature overnight. The insolubles were removed by filtration through a cotton stopper and were concentrated to dryness to give 466 mg of a crude product. This crude product was dissolved in 60 mL of water to give an aqueous solution. The aqueous solution was added to a CM-Sephadex C-25 column (equilibrated with 0.005 M aqueous ammonia, 60 mL). The column was washed with 120 mL of 0.005 M aqueous ammonia. Elution was carried out with aqueous ammonia with the concentration being varied from 0.05 M (300 mL) to 0.5 M (600 mL), and 0.75 M (600 mL) aqueous ammonia. The corresponding fractions were concentrated to give the title compound: 5-epi-2-hydroxyarbekacin (65 mg, 2.5 carbonate trihydrate, 20% in four steps).

Rf value: 0.11 (1-butanol:ethanol:chloroform:17% aqueous ammonia=4:7:2:7)

$^{1}$H-NMR (26% $ND_3$-$D_2O$): δ 4.95 (d, 1H, J=4 Hz), 4.92 (d, 1H, J=3 Hz), 4.44 (t, 1H, J=2, 2 Hz), 4.17 (t, 1H, J=10, 10 Hz), 4.16 (dd, 1H, J=4, 10 Hz), 3.85 (dd, 1H, J=2, 12 Hz), 3.79 (dd, 1H, J=2, 10.5 Hz), 3.78 (m, 1H), 3.77 (m, 1H), 3.60 (dd, 1H, J=7, 12 Hz), 3.51 (dd, 1H, J=2, 10.5 Hz), 3.34 (t, 1H, J=10, 10 Hz), 3.12 (dd, 1H, J=4, 10 Hz), 3.21 (t, 1H, J=10, 10 Hz), 3.14 (t, 1H, J=10, 10 Hz), 3.02 (t, 1H, J=10, 10 Hz), 2.80 (m, 1H), 2.70-2.80 (m, 2H), 2.66 (dd, 1H, J=5, 13.5 Hz), 2.61 (dd, 1H, J=7.5, 13.5 Hz), 1.91 (m, 1H), 1.64-1.80 (m, 4H), 1.37 (m, 1H).

$^{13}$C-NMR (26% ND$_3$-D$_2$O): δ 178.69, 101.16, 96.93, 78.02, 76.08, 74.06, 73.28, 72.82, 71.34, 70.92, 68.35, 62.01, 55.40, 54.18, 53.77, 50.69, 46.29, 38.64, 37.58, 28.74, 27.43.

Example 11

5,4"-Diepi-2-hydroxyarbekacin

[Chemical formula 118]

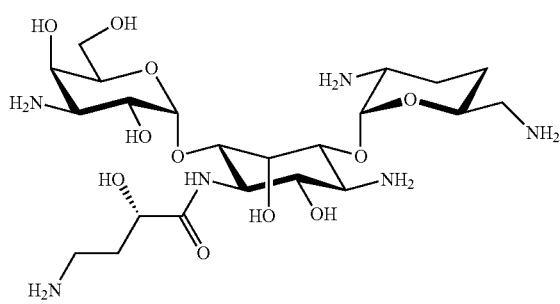

Production Step 11-1

3,2',6',3",4'''-Penta-N-tert-butoxycarbonyl-5-epi-2-hydroxyarbekacin

[Chemical formula 119]

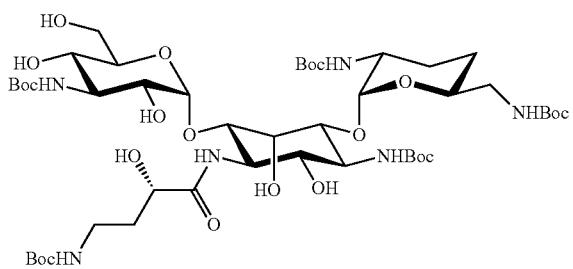

The compound (65 mg) produced in production step 10-19 of Example 10 was dissolved in 0.91 mL of water. Triethylamine (0.16 mL) was added to the solution, a solution of 175 mg of di-tert-butyl dicarbonate in 1,4-dioxane (1.17 mL) was added thereto, and the mixture was stirred at 60° C. for 1.5 hr. Concentrated aqueous ammonia (0.11 mL) was added thereto, and the mixture was stirred at 60° C. for 30 min. The reaction mixture was returned to room temperature and was concentrated to dryness. The residue was subjected to azeotropic distillation twice with methanol to give the title compound (103 mg, quantitative).

Rf value: 0.53 (chloroform:methanol: 15 M aqueous ammonia (concentrated aqueous ammonia)=5:1:0.1)

ESIMS: m/z 1091 [M+Na]$^+$

Production Step 11-2

3,2',6',3",4'''-Penta-N-tert-butoxycarbonyl-4",6"-O-cyclohexylidene-5-epi-2-hydroxyarbekacin

[Chemical formula 120]

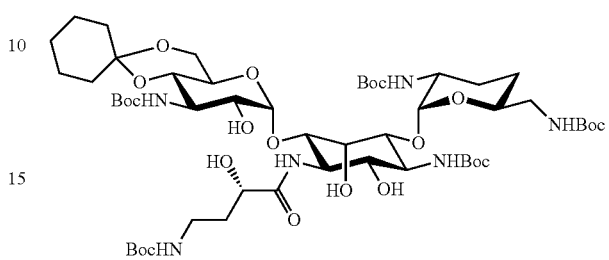

The compound (103 mg) produced in production step 11-1 was dissolved in 2.0 mL of N,N-dimethylformamide. Cyclohexanone di-1-propyl acetal (58 μL) and 12.4 mg of p-toluenesulfonic acid were added to the solution, and the mixture was allowed to react at room temperature for one hr. A saturated aqueous sodium bicarbonate solution (20 mL) was added thereto, and the resultant precipitate was collected by filtration, was washed with water, and was dried under the reduced pressure to give the title compound (103 mg, 88%).

Rf value: 0.53 (chloroform:methanol=10:1)

ESIMS: m/z 1171 [M+Na]$^+$

Production Step 11-3

2,2",2'''-Tri-O-acetyl-3,2',6',3",4'''-penta-N-tert-butoxycarbonyl-4",6"-O-cyclohexylidene-5-epi-2-hydroxyarbekacin

[Chemical formula 121]

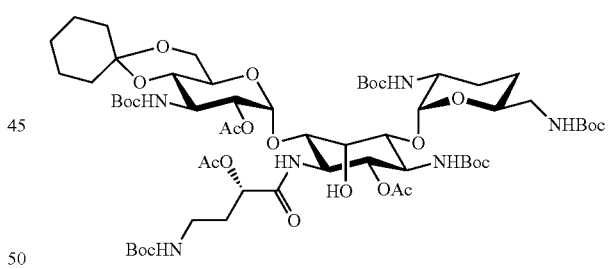

The compound (103 mg) produced in production step 11-2 was dissolved in 2.1 mL of pyridine. Acetic anhydride (0.13 mL) was added to the solution under ice cooling, and the mixture was returned to room temperature and was allowed to react. After the elapse of 18.5 hr from the start of the reaction, 0.11 mL of methanol was added thereto under ice cooling, and the mixture was allowed to stand at room temperature for 30 min and was concentrated to dryness. Chloroform (10 mL) was added to the residue. The solution was washed twice with 3 mL of a saturated aqueous sodium bicarbonate solution, twice with 3 mL of a 5% aqueous potassium bisulfate solution and twice with 3 mL of water and was dried over a Glauber's salt and was concentrated to dryness to give the title compound (117 mg, quantitative).

Rf value: 0.39 (chloroform:methanol=15:1)

ESIMS: m/z 1297 [M+Na]$^+$

Production Step 11-4

2,2'',2'''-Tri-O-acetyl-3,2',6',3'',4'''-penta-N-tert-butoxycarbonyl-5-epi-2-hydroxyarbekacin

[Chemical formula 122]

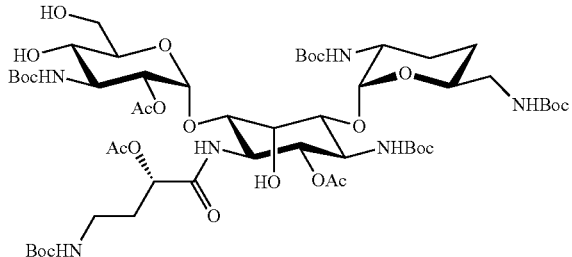

The compound (117 mg) produced in production step 11-3 was dissolved in 5.17 mL of chloroform methanol (10:1). A 90% aqueous trifluoroacetic acid solution (0.47 mL) was added to the solution under ice cooling with stirring, and the mixture was returned to room temperature and was stirred. After the elapse of 30 min from the start of stirring, 5.3 mL of chloroform was added. The mixture was washed once with 3 mL of water, twice with 3 mL of a saturated aqueous sodium bicarbonate solution and twice with 3 mL of semisaturated brine and was dried over a Glauber's salt and was concentrated to dryness to give the title compound (107 mg, quantitative).

Rf value: 0.46 (chloroform:methanol=10:1)
ESIMS: m/z 1217 [M+Na]$^+$

Production Step 11-5

2,2'',2'''-Tri-O-acetyl-3,2',6',3'',4'''-penta-N-tert-butoxycarbonyl-5-epi-2-hydroxy-6''-O-tritylarbekacin

[Chemical formula 123]

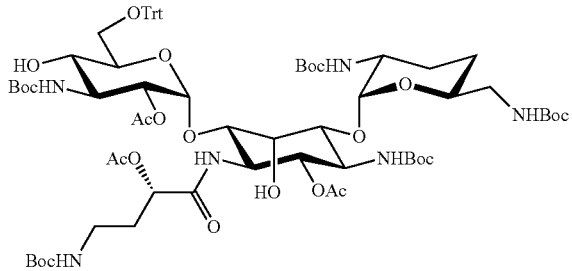

The compound (83 mg) produced in production step 11-4 was dissolved in 1.7 mL of pyridine. 4-Dimethylaminopyridine (25 mg) and 116 mg of trityl chloride were added to the solution, and the mixture was allowed to react at 65° C. After the elapse of 17 hr from the reaction, the mixture was returned to room temperature. Methanol (0.08 mL) was added thereto, and the mixture was allowed to stand for one hr. The mixture was then was concentrated to dryness. Chloroform (8 mL) was added to the residue. The solution was washed twice with 3 mL of a saturated aqueous sodium bicarbonate solution, three times with 3 mL of a 5% aqueous potassium bisulfate solution and three times with 3 mL of water, was dried over a Glauber's salt and was concentrated to dryness. The residue was purified by column chromatography on silica gel (3.4 g, toluene:ethyl acetate:acetone=6:1:1) to give the title compound (65 mg, 65%).

Rf value: 0.57 (chloroform:methanol=10:1)
ESIMS: m/z 1459 [M+Na]$^+$

Production Step 11-6

2,2'',4'',2'''-Tetra-O-acetyl-3,2',6',3'',4'''-penta-N-tert-butoxycarbonyl-5,4''-diepi-2-hydroxy-6''-O-tritylarbekacin

[Chemical formula 124]

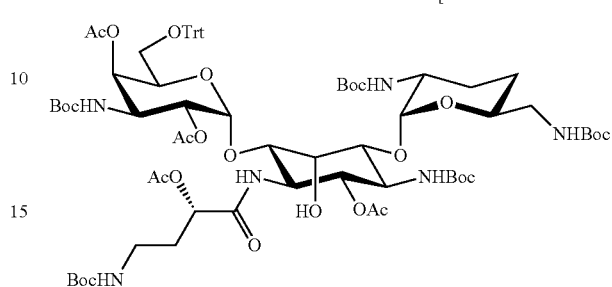

The compound (112 mg) produced in production step 11-5 was dissolved in 2.3 mL of methylene chloride under a nitrogen atmosphere. Pyridine (0.13 mL) was added to the solution. Trifluoromethanesulfonic acid anhydride (66 μL) was added thereto under a nitrogen atmosphere at −78° C. with stirring. The mixture was stirred at −20° C. under a nitrogen atmosphere for one hr. Methanol (79 μL) was added thereto at −20° C., and 14 mL of ice cooled chloroform was immediately added thereto. The mixture was washed twice with 7 mL of an ice cooled 10% aqueous potassium bisulfate solution, twice with 7 mL of an ice cooled saturated aqueous sodium bicarbonate solution and twice with 7 mL of ice cooled water, followed by drying over a Glauber's salt under ice cooling for 10 min. The dried solution was concentrated under the reduced pressure under ice cooling. When the resolution became a syrup, the concentration was stopped.

The resultant syrup was dissolved in 1.1 mL of N,N-dimethylformamide. Cesium acetate (150 mg) (dried at 120° C. for 6 hr) was added to the solution, and the mixture was stirred under a nitrogen atmosphere at room temperature for 18 hr. The reaction solution was diluted with 46 mL of ethyl acetate, and the diluted solution was washed once with 11 mL of water and three times with 11 mL of semisaturated brine, was dried over a Glauber's salt and was concentrated to dryness. The residue was purified by column chromatography on silica gel (12 g, toluene:ethyl acetate:acetone=4:1:1) to give the title compound (75 mg, yield 65%).

Rf value: 0.35 (toluene:ethyl acetate:acetone=3:1:1)
ESIMS: m/z 1501 [M+Na]$^+$

Production Step 11-7

3,2',6',3'',4'''-Penta-N-tert-butoxycarbonyl-5,4''-diepi-2-hydroxy-6''-O-tritylarbekacin

[Chemical formula 125]

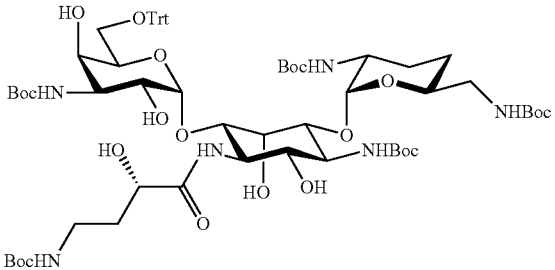

The compound (75 mg) produced in production step 11-6 was dissolved in 2.3 mL of a 0.5% solution of sodium methoxide in methanol, and the mixture was allowed to react at room temperature for one hr. The reaction mixture was neutralized with Dowex 50 W×2 ($H^+$ form, substituted with methanol), and the resin was removed by filtration. The filtrate was concentrated to dryness to give the title compound (64 mg, 96%).

Rf value: 0.60 (toluene:ethyl acetate:acetone=1:1:1)

Production Step 11-8

5,4"-Diepi-2-hydroxyarbekacin

[Chemical formula 126]

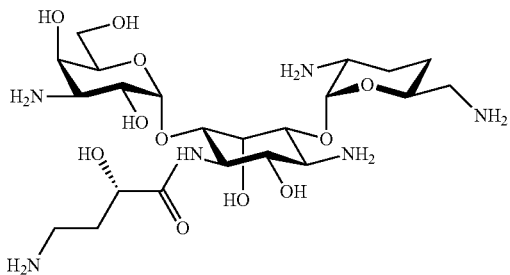

The compound (64 mg) produced in production step 11-7 was dissolved in 1.6 mL of a 90% aqueous trifluoroacetic acid solution under ice cooling. The solution was allowed to react under ice cooling for 2 hr. The reaction mixture was concentrated to dryness. Water (10 mL) was added to the residue, and the solution was washed three times with 3 mL of diethyl ether. The water layer was concentrated to dryness. 0.005 M aqueous ammonia (10 mL) was added to the residue (pH 6 to 7), and the mixture was added to a CM-Sephadex C-25 column (equilibrated with 0.005 M aqueous ammonia, 10 mL). The column was washed with 30 mL of 0.005 M aqueous ammonia, and elution was carried out with aqueous ammonia with the concentration being varied from 0.2 M (50 mL) to 0.5 M (200 mL). The corresponding fractions were concentrated to give 28.6 mg of the title compound: 5-epi-2-hydroxyarbekacin (73% as 2.5 carbonate trihydrate).

Rf value: 0.09 (chloroform:methanol: 15 M aqueous ammonia (concentrated aqueous ammonia): ethanol=4:6:7:2)

$^1$H-NMR (DCl-$D_2$O, pD~3): δ 5.44 (1H, J=3.5 Hz), 5.16 (d, 1H, J=4 Hz), 4.77 (d, 1H, J=3 Hz), 4.35 (dd, 1H, J=4.5, 9 Hz), 4.31 (t, 1H, J=11, 11 Hz), 4.17 (d, 1H, J=3 Hz), 4.14 (m, 1H), 4.13 (d, 1H, J=3, 11 Hz), 4.11 (m, 1H), 4.02 (dd, 1H, J=3, 11 Hz), 3.98 (dd, J=4, 11 Hz), 3.81 (t, 1H, J=11, 11 Hz), 3.75-3.80 (m, 2H), 3.71 (t, 1H, J=11, 11 Hz), 3.67 (dd, 1H, J=3, 11 Hz), 3.63 (m, 1H), 3.28 (dd, 1H, J=3.5, 13.5 Hz), 3.21 (t, 2H, J=7, 7 Hz), 3.11 (dd, 1H, J=7.5, 13.5 Hz), 2.23 (m, 1H), 2.05-2.13 (m, 2H), 2.00 (m, 1H), 1.94 (m, 1H), 1.64 (m, 1H).

$^{13}$C-NMR (DCl-$D_2$O, pD~3): δ 177.13, 100.42, 90.53, 76.63, 71.90, 70.56, 70.02, 68.33, 66.26, 66.20, 66.18, 65.57, 61.72, 53.73, 53.49, 52.59, 48.59, 42.96, 37.36, 31.34, 25.86, 21.32.

Calcd. for $C_{22}H_{44}N_6O_{11} \cdot 2.5H_2CO_3 \cdot 3H_2O$. C, 37.84; H, 7.13; N, 10.81.

Found, C, 37.51; H, 7.49; N, 10.96.

Example 12

5,4"-Diepi-2-hydroxydibekacin

[Chemical formula 127]

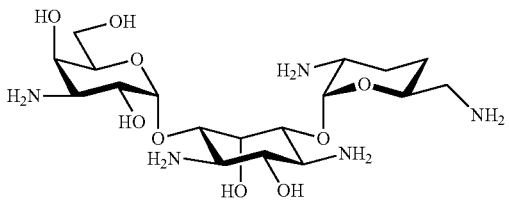

Production Step 12-1

4"-O-Acetyl-3"-azido-6"-O-benzoyl-2"-O-benzyl-3"-deoxy-5,4"-diepi-1,3,2',6'-tetra-N-tosyl-2-hydroxydibekacin

[Chemical formula 128]

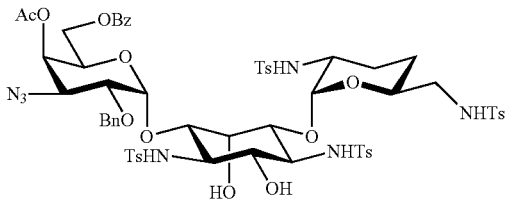

A solution of 667 mg of the compound produced in production step 10-5a in 34 mL of methylene chloride was added to the compound (1.16 g) produced in production step 10-12. Drierite (3.43 g) was added thereto, and the mixture was stirred at room temperature for 3 hr. Mercuric cyanide (1.27 g) was added to the reaction solution, and the mixture was stirred under light shielded conditions at room temperature for 42 hr. The reaction solution was filtered through Celite to remove the insolubles. The insolubles were washed with 90 mL of chloroform. The combined organic layers were washed twice with 60 mL of a saturated aqueous sodium bicarbonate solution, twice with 60 mL of a 10% aqueous sodium iodide solution and once with 60 mL of water, were dried over a Glauber's salt and were concentrated to dryness. The residue was purified by column chromatography on silica gel (40 g, chloroform→chloroform:ethyl acetate=1:1→ethyl acetate) to give the title compound (529 mg, 31%). In this case, 423 mg (36%) of the starting compound was recovered.

Rf value: 0.20 (chloroform:ethyl acetate=5:2)

ESIMS: m/z 1368 [M+Na]$^+$ $^1$H-NMR (pyridine-d5): δ 9.02 (d, 1H, J=7 Hz), 8.83 (d, 1H, J=7 Hz), 8.50 (m, 1H), 8.48 (t, 1H, J=6, 6 Hz), 7.03-8.28 (m, 26H), 6.00 (d, 1H, J=3 Hz), 5.85 (d, 1H, J=2 Hz), 5.58 (br. s, 1H), 4.81-5.26 (ABq, 2H, Jgem=12 Hz), 5.20 (br. s, 1H), 5.07 (m, 1H), 4.80-4.95 (m, 4H), 4.77 (t, 1H, J=10, 10 Hz), 4.72 (m, 1H), 4.68 (t, 1H, J=10, 10 Hz), 4.35 (m, 1H), 4.26 (br. d, 1H, J=11 Hz), 4.23 (dd, 1H, J=4, 10 Hz), 3.90 (t, J=10, 10

Hz), 3.63 (m, 1H), 3.29 (m, 2H), 2.26 (m, 1H), 2.00, 2.07, 2.15, 2.18, 2.22 (each s, each 3H), 1.48-1.64 (m, 3H).

Production Step 12-2

5,4''-Diepi-2-hydroxydibekacin

[Chemical formula 129]

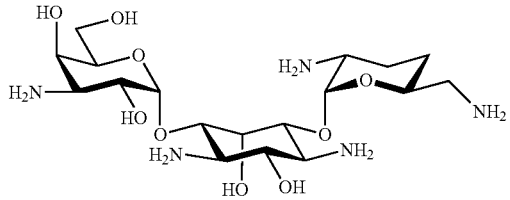

A 0.5 M solution (12 mL) of sodium methoxide in methanol was added to the compound (529 mg) produced in production step 12-1, and the mixture was allowed to react at room temperature for 2 hr. The reaction mixture was neutralized with Dowex 50 W×2 (H+ form, substituted with methanol). The resin was removed by filtration, and the filtrate was concentrated to dryness to give a crude product.

ESIMS: m/z 1222 [M+Na]+

Liquid ammonia (about 25 mL) was reservoired at −50° C. in an egg-plant type flask containing the crude product, and 732 mg of metallic sodium was added thereto at −50° C. The mixture was vigorously stirred with a glass stirrer bar for 2 hr. Methanol was gradually added until the color of radicals disappeared. The mixture was returned to room temperature to evaporate ammonia and was finally concentrated to dryness by an evaporator. Water (32 mL) was added to the residue, and the solution was adjusted to pH 4 to 5 with Dowex 50 W×2 (H+ form), and the contents of the flask including the resin as such were added to a column packed with 10 mL of the same resin. The column was washed with 120 mL of water, and elution was carried out with 1 M aqueous ammonia. A ninhydrin-positive fraction was concentrated to dryness to give a crude product. The crude product was brought to an aqueous solution (40 mL). The aqueous solution was charged into a CM-Sephadex C-25 column (equilibrated with 0.005 M aqueous ammonia, 20 mL), and the column was washed with water (40 mL). Elution was carried out with 0.05 M→0.2 M→0.5 M aqueous ammonia (each 40 mL), and the corresponding fraction was concentrated to dryness to give the title compound (104 mg, 43%, as monocarbonate monohydrate).

Rf value: 0.15 (1-butanol:ethanol:chloroform:17% aqueous ammonia=4:7:2:7).

ESIMS: m/z 468 [M+H]+, 490 [M+Na]+

$^1$H-NMR (26% ND$_3$-D$_2$O): δ 5.03, (d, 1H, J=4 Hz), 4.92 (d, 1H, J=3 Hz), 4.51 (t, 1H, J=2, 2 Hz), 4.08 (m, 1H), 3.85 (d, 1H, J=2 Hz), 3.80 (m, 1H), 3.68 (d, 2H, J=5.5 Hz), 3.60 (dd, 1H, J=4, 10.5 Hz), 3.49 (dd, 1H, J=2, 10 Hz), 3.36 (dd, 1H, J=2, 10 Hz), 3.14 (t, 1H, J=10, 10 Hz), 3.12 (t, 1H, J=10, 10 Hz), 3.10 (t, 1H, J=10, 10 Hz), 2.98 (dd, 1H, J=3, 10.5 Hz), 2.79 (m, 1H), 2.64 (dd, 1H, J=4, 13.5 Hz), 2.60 (dd, 1H, J=7.5, 13.5 Hz), 1.64-1.77 (m, 3H), 1.36 (m, 1H).

$^{13}$C-NMR (26% ND$_3$-D$_2$O): δ 102.91, 96.82, 82.89, 76.46, 75.24, 73.81, 71.40, 71.07, 70.02, 68.09, 62.70, 54.36, 53.70, 52.49, 50.87, 46.51, 28.95, 27.61.

Reference Example 1

Synthesis of (S)-2-benzyloxy-4-benzyloxycarbonylaminobutyric acid

[Chemical formula 130]

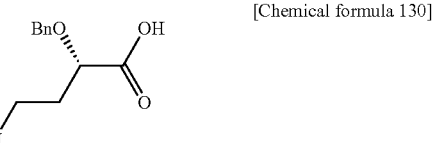

(S)-4-Benzyloxycarbonylamino-2-hydroxybutyric acid (5.25 g, 20.7 mmol) synthesized according to the report of Kawaguchi et al. (Journal of Antibiotics, Vol. 25, pp. 695-708 (1972)) was dissolved in 60 mL of N,N-dimethylformamide. Barium oxide (15.9 g, 103.7 mmol) was added under an ice bath. After the elapse of 2 min from the addition of barium oxide, barium hydroxide octahydrate (13.4 g, 42.5 mmol) was added thereto under an ice bath. After 10 min, benzyl bromide (7.5 mL, 63.1 mmol) was added thereto under an ice bath. After 5 min, the reaction solution was returned to room temperature and was vigorously stirred. After 1.5 hr, the completion of the reaction was confirmed by TLC (developing solvent system=chloroform:ethyl acetate:acetic acid=10:5:1), and water (0.5 mL) was added thereto under an ice bath. The mixture was diluted with chloroform (165 ml), and 4 N HCl (70 mL) was added thereto. Further, water (25 mL) was added followed by separation. The water layer was extracted with chloroform (50 mL). The organic layer and the extracted organic layer were combined and were washed with a saturated aqueous NaCl solution. The washed solution was dried over magnesium sulfate. The solvent was removed by distillation under the reduced pressure, and the residue was purified by column chromatography on silica gel (silica gel 60, neutral spheres, 160 g) (chloroform:ethyl acetate=4:1→chloroform:methanol=10:1→chloroform:methanol:acetic acid=10:1:0.1 (600 mL)) to give (S)-2-benzyloxy-4-benzyloxycarbonylaminobutyrylic acid (2.86 g, 8.34 mmol).

LCMS: m/z 344 [M+Na]+

$^1$H-NMR (DMSO-d6): δ 12.8 (s, 1H), 7.25-7.35 (m, 10H), 7.26 (d, 1H, J=4.2 Hz), 5.01 (s, 2H), 4.49 (ABq, 2H, Jgem=12 Hz), 3.97 (dd, 1H, J=3.7, 8.8 Hz), 3.08-3.18 (m, 2H), 1.67-1.93 (m, 2H).

Reference Example 2

(S)-2-Acetoxy-3-amino-N-benzyloxycarbonylpropanoic acid

[Chemical formula 131]

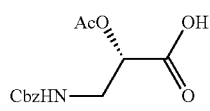

Step 1

(S)-3-Amino-N-benzyloxycarbonyl-2-hydroxypropanoic acid diphenyl methyl ester

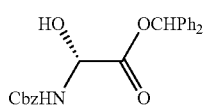

[Chemical formula 132]

N-Benzyloxycarbonylisoserine (20 mg) synthesized according to the report of R. D. Westland et al. (Carbohydr. Res., Vol. 28, pp. 268-280 (1973)) was dissolved in 0.6 mL of tetrahydrofuran. Diphenylmethylazide (24 mg) was added to the solution, and the mixture was stirred at room temperature for 2 hr. The reaction solution was concentrated under the reduced pressure, and the residue was purified by column chromatography on silica gel (2 g, hexane:ethyl acetate=5: 1→4:1→3:1) to give the title compound (33 mg, quantitative).

Rf value: 0.54 (hexane:ethyl acetate=1:1)

$^1$H-NMR (CDCl$_3$): δ 7.25-7.35 (m, 15H), 6.91 (s, 1H), 5.05 (br, 2H), 4.39 (s, 1H), 3.68-3.71 (m, 1H), 3.49-3.58 (dd, 1H, J=6.1, 6.9 Hz), 3.21 (m, 1H)

Step 2

(S)-2-Acetoxy-3-amino-N-benzyloxycarbonylpropanoic acid

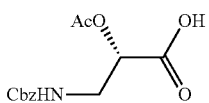

[Chemical formula 133]

The compound (26.3 mg) produced in production step 1 was dissolved in 1.0 mL of methylene chloride. Pyridine (70 μL) was added to the solution. Acetic anhydride (20 μL) and 0.8 mg of 4-dimethylaminopyridine were added thereto at 0° C. The reaction mixture was returned to room temperature and was stirred for 2.5 hr. Methanol (100 μL) was added thereto, and the mixture was stirred at room temperature for 20 min to complete the reaction. Chloroform (20 mL) was added thereto, and the mixture was washed with 15 mL of water, was dried over a Glauber's salt and was concentrated to dryness to give (S)-3-amino-2-acetoxy-N-benzyloxycarbonylpropanoic acid diphenyl methyl ester (28.6 mg (99%)).

Rf value: 0.62 (hexane:ethyl acetate=1:1)

$^1$H-NMR (CDCl$_3$): δ 7.25-7.37 (m, 15H), 6.87 (s, 1H), 5.26 (dd, 1H, J=4.8, 5.2 Hz), 5.06 (br, 2H), 4.93 (s, 1H), 3.66-3.75 (m, 2H), 2.11 (s, 3H).

The above compound (28.6 mg) was dissolved in 0.6 mL of chloroform. Trifluoroacetic acid (0.6 mL) was added to the solution at 0° C., and the mixture was stirred at room temperature for 2 hr. The reaction mixture was subjected to azeotropic distillation three times with toluene under the reduced pressure to dryness to give the title compound (21.2 mg) as a crude product.

Rf value: 0.44 (chloroform:ethyl acetate:acetic acid=10:5: 1).

$^1$H-NMR (CDCl$_3$): δ 7.26-7.35 (m, 5H), 5.25 (dd, 1H, J=4.8, 5.1 Hz), 5.09 (br, 2H), 4.86 (s, 1H), 3.62-3.70 (m, 2H), 2.12 (s, 3H).

Reference Example 3

(S)-5-Amino-2-benzyloxy-N-benzyloxycarbonylpentanoic acid

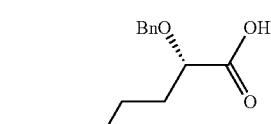

[Chemical formula 134]

(S)-5-Amino-N-benzyloxycarbonyl-2-hydroxypentanoic acid (21 mg) synthesized according to the report of R. D. Westland et al. (Carbohydr. Res., Vol. 28, pp. 268-280 (1973)) was dissolved in 0.24 mL of N,N-dimethylformamide. Barium oxide (64 mg) was added to the solution under ice cooling, and the mixture was stirred for 2 min. Next, barium hydroxide (5.4 mg) was added thereto, and the mixture was further stirred at the same temperature for 10 min. Benzyl bromide (30 μL) was added thereto. After the elapse of 5 min from the start of stirring, the reaction mixture was returned to room temperature, and the mixture was vigorously stirred for 1.5 hr. Water (15 mL) was added under ice cooling, and the mixture was diluted with 30 mL of chloroform. 4 N HCl (0.28 mL) was added to the diluted solution, and the mixture was stirred for 5 min. The reaction solution was separated, and the water layer was again extracted with 20 mL of chloroform. The organic layer and the above organic layer were combined and were dried over magnesium sulfate. The solution thus obtained was concentrated under the reduced pressure, and the residue was purified by column chromatography on silica gel (30 g, hexane:ethyl acetate=4:1→chloroform:methanol=10:1) to give the title compound (11 mg, 39%).

Rf value: 0.46 (chloroform:ethyl acetate:acetic acid=10:5: 1).

$^1$H-NMR (CDCl$_3$): δ 7.32-7.35 (m, 10H), 5.08 (br, 2H), 4.70 (d, 1H, J=11.5 Hz), 4.46 (d, 1H, J=11.5 Hz), 4.00 (t, 1H, J=4.99 Hz), 3.19 (br, 2H), 1.84 (dt, 2H, J=4.99, 7.0 Hz), 1.66 (tt, 2H, J=7.0, 7.2 Hz).

Reference Example 4

(S)-6-Amino-2-benzyloxy-N-benzyloxycarbonylhexanoic acid

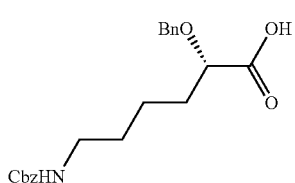

[Chemical formula 135]

(S)-6-Amino-N-benzyloxycarbonyl-2-hydroxyhexanoic acid (450 mg) synthesized according to the report of R. D. Westland et al. (Carbohydr. Res., Vol. 28, pp. 268-280 (1973)) was dissolved in 5.4 mL of N,N-dimethylformamide. Barium oxide (1230 mg) was added under ice cooling, and the mixture was stirred for 2 min. Next, barium hydroxide (1061 mg) was added thereto, and the mixture was further stirred at the same temperature for 10 min. Thereafter, 0.57 mL of benzyl bromide was added. After the elapse of 5 min from the addition of benzyl bromide, the mixture was returned to room temperature, and the mixture was vigorously stirred for 1.5 hr. Water (15 mL) was added thereto under ice cooling. The mixture was diluted with 30 mL of chloroform. 4 N HCl (6.0 mL) was added thereto, and the mixture was stirred for 5 min. The reaction solution was separated by filtration. The water layer was again extracted with 25 mL of chloroform. The organic layer and the above organic layer were combined and were dried over magnesium sulfate. The solution was concentrated under the reduced pressure, and the residue was purified by column chromatography on silica gel (32 mg, hexane:ethyl acetate=3:1) to give the title compound (196 mg, 33%).

Rf value: 0.47 (chloroform:ethyl acetate:acetic acid=10:5:1)

$^1$H-NMR (CDCl$_3$): d 7.29-7.34 (m, 10H), 5.09 (br, 2H), 4.74 (d, 1H, J=11.7 Hz), 4.46 (d, 1H, J=11.7 Hz), 3.97 (t, 1H, J=5.7 Hz), 3.16 (br, 2H), 1.77-1.83 (m, 2H), 1.41-1.50 (m, 4H).

Reference Example 5

(R)-2-Benzyloxy-4-benzyloxycarbonylaminobutyric acid

[Chemical formula 136]

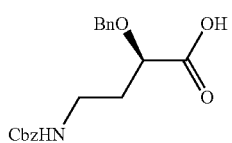

4-Benzyloxycarbonylamino-2-(R)-hydroxybutyric acid (2.245 g) synthesized according to the method of H. Naito et al. (J. Antibiot., Vol. 26, pp. 297-301 (1973)) was dissolved in 25.6 mL of N,N-dimethylformamide. Barium oxide (6.795 g) was added to the solution under ice cooling with stirring, and the mixture was vigorously stirred for 2 min. Barium hydroxide octahydrate (5.593 g) was added to the reaction mixture, and the mixture was vigorously stirred under ice cooling for 10 min. Benzyl bromide (3.16 mL) was added thereto, and the mixture was vigorously stirred under ice cooling for 5 min. The reaction mixture was returned to room temperature and was vigorously stirred for 1.5 hr. Water (0.48 mL) was added under ice cooling, and the mixture was diluted with 70 mL of chloroform. 4 M hydrochloric acid (31 mL) was added to the diluted solution. Water (11 mL) was then added thereto followed by separation. The water layer was extracted with 22 mL+10 mL of chloroform. The combined organic layers were washed with 30 mL of saturated brine, were dried over magnesium sulfate and were concentrated to dryness to give 4.54 g of a crude product. The product was purified by column chromatography on 70 g of a neutral silica gel (chloroform→chloroform:ethyl acetate=4:1→chloroform:methanol=10:1→chloroform:methanol-acetic acid=10:1:0.1) to give the title compound (1.107 g, 36%).

Rf value: 0.57 (chloroform:ethyl acetate:acetic acid=10:5:1)

ESIMS: m/z 342 [M−H]$^-$ $^1$H-NMR (CDCl$_3$): δ7.25-7.40 (10H), 5.06 (s, 2H), 4.94 (br. s, 1H), 4.40-4.76 (ABq, 2H, Jgem=11 Hz), 4.06 (t, 1H, J=5.5, 5.5 Hz), 3.35 (m, 2H), 2.02 (m, 2H).

Test Example 1

Antimicrobial Activity

MIC of the compound represented by formula (I) produced in Example 1 against an MRSA strain, specifically a clinically isolated MRSA strain (n=9), which has low sensitivity to arbekacin and against which the minimal inhibitory concentration (MIC, μg/mL) is 4 to 8, was measured by an agar plate dilution method according to the standard method of Japan Society of Chemotherapy (Chemotherapy, Vol. 29, pp. 76 to 79, 1981).

As a result, the compound represented by formula (I) has an MIC value of 0.5 to 2. The compound represented by formula (I) had higher antimicrobial activity than arbekacin, against the above MRSA strain having low sensitivity to arbekacin.

Test Example 2

Antimicrobial Activity

MIC of the 2-hydroxyarbekacins produced in Examples 1 to 4 and the compounds produced in Examples 5, 6, 8, 9, 10, and 11, against an MRSA strain, specifically a clinically isolated MRSA strain, which is different from that used in Test Example 1 and has high resistance to arbekacin and against which the MIC value (μg/mL) is 128, was measured by an agar plate dilution method according to the standard method of Japan Society of Chemotherapy (Chemotherapy, Vol. 29, pp. 76 to 79, 1981).

As a result, these compounds had an MIC value of 2 to 32, indicating that the compounds represented by formula (I) had higher antimicrobial activity than arbekacin, against the MRSA strain showing high resistance to arbekacin.

Test Example 3

Evaluation of Influence on Kidney of Normal Mice

An evaluation system of influence on the kidney was constructed based on renal disease model preparation method using gentamicin (KIDNEY AND DIALYSIS, Vol. 31, 1991, extra edition, "Renal Disease Model", p. 423 "Drug-induced Renal Damage and its Examination Method," Kidney and Dialysis Editorial Committee, published by TOKYOI-GAKUSYA). The influence of the compound represented by formula (I) produced in Example 1 on the kidney was evaluated using this evaluation system. A physiological saline administration group and an arbekacin administration group were set as control groups. Each group consisted of four mice (Crj: CD-1 (ICR) female mice of eight weeks old).

In the above evaluation system, the evaluation of nephrotoxicity was carried out using NAG as an index. NAG exists in lysosome in each tissue of humans and animals, is an enzyme, which converts a mucopolysaccharide to a glycoprotein, for example, converts β-N-acetyl-D-glucosaminide to β-N-acetyl-D-glucosamine, and is plentifully present in proximal uriniferous tubule epithelial cells of the kidney in which aminoglycoside antibiotics are particularly accumulated. When the kidney, especially its proximal uriniferous tubule is damaged, NAG is released into urine to increase the amount of NAG in the urine. Accordingly, the increase in the amount of NAG in urine is considered to reflect proximal uriniferous tubule damage and is adopted as one of biochemical markers for estimating the level of renal insufficiency in clinical test items. The amount of NAG is measured by an examination method, for example, an MCP-NAG method (Outline of Latest Internal Medicine, Vol. 4, Clinical Laboratory—Kensa No Susumekata To Deta No Yomikata (How To Forward Examination and How To Read Data)—<Naika Soron 4 (General Remarks Of Internal Medicine 4> p. 274, Imura et al. (ed.), published by Nakayama Syoten Co., Ltd., 1994).

A solution of physiological saline of the compound according to the present invention having a concentration of 12 mg/mL was administered to the mice in each group at a dose of 120 mg/kg/day (in two divided doses; morning and afternoon) for 4 days by repeated intraperitoneal administration. Naturally excreted urine was collected for about 24 hr from the completion of the administration in the morning on day 4, and the amount of NAG in the urine was measured by the MCP-NAG method. The same treatment was carried out for the physiological saline administration group and the arbekacin administration group.

The results were as shown in Table 1. Table 1 shows the average value of the amount of NAG for each group.

TABLE 1

Influence on kidney of normal mice

| Compound administered | Amount of NAG in urine (mIU) |
|---|---|
| Compound represented by formula (I) | 74.7 |
| Arbekacin | 135.0 |
| Physiological saline | 19.7 |

As described in Table 1, the amount of NAG in the urine for the group to which the compound represented by formula (I) had been administered, was smaller than the amount of NAG for the group to which arbekacin has been administered.

Reference Test Example 1

The influence of arbekacin and an arbekacin analogue TS2037 (5,4″-diepiarbekacin) produced according to the description of WO 2005/070945 on the kidney was evaluated in the same manner as in Test Example 3. As a result, the amount of NAG in the urine for the TS2037 administration group was 358.8 (mIU), whereas the amount of NAG in the urine for the arbekacin administration group was 168.5 (mIU). That is, the NAG amount for arbekacin analogue TS2037 was higher than that for arbekacin.

The invention claimed is:

1. A method for inhibiting proliferation of methicillin-resistant *Staphylococcus aureus*, or for sterilizing methicillin-resistant *Staphylococcus aureus*; comprising administering a compound represented by formula (Ia) or its pharmacologically acceptable salt, or their diastereomer mixture with respect to the carbon atom attached with * to an animal:

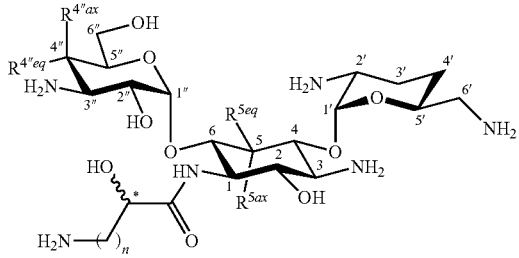

(1a)

wherein
$R^{5ax}$ and $R^{5eq}$, which are different from each other, represent a hydrogen atom or hydroxyl, and
$R^{4″ax}$ and $R^{4″eq}$, which are different from each other, represent a hydrogen atom or hydroxyl,
n is an integer of 1 to 4, and
the steric configuration of carbon atom attached with * represents R or S.

2. The method according to claim 1 or its pharmacologically acceptable salt, or their diastereomer mixture with respect to the carbon atom attached with *, wherein
$R^{5ax}$ represents a hydrogen atom and
$R^{5eq}$ represents hydroxyl.

3. The method according to claim 1 or its pharmacologically acceptable salt, or their diastereomer mixture with respect to the carbon atom attached with *, wherein
$R^{5ax}$ represents hydroxyl and
$R^{5eq}$ represents a hydrogen atom.

4. The method according to claim 1, wherein the compound represented by formula (Ia) or its pharmacologically acceptable salt, or their diastereomer mixture with respect to the carbon atom attached with * is a compound represented by formula (I) or its pharmacologically acceptable salt:

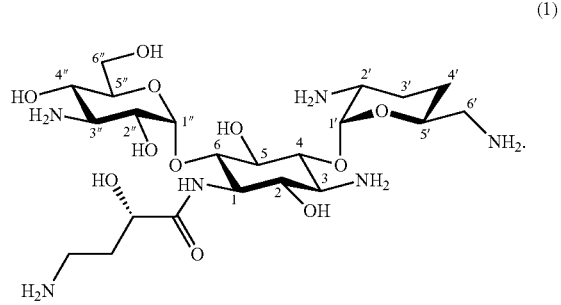

(1)

5. The method according to claim 1, wherein the animal is a human.

* * * * *